US012575786B2

(12) United States Patent
Capodilupo et al.

(10) Patent No.: US 12,575,786 B2
(45) Date of Patent: ***Mar. 17, 2026

(54) DETECTING SLEEP INTENTION

(71) Applicant: Whoop, Inc., Boston, MA (US)

(72) Inventors: Emily Rachel Capodilupo, Boston, MA (US); John Vincenzo Capodilupo, Boston, MA (US)

(73) Assignee: Whoop, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/600,674

(22) Filed: Mar. 9, 2024

(65) Prior Publication Data

US 2024/0206803 A1 Jun. 27, 2024

Related U.S. Application Data

(63) Continuation of application No. 17/117,593, filed on Dec. 10, 2020, now Pat. No. 11,925,473.

(51) Int. Cl.
| | |
|---|---|
| *A61B 5/00* | (2006.01) |
| *A61B 5/0205* | (2006.01) |
(Continued)

(52) U.S. Cl.
CPC ........ *A61B 5/4809* (2013.01); *A61B 5/02055* (2013.01); *A61B 5/1118* (2013.01);
(Continued)

(58) Field of Classification Search
None
See application file for complete search history.

(56) References Cited

U.S. PATENT DOCUMENTS

| | | | | |
|---|---|---|---|---|
| 11,013,883 B2 * | 5/2021 | Youngblood | ........ | A61B 5/1103 |
| 11,766,213 B1 * | 9/2023 | Kahn | ................... | A61B 5/4818 |
| | | | | 600/529 |

(Continued)

FOREIGN PATENT DOCUMENTS

| | | |
|---|---|---|
| EP | 3332698 | 6/2018 |
| EP | 3766410 | 1/2021 |

(Continued)

OTHER PUBLICATIONS

"Sleep Auto-Detection—WHOOP", URL:https://web.archive.org/web/20200807131951/https://support.whoop.com/hc/en-us/articles/360023249233-Sleep-Auto-Detection [retrieved on Jun. 14, 2021] Aug. 7, 2020 , 2 pages.

(Continued)

*Primary Examiner* — Carl H Layno
*Assistant Examiner* — Manolis Pahakis
(74) *Attorney, Agent, or Firm* — Strategic Patents, P.C.

(57) ABSTRACT

A wearable physiological monitoring device is configured to determine a wearer's sleep intention. In particular, the device evaluates activity that might be objectively associated with awaking from sleep in order to distinguish between a wearer's intention to end sleep and transitory stirring or other intermittent activity occurring in the context of a longer sleep interval. By evaluating sleep intention more accurately in this manner, the device can advantageously request sleep analysis from a remote server in those instances where a user intends to end a period of sleep (so that this data can be available to the user more quickly), while avoiding unnecessary or redundant server-side processing of sleep data in those instances where a user intends to continue sleeping.

20 Claims, 30 Drawing Sheets

(51) Int. Cl.
    *A61B 5/024*        (2006.01)
    *A61B 5/11*         (2006.01)

(52) U.S. Cl.
    CPC ............ *A61B 5/1126* (2013.01); *A61B 5/681*
        (2013.01); *A61B 5/7267* (2013.01); *A61B*
        *5/02427* (2013.01); *A61B 2562/0219* (2013.01)

(56)             References Cited

U.S. PATENT DOCUMENTS

| | | | |
|---|---|---|---|
| 2002/0017994 A1* | 2/2002 | Balkin ................. | A61B 5/4806 |
| | | | 340/573.1 |
| 2002/0124295 A1 | 9/2002 | Fenwick et al. | |
| 2005/0042589 A1 | 2/2005 | Hatlestad et al. | |
| 2010/0292599 A1 | 11/2010 | Oleson et al. | |
| 2011/0230790 A1* | 9/2011 | Kozlov ................ | G04G 13/026 |
| | | | 600/595 |
| 2012/0179061 A1* | 7/2012 | Ramanan ............ | A61M 16/024 |
| | | | 128/204.23 |
| 2013/0310657 A1 | 11/2013 | Sullivan et al. | |
| 2014/0180019 A1 | 6/2014 | Martinez et al. | |
| 2016/0135743 A1 | 5/2016 | Cobbett et al. | |
| 2016/0192218 A1 | 6/2016 | Peters | |
| 2016/0192886 A1 | 7/2016 | Nunn et al. | |
| 2016/0266606 A1 | 9/2016 | Ricci | |
| 2016/0361515 A1* | 12/2016 | Jung .................. | A61B 5/02055 |
| 2016/0374567 A1* | 12/2016 | Breslow ............. | A61B 5/02405 |
| | | | 600/301 |
| 2016/0374569 A1* | 12/2016 | Breslow ............. | A63B 24/0087 |
| | | | 600/301 |
| 2017/0086731 A1 | 3/2017 | Raymann et al. | |
| 2017/0094046 A1 | 3/2017 | Raymann et al. | |
| 2017/0352287 A1* | 12/2017 | Arnold ................... | A61B 5/743 |
| 2018/0220962 A1 | 8/2018 | Palley et al. | |
| 2018/0242654 A1 | 8/2018 | Marikkar et al. | |
| 2019/0083028 A1* | 3/2019 | Garcia Molina ...... | G16H 20/70 |
| 2019/0110748 A1 | 4/2019 | Cho et al. | |
| 2019/0159680 A1 | 5/2019 | Tanaka et al. | |
| 2019/0192068 A1* | 6/2019 | Tsoneva ................. | A61B 5/374 |
| 2019/0213060 A1 | 7/2019 | Raymann et al. | |
| 2019/0246974 A1* | 8/2019 | Hilbig .................. | A61B 5/7203 |
| 2019/0254591 A1* | 8/2019 | Garcia Molina ..... | A61M 21/02 |

| | | | |
|---|---|---|---|
| 2020/0359913 A1* | 11/2020 | Ghodrati ............... | A61B 5/1117 |
| 2021/0142894 A1 | 5/2021 | Räisänen | |
| 2021/0146089 A1* | 5/2021 | Bremer .................. | G04C 11/00 |
| 2021/0150873 A1* | 5/2021 | Shouldice ............ | A61B 5/7228 |
| 2021/0398666 A1* | 12/2021 | Maslik .................. | A61B 5/4842 |
| 2021/0401314 A1 | 12/2021 | Pho et al. | |
| 2021/0401378 A1 | 12/2021 | Pho et al. | |
| 2021/0407684 A1 | 12/2021 | Pho et al. | |
| 2022/0183618 A1* | 6/2022 | Capodilupo ......... | A61B 5/4809 |
| 2022/0273269 A1* | 9/2022 | Capodilupo ......... | A61B 5/0004 |
| 2022/0287631 A1* | 9/2022 | Peer ...................... | G16H 50/30 |
| 2022/0401689 A1* | 12/2022 | Campanella .......... | A61M 21/00 |
| 2023/0059947 A1* | 2/2023 | Bali ..................... | A61B 5/0816 |
| 2023/0073907 A1* | 3/2023 | Capodilupo ......... | G04G 13/021 |
| 2023/0233158 A1* | 7/2023 | Mahadevan ......... | A61B 5/7282 |
| | | | 600/301 |

FOREIGN PATENT DOCUMENTS

| | | |
|---|---|---|
| KR | 100659566 | 12/2006 |
| WO | WO-2014188171 | 11/2014 |
| WO | WO-2015134654 | 9/2015 |
| WO | WO-2019168475 | 9/2019 |
| WO | WO-2019213114 | 11/2019 |

OTHER PUBLICATIONS

"Automatic sleep tracking—Sleep as Android", URL:https://web.archive.org/web/20200627154503/https://sleep.urbandroid.org/documentation/core/automatic-sleep-tracking/ [retrieved on Jun. 14, 2021] Jun. 27, 2020 , 3 pages.

USPTO, "U.S. Appl. No. 17/117,593 Final Office Action mailed May 4, 2023", 26 pages.

USPTO, "U.S. Appl. No. 17/117,593 Non-Final Office Action mailed Nov. 30, 2022", 22 pages.

USPTO, "U.S. Appl. No. 17/117,593 Notice of Allowance mailed Nov. 6, 2023", 8 pages.

EPO, "EP Application No. 21159369.4 Examination Report mailed May 2, 2024", 6 pages.

EPO, "EP Application No. 21159369.4 Search Report mailed Jun. 24, 2021", 8 pages.

* cited by examiner

100

106

102

104

104

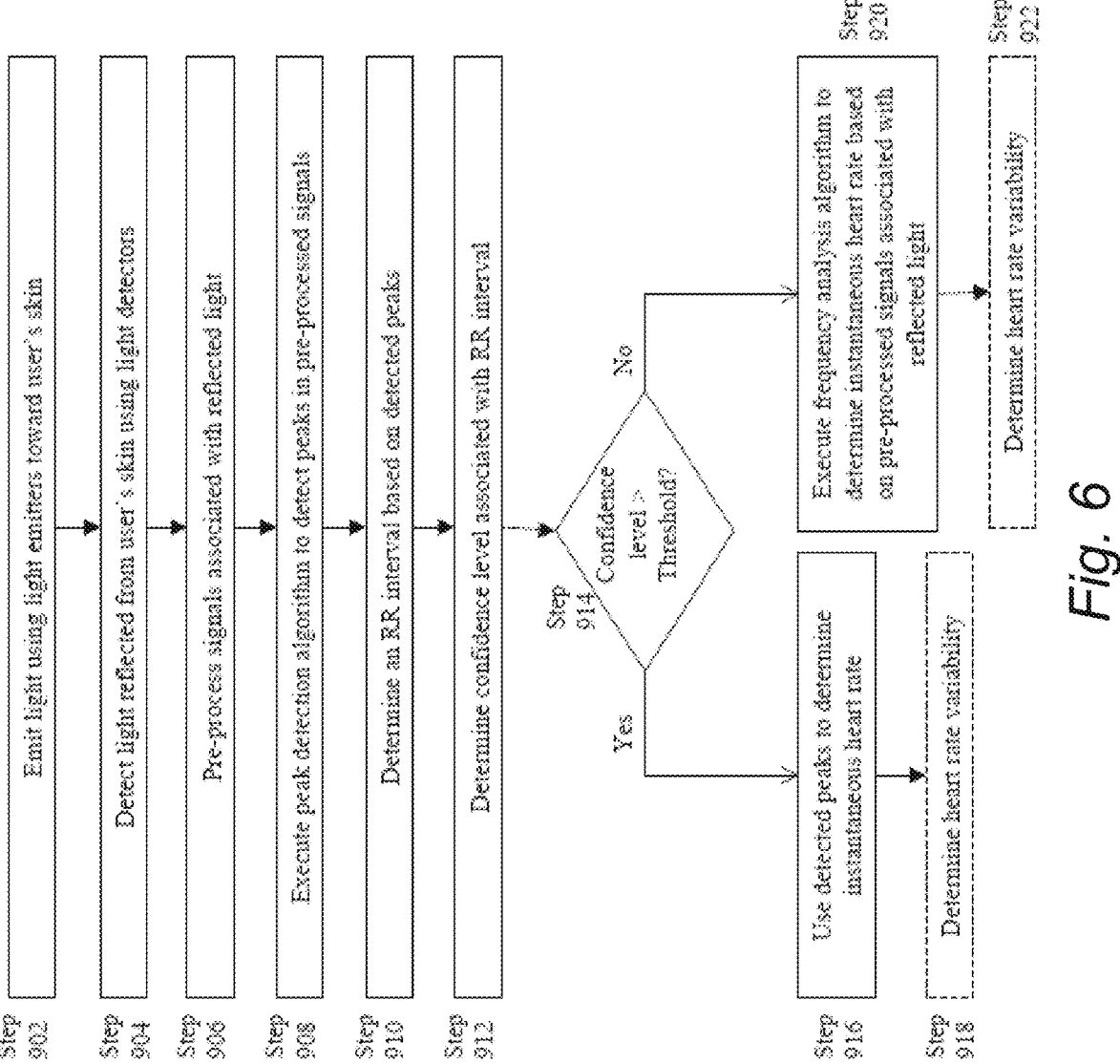

Step 902 — Emit light using light emitters toward user's skin

Step 904 — Detect light reflected from user's skin using light detectors

Step 906 — Pre-process signals associated with reflected light

Step 908 — Execute peak detection algorithm to detect peaks in pre-processed signals Step 910 — Determine an RR interval based on detected peaks Step 912 — Determine confidence level associated with RR interval Step 914 — Confidence level > Threshold?

Yes

Step 916 — Use detected peaks to determine instantaneous heart rate

Step 918 — Determine heart rate variability

No

Step 920 — Execute frequency analysis algorithm to determine instantaneous heart rate based on pre-processed signals associated with reflected light Step 922 — Determine heart rate variability

Fig. 6

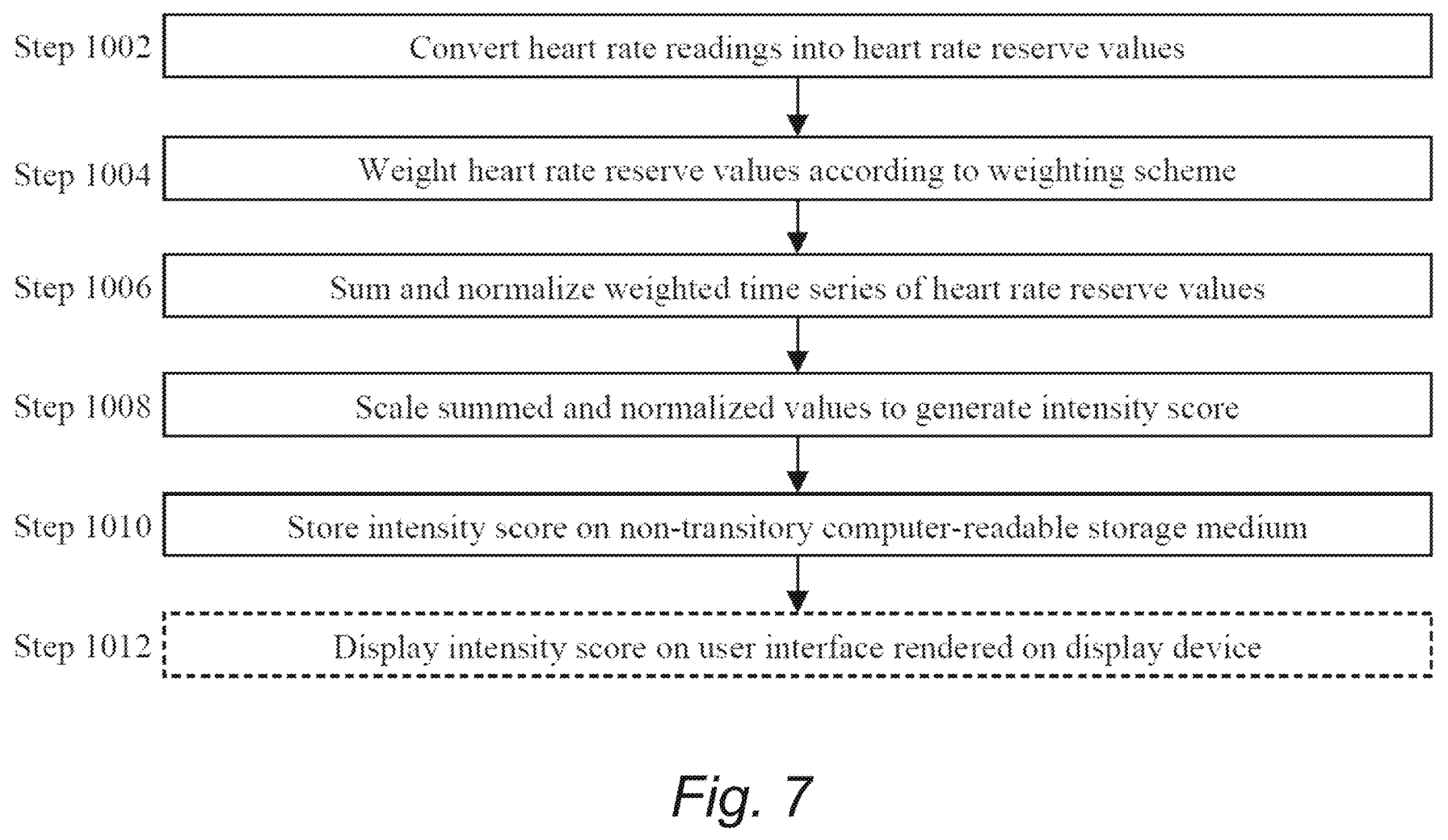

Step 1002 — Convert heart rate readings into heart rate reserve values

Step 1004 — Weight heart rate reserve values according to weighting scheme

Step 1006 — Sum and normalize weighted time series of heart rate reserve values

Step 1008 — Scale summed and normalized values to generate intensity score

Step 1010 — Store intensity score on non-transitory computer-readable storage medium Step 1012 — Display intensity score on user interface rendered on display device

*Fig. 7*

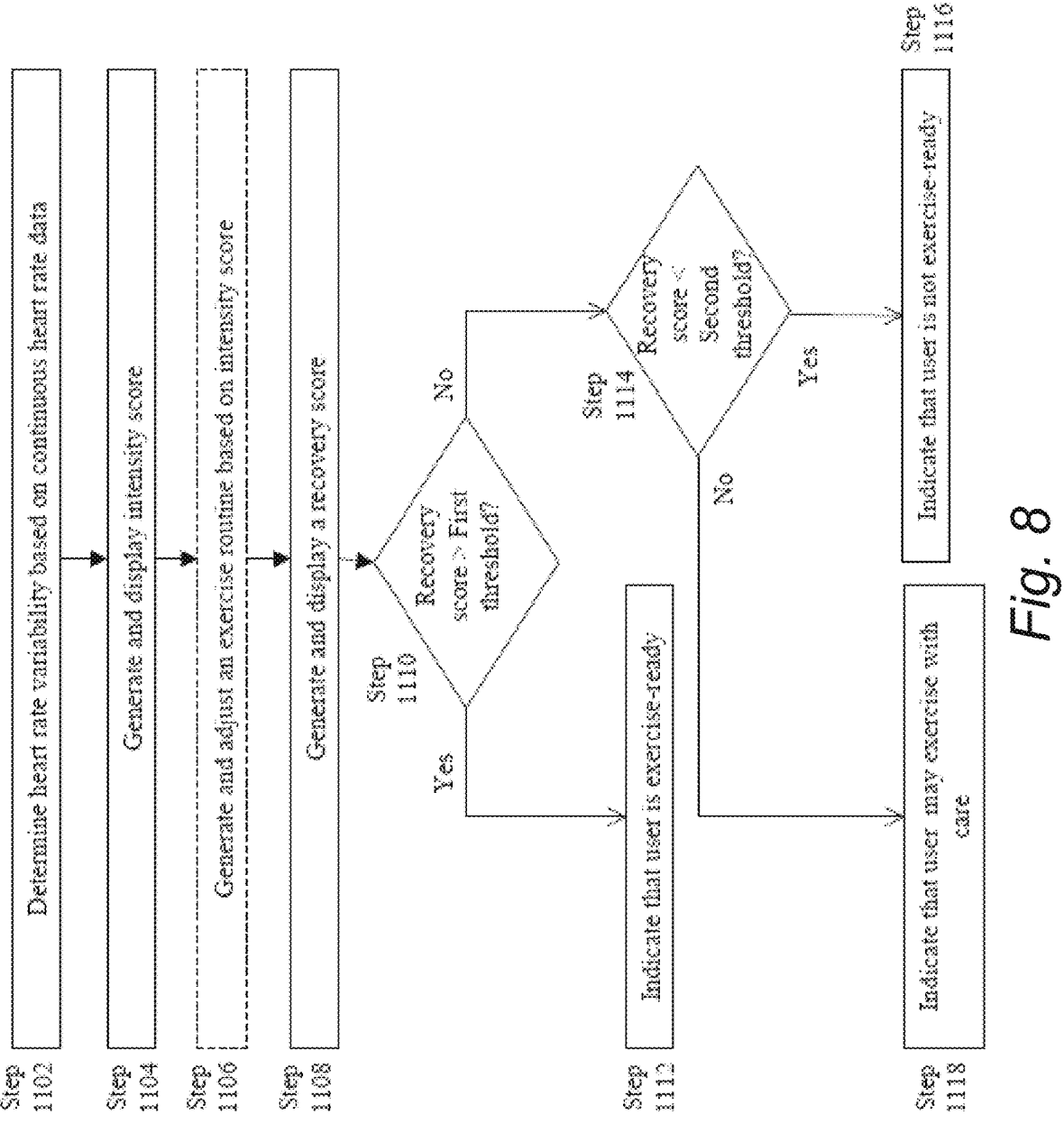

Step 1102 — Determine heart rate variability based on continuous heart rate data Step 1104 — Generate and display intensity score Step 1106 — Generate and adjust an exercise routine based on intensity score Step 1108 — Generate and display a recovery score Step 1110 — Recovery score > First threshold?

Yes → Step 1112 — Indicate that user is exercise-ready

No → Step 1114 — Recovery score < Second threshold?

Yes → Step 1116 — Indicate that user is not exercise-ready

No → Step 1118 — Indicate that user may exercise with care

Figure 13B:
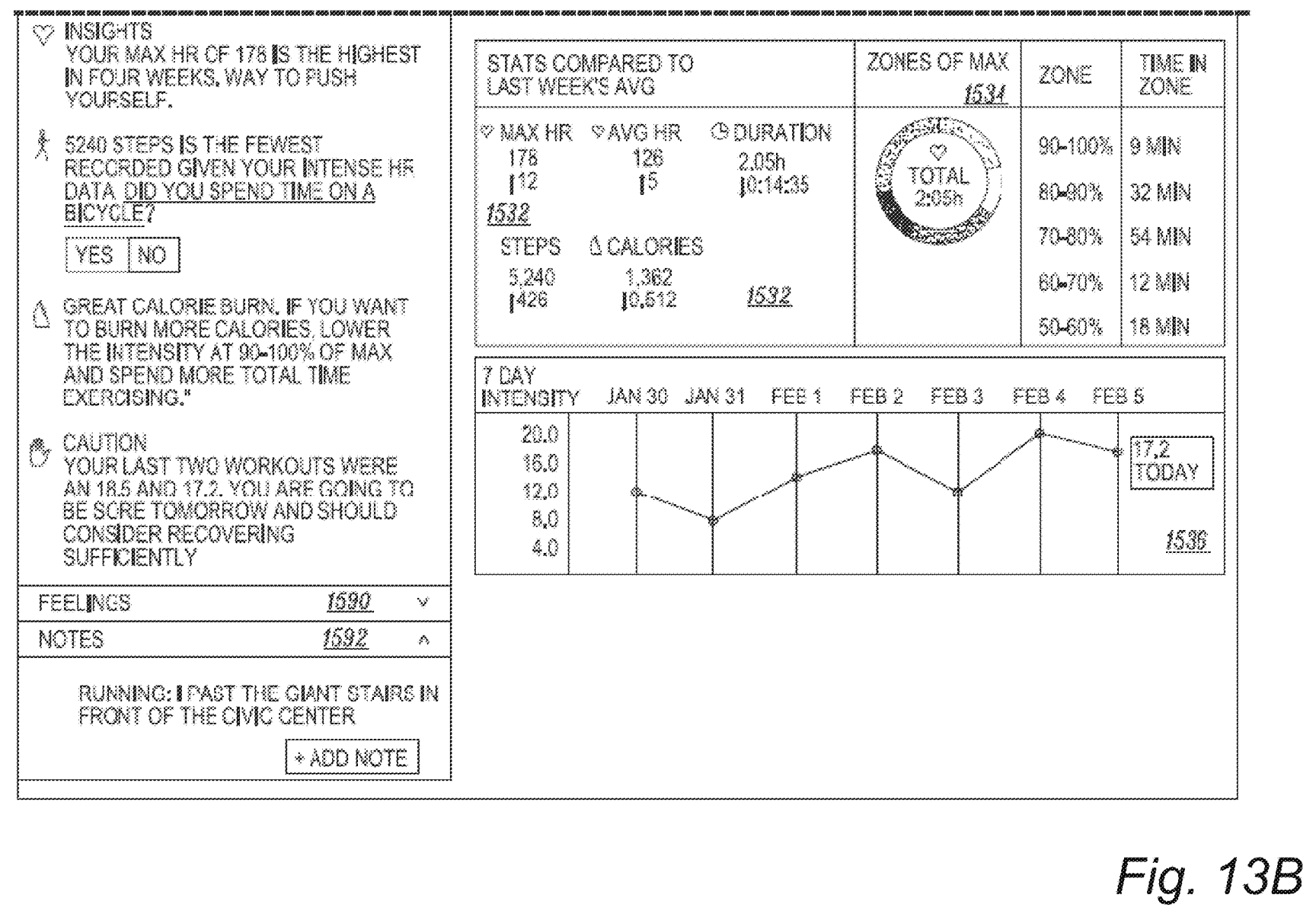

INSIGHTS
YOUR MAX HR OF 178 IS THE HIGHEST IN FOUR WEEKS. WAY TO PUSH YOURSELF.

5,240 STEPS IS THE FEWEST RECORDED GIVEN YOUR INTENSE HR DATA. DID YOU SPEND TIME ON A BICYCLE?

YES  NO

GREAT CALORIE BURN. IF YOU WANT TO BURN MORE CALORIES, LOWER THE INTENSITY AT 90-100% OF MAX AND SPEND MORE TOTAL TIME EXERCISING."

CAUTION
YOUR LAST TWO WORKOUTS WERE AN 18.5 AND 17.2. YOU ARE GOING TO BE SORE TOMORROW AND SHOULD CONSIDER RECOVERING SUFFICIENTLY

FEELINGS    1590    ˅
                     ˄
NOTES    1592
RUNNING: I PAST THE GIANT STAIRS IN FRONT OF THE CIVIC CENTER

+ ADD NOTE

STATS COMPARED TO LAST WEEK'S AVG

MAX HR    AVG HR    DURATION
178          128         2.05h
112           15          10:14:35    1592

STEPS
5,240      CALORIES
1426        1,362
1592        10,512    1592

ZONES OF MAX    1534

TOTAL
2.05h

ZONE        TIME IN ZONE
90-100%    9 MIN
80-90%     32 MIN
70-80%     54 MIN
60-70%     12 MIN
50-60%     18 MIN 17.2
TODAY

1536

7 DAY INTENSITY 20.0
16.0
12.0
8.0
4.0

JAN 30  JAN 31  FEB 1  FEB 2  FEB 3  FEB 4  FEB 5

*Fig. 14B*

INSIGHTS — 1568
YOU HAD AN ELEVATED HR AT 9:30AM ALTHOUGH LITTLE MOVEMENT. DID YOU DRINK COFFEE THIS MORNING?

YES | NO — 1572

AT 2:30PM YOU HAD HIGH LEVELS OF SWEAT ALTHOUGH LITTLE MOVEMENT. THIS APPEARS TO BE A STRESSFUL MOVEMENT IN YOUR DAY.

CAUTION — 1570
YOUR RHR OF 58 HAS BEEN ELEVATED FOR TWO DAYS. THIS MAY BE A RESULT OF YOUR HIGH INTENSITY WORKOUTS RECENTLY. CONSIDER REST OR YOU MAY BE SUSCEPTIBLE TO OVERTRAINING OR ILLNESS

FEELINGS   1590   ∨
           1592   ∧

NOTES
RUNNING: I PAST THE GIANT STAIRS IN FRONT OF THE CIVIC CENTER
+ ADD NOTE

STATS
LAST WEEK'S AVG

TOTAL CALORIE BURN
20.0
16.0
12.0
8.0
4.0

RHR
58
12   1566

STEPS
11,526
1364

JAN 30 | JAN 31 | FEB 1 | FEB 2 | FEB 3 | FEB 4 | FEB 5

3.05k TODAY
1558

*Fig. 15B*

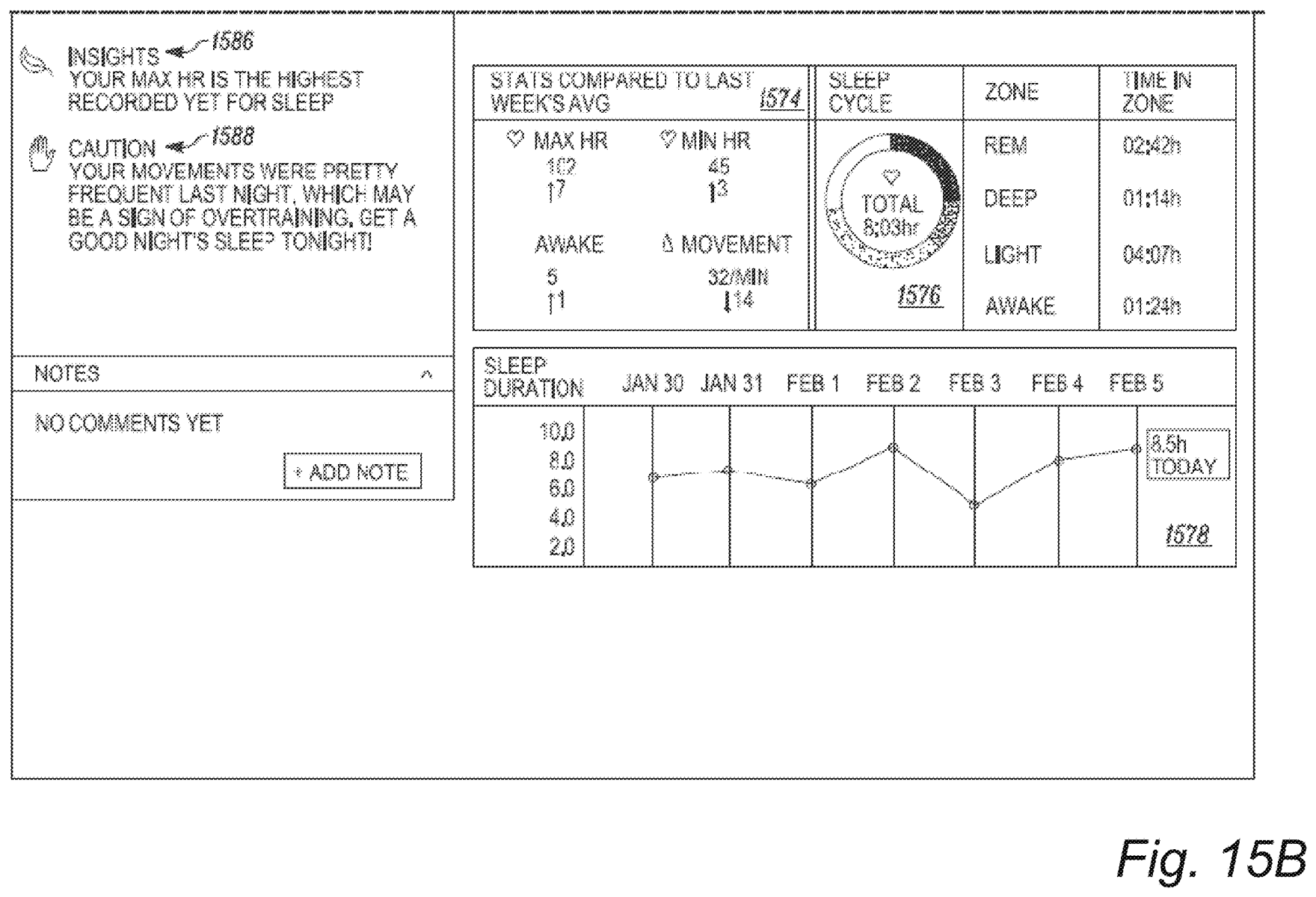

INSIGHTS 1586
YOUR MAX HR IS THE HIGHEST RECORDED YET FOR SLEEP

CAUTION 1588
YOUR MOVEMENTS WERE PRETTY FREQUENT LAST NIGHT, WHICH MAY BE A SIGN OF OVERTRAINING. GET A GOOD NIGHTS SLEEP TONIGHT!

STATS COMPARED TO LAST WEEKS AVG 1574

MAX HR
102
17

MIN HR
45
13

AWAKE
5
11

MOVEMENT
32MIN
114

SLEEP CYCLE
TOTAL 8:03hr
1576

| ZONE | TIME IN ZONE |
|---|---|
| REM | 02:42h |
| DEEP | 01:14h |
| LIGHT | 04:07h |
| AWAKE | 01:24h |

SLEEP DURATION 10.0
8.0
6.0
4.0
2.0

JAN 30  JAN 31  FEB 1  FEB 2  FEB 3  FEB 4  FEB 5

8.5h TODAY

1578

NOTES

NO COMMENTS YET

+ ADD NOTE

*Fig. 16B*

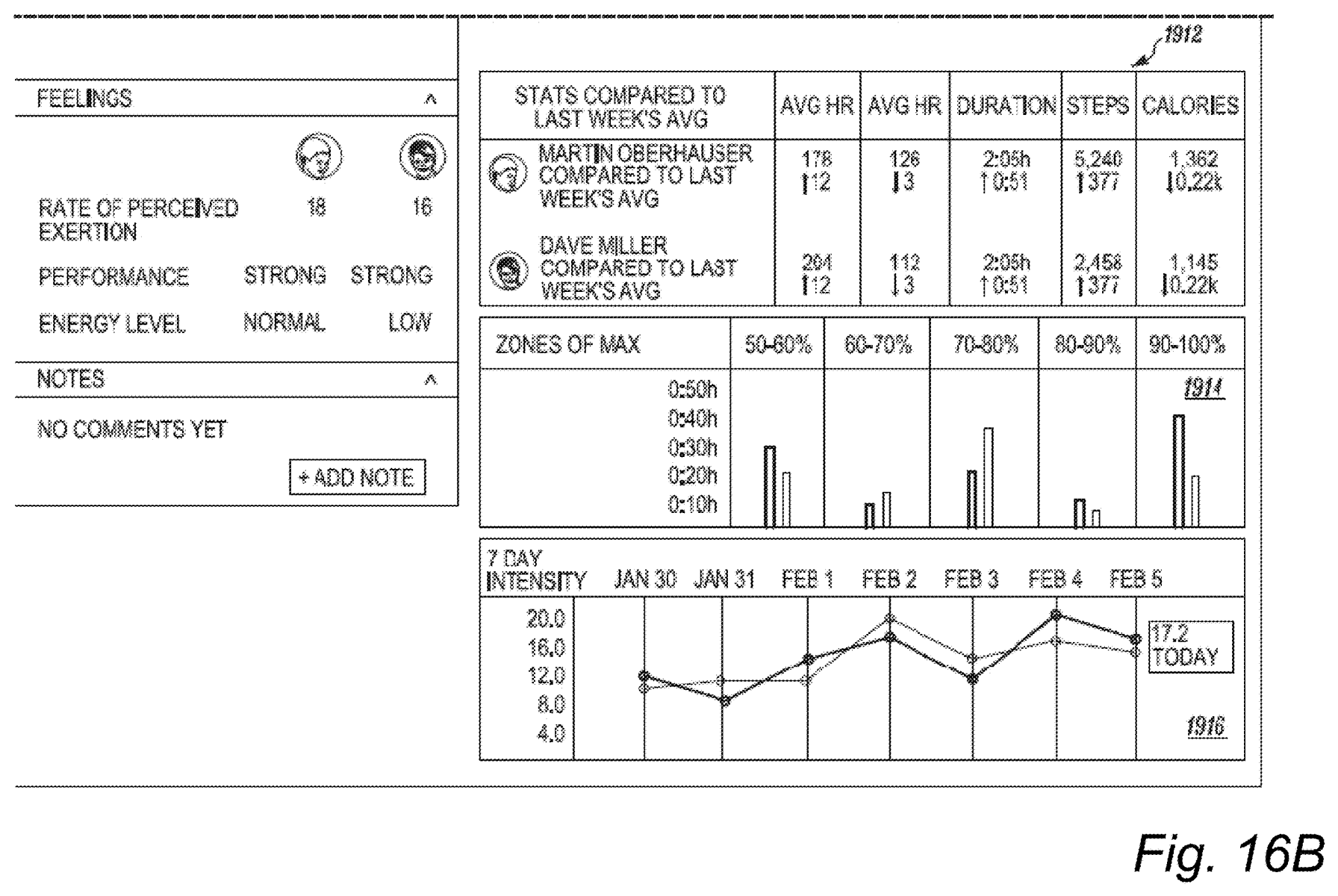

FEELINGS  ∧

RATE OF PERCEIVED EXERTION    19    16

PERFORMANCE    STRONG    STRONG

ENERGY LEVEL    NORMAL    LOW

NOTES    ∧

NO COMMENTS YET

+ ADD NOTE

_1912_

| STATS COMPARED TO LAST WEEK'S AVG | AVG HR | AVG HR | DURATION | STEPS | CALORIES |
|---|---|---|---|---|---|
| MARTIN OBERHAUSER COMPARED TO LAST WEEKS AVG | 178 ↑2 | 126 ↑3 | 2:08h ↑0:51 | 5,240 ↑377 | 1,362 ↓0.22k |
| DAVE MILLER COMPARED TO LAST WEEKS AVG | 204 ↑2 | 112 ↑3 | 2:08h ↑0:51 | 2,458 ↑377 | 1,145 ↓0.22k |

| ZONES OF MAX | 50-60% | 60-70% | 70-80% | 80-90% | 90-100% |
|---|---|---|---|---|---|
| 0:50h | | | | | |
| 0:40h | | | | | |
| 0:30h | | | | | |
| 0:20h | | | | | |
| 0:10h | | | | | |

_1914_

7 DAY INTENSITY    JAN 30    JAN 31    FEB 1    FEB 2    FEB 3    FEB 4    FEB 5

20.0
16.0
12.0
8.0
4.0

172 TODAY

_1916_

DETECTING SLEEP INTENTION

CROSS-REFERENCE TO RELATED APPLICATIONS

This application is a continuation of U.S. patent application Ser. No. 17/117,593 filed on Dec. 10, 2020 (now U.S. Pat. No. 11,925,473), the entire content of which is hereby incorporated by reference.

TECHNICAL FIELD

The present disclosure generally relates to detecting sleep intention using a wearable physiological monitoring device, e.g., to determine whether a wearer is awaking to end a period of sleep or is merely stirring with intentions of returning to sleep.

BACKGROUND

A wearable physiological monitoring device can be used to monitor a wearer when the wearer is sleeping, where data derived from such monitoring can be useful for evaluating the quality of the wearer's sleep. However, many people awaken during a time period in which they intend to be sleeping, where these awakening periods can generally be categorized as either (1) an intent to awaken, or (2) an intent to return to sleep (e.g., where a person is awakened due to general restlessness). However, wearable physiological monitoring devices may be unable to differentiate between the aforementioned categories of awakening periods. Therefore, even when a wearer intends to return to sleep, data from a wearable physiological monitoring device may be processed to evaluate the wearer's sleep period, albeit prematurely. In this manner, processing bandwidth may be wasted on premature evaluations of sleep periods that are ongoing.

There remains a need for improved detection of sleep intention for wearable physiological monitoring devices and systems, e.g., to mitigate the evaluation of sleep periods that have not yet completed.

SUMMARY

A wearable physiological monitoring device is configured to determine a wearer's sleep intention. In particular, the device evaluates activity that might be objectively associated with awaking from sleep in order to distinguish between a wearer's intention to end sleep and transitory stirring or other intermittent activity occurring in the context of a longer sleep interval. By evaluating sleep intention more accurately in this manner, the device can advantageously request sleep analysis from a remote server in those instances where a user intends to end a period of sleep (so that this data can be available to the user more quickly), while avoiding unnecessary or redundant server-side processing of sleep data in those instances where a user intends to continue sleeping.

BRIEF DESCRIPTION OF THE DRAWINGS

The foregoing and other objects, features, and advantages of the devices, systems, and methods described herein will be apparent from the following description of particular embodiments thereof, as illustrated in the accompanying drawings. The drawings are not necessarily to scale, emphasis instead being placed upon illustrating the principles of the devices, systems, and methods described herein. In the drawings, like reference numerals generally identify corresponding elements.

FIG. 6 is a flow chart illustrating a signal processing algorithm for generating a sequence of heart rates for every detected heartbeat that may be embodied in computer-executable instructions stored on one or more non-transitory computer-readable media.

FIG. 7 is a flow chart illustrating a method of determining an intensity score.

FIG. 8 is a flow chart illustrating a method by which a user may use intensity and recovery scores.

Figure 12B:
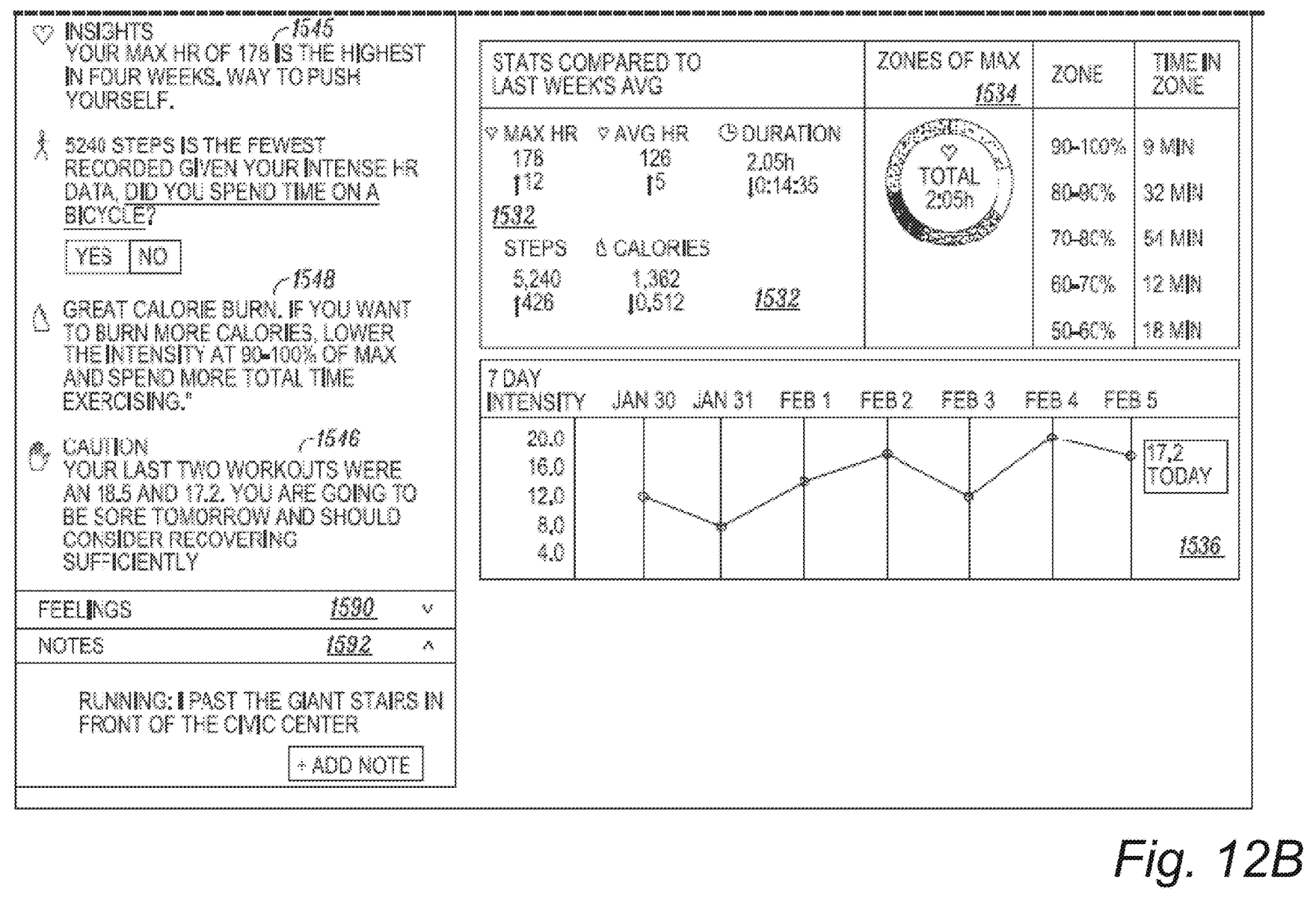

FIG. 12B illustrates part of a user interface for displaying physiological data specific to a user as rendered on visual display device.

FIG. 13B illustrates part of a user interface for displaying physiological data specific to a user as rendered on visual display device.

FIG. 14B illustrates part of a user interface for displaying physiological data specific to a user as rendered on visual display device.

FIG. 15B illustrates part of a user interface for displaying physiological data specific to a user as rendered on visual display device.

FIG. 16B illustrates part of a user interface rendered on a visual display device for displaying physiological data on a plurality of users.

DESCRIPTION

Figure 1:
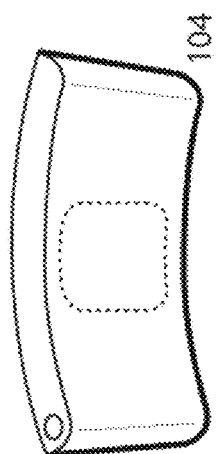
FIG. 1 illustrates front and back perspective views of a wearable system configured as a bracelet including one or more straps.

The embodiments will now be described more fully hereinafter with reference to the accompanying figures, in which preferred embodiments are shown. The foregoing may, however, be embodied in many different forms and should not be construed as limited to the illustrated embodiments set forth herein. Rather, these illustrated embodiments are provided so that this disclosure will convey the scope to those skilled in the art.

All documents mentioned herein are hereby incorporated by reference in their entirety. References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context. Thus, the term "or" should generally be understood to mean "and/or" and so forth.

Recitation of ranges of values herein are not intended to be limiting, referring instead individually to any and all values falling within the range, unless otherwise indicated herein, and each separate value within such a range is incorporated into the specification as if it were individually recited herein. The words "about," "approximately" or the like, when accompanying a numerical value, are to be construed as indicating a deviation as would be appreciated by one of ordinary skill in the art to operate satisfactorily for an intended purpose. Similarly, words of approximation such as "approximately" or "substantially" when used in reference to physical characteristics, should be understood to contemplate a range of deviations that would be appreciated by one of ordinary skill in the art to operate satisfactorily for a corresponding use, function, purpose, or the like. Ranges of values and/or numeric values are provided herein as examples only, and do not constitute a limitation on the scope of the described embodiments. Where ranges of values are provided, they are also intended to include each value within the range as if set forth individually, unless expressly stated to the contrary. The use of any and all examples, or exemplary language ("e.g.," "such as," or the like) provided herein, is intended merely to better describe the embodiments and does not pose a limitation on the scope of the embodiments. No language in the specification should be construed as indicating any unclaimed element as essential to the practice of the embodiments.

In the following description, it is understood that terms such as "first," "second," "top," "bottom," "up," "down," "above," "below," and the like, are words of convenience and are not to be construed as limiting terms unless specifically stated to the contrary.

Exemplary embodiments provide physiological measurement systems, devices and methods for continuous health and fitness monitoring, and provide improvements to overcome the drawbacks of conventional heart rate monitors. One aspect of the present disclosure is directed to providing a lightweight wearable system with a strap that collects various physiological data or signals from a wearer. The strap may be used to position the system on an appendage or extremity of a user, for example, wrist, ankle, and the like. Exemplary systems are wearable and enable real-time and continuous monitoring of heart rate without the need for a chest strap or other bulky equipment which could otherwise cause discomfort and prevent continuous wearing and use. The system may determine the user's heart rate without the use of electrocardiography and without the need for a chest strap. Exemplary systems can thereby be used in not only assessing general well-being but also in continuous monitoring of fitness. Exemplary systems also enable monitoring of one or more physiological parameters in addition to heart rate including, but not limited to, body temperature, heart rate variability, motion, sleep, stress, fitness level, recovery level, effect of a workout routine on health and fitness, caloric expenditure, and the like.

A health or fitness monitor that includes bulky components may hinder continuous wear. Existing fitness monitors often include the functionality of a watch, thereby making the health or fitness monitor quite bulky and inconvenient for continuous wear. Accordingly, one aspect is directed to providing a wearable health or fitness system that does not include bulky components, thereby making the bracelet slimmer, unobtrusive and appropriate for continuous wear. The ability to continuously wear the bracelet further allows continuous collection of physiological data, as well as continuous and more reliable health or fitness monitoring. For example, embodiments of the bracelet disclosed herein allow users to monitor data at all times, not just during a fitness session. In some embodiments, the wearable system may or may not include a display screen for displaying heart rate and other information. In other embodiments, the wearable system may include one or more light emitting diodes (LEDs) to provide feedback to a user and display heart rate selectively. In some embodiments, the wearable system may include a removable or releasable modular head that may provide additional features and may display additional information. Such a modular head can be releasably installed on the wearable system when additional information display is desired, and removed to improve the comfort and appearance of the wearable system. In other embodiments, the head may be integrally formed in the wearable system.

Exemplary embodiments also include computer-executable instructions that, when executed, enable automatic interpretation of one or more physiological parameters to assess the cardiovascular intensity experienced by a user (embodied in an intensity score or indicator) and the user's recovery after physical exertion or daily stress given sleep and other forms of rest (embodied in a recovery score). These indicators or scores may be stored and displayed in a meaningful format to assist a user in managing his health and exercise regimen. Exemplary computer-executable instructions may be provided in a cloud implementation.

Exemplary embodiments also provide a vibrant and interactive online community, in the form of a website, for displaying and sharing physiological data among users. A user of the website may include an individual whose health or fitness is being monitored, such as an individual wearing a wearable system disclosed herein, an athlete, a sports team member, a personal trainer or a coach. In some embodiments, a user may pick his/her own trainer from a list to comment on their performance. Exemplary systems have the ability to stream all physiological information wirelessly, directly or through a mobile communication device application, to an online website using data transfer to a cell phone/computer. This information, as well as any data described herein, may be encrypted (e.g., the data may include encrypted biometric data). Thus, the encrypted data may be streamed to a secure server for processing. In this manner, only authorized users will be able to view the data and any associated scores. In addition, or in the alternative, the website may allow users to monitor their own fitness results, share information with their teammates and coaches, compete with other users, and win status. Both the wearable system and the website allow a user to provide feedback regarding his/her day, exercise and/or sleep, which enables recovery and performance ratings.

In an exemplary technique of data transmission, data collected by a wearable system may be transmitted directly to a cloud-based data storage, from which data may be downloaded for display and analysis on a website. In another exemplary technique of data transmission, data collected by a wearable system may be transmitted via a mobile communication device application to a cloud-based data storage, from which data may be downloaded for display and analysis on a website.

In some embodiments, the website may be a social networking site. In some embodiments, the website may be displayed using a mobile website or a mobile application. In some embodiments, the website may be configured to communicate data to other websites or applications. In some embodiments, the website may be configured to provide an interactive user interface. The website may be configured to display results based on analysis on physiological data received from one or more devices. The website may be configured to provide competitive ways to compare one user to another, and ultimately a more interactive experience for the user. For example, in some embodiments, instead of merely comparing a user's physiological data and performance relative to that user's past performances, the user may be allowed to compete with other users and the user's performance may be compared to that of other users.

Certain terms are defined below to facilitate understanding of exemplary embodiments.

The term "user" as used herein, refers to any type of animal, human or non-human, whose physiological information may be monitored using an exemplary wearable physiological monitoring system.

The term "body," as used herein, refers to the body of a user.

The term "continuous," as used herein in connection with heart rate data collection, refers to collection of heart rate data at a sufficient frequency to enable detection of every heart beat and also refers to collection of heart rate data continuously throughout the day and night.

The term "pointing device," as used herein, refers to any suitable input interface, specifically, a human interface device, that allows a user to input spatial data to a computing system or device. In an exemplary embodiment, the pointing device may allow a user to provide input to the computer using physical gestures, for example, pointing, clicking, dragging, and dropping. Exemplary pointing devices may include, but are not limited to, a mouse, a touchpad, a touchscreen, and the like.

The term "multi-chip module," as used herein, refers to an electronic package in which multiple integrated circuits (IC) are packaged with a unifying substrate, facilitating their use as a single component, i.e., as a higher processing capacity IC packaged in a much smaller volume.

The term "computer-readable medium," as used herein, refers to a non-transitory storage hardware, non-transitory storage device or non-transitory computer system memory that may be accessed by a controller, a microcontroller, a computational system or a module of a computational system to encode thereon computer-executable instructions or software programs. The "computer-readable medium" may be accessed by a computational system or a module of a computational system to retrieve and/or execute the computer-executable instructions or software programs encoded on the medium. The non-transitory computer-readable media may include, but are not limited to, one or more types of hardware memory, non-transitory tangible media (for example, one or more magnetic storage disks, one or more optical disks, one or more USB flash drives), computer system memory or random access memory (such as, DRAM, SRAM, EDO RAM) and the like.

The term "distal," as used herein, refers to a portion, end or component of a physiological measurement system that is farthest from a user's body when worn by the user.

The term "proximal," as used herein, refers to a portion, end or component of a physiological measurement system that is closest to a user's body when worn by the user.

The term "equal," as used herein, refers, in a broad lay sense, to exact equality or approximate equality within some tolerance.

I. Exemplary Wearable Physiological Measurement Systems

Exemplary embodiments provide wearable physiological measurements systems that are configured to provide continuous measurement of heart rate. Exemplary systems are configured to be continuously wearable on an appendage, for example, wrist or ankle, and do not rely on electrocardiography or chest straps in detection of heart rate. The exemplary system includes one or more light emitters for emitting light at one or more desired frequencies toward the user's skin, and one or more light detectors for received light reflected from the user's skin. The light detectors may include a photo-resistor, a photo-transistor, a photo-diode, and the like. As light from the light emitters (for example, green light) pierces through the skin of the user, the blood's natural absorbance or transmittance for the light provides fluctuations in the photo-resistor readouts. These waves have the same frequency as the user's pulse since increased absorbance or transmittance occurs only when the blood flow has increased after a heartbeat. The system includes a processing module implemented in software, hardware or a combination thereof for processing the optical data received at the light detectors and continuously determining the heart rate based on the optical data. The optical data may be combined with data from one or more motion sensors, e.g., accelerometers and/or gyroscopes, to minimize or eliminate noise in the heart rate signal caused by motion or other artifacts (or with other optical data of another wavelength).

Figure 2:
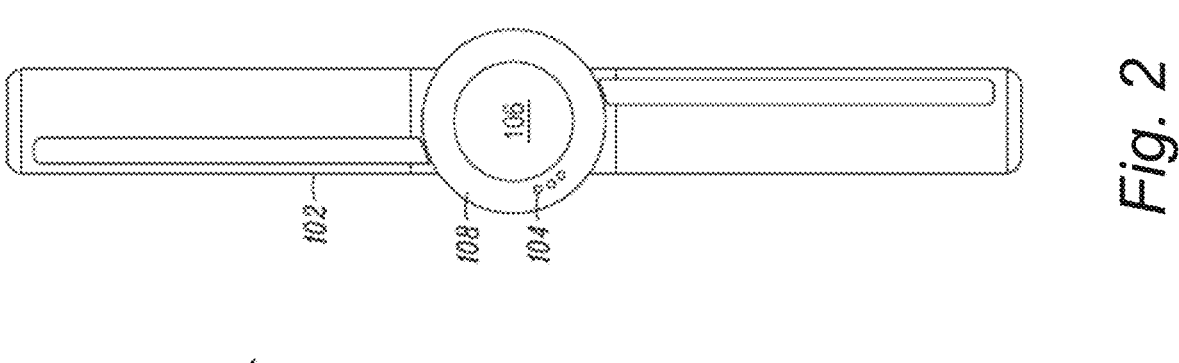
FIG. 2 illustrates a wearable physiological measurement system.

FIG. 1 illustrates front and back perspective views of one embodiment of a wearable system configured as a bracelet 100 including one or more straps 102. FIG. 2 shows another exemplary embodiment of a bracelet according to aspects disclosed herein with an exemplary user interface 106. The bracelet 100 may be sleek and lightweight, thereby making it appropriate for continuous wear. The bracelet 100 may or may not include a display screen, e.g., user interface 106 such as a light emitting diode (LED) display for displaying any desired data (e.g., instantaneous heart rate).

Figure 3:
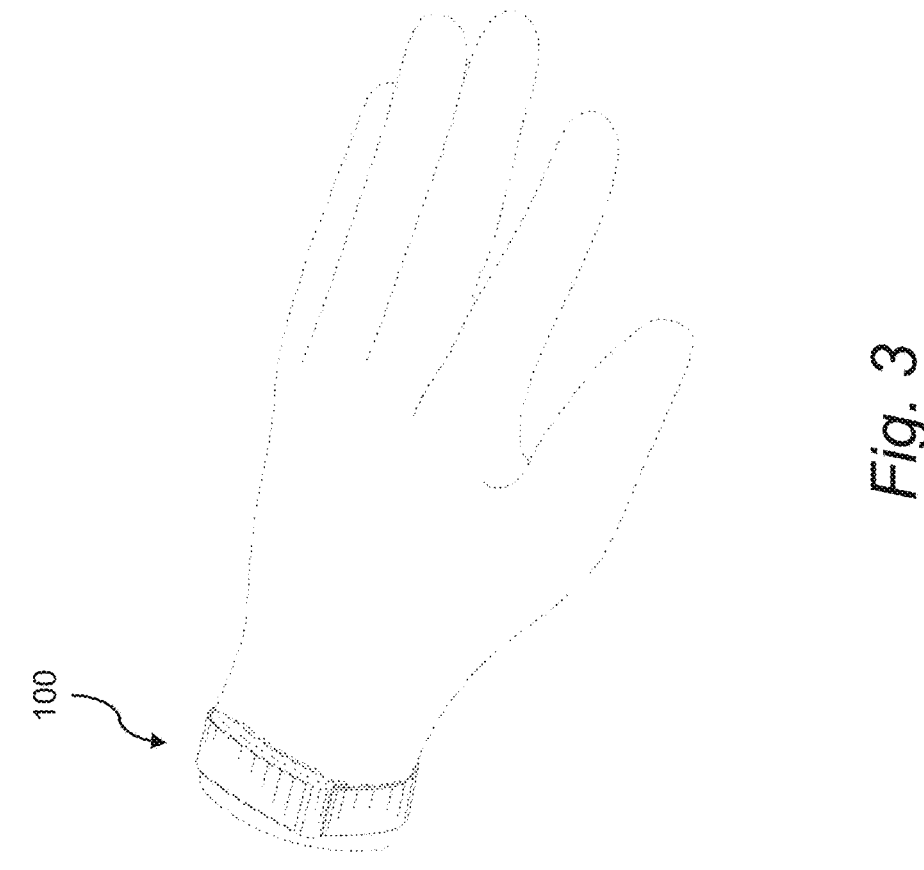
FIG. 3 illustrates placement of a wearable physiological measurement system on a user's wrist.

As shown in the non-limiting embodiment in FIG. 1, the strap 102 of the bracelet 100 may have a wider side and a narrower side. In one embodiment, a user may simply insert the narrower side into the thicker side and squeeze the two together until the strap 102 is tight around the wrist, as shown in FIG. 3. To remove the strap 102, a user may push the strap 102 further inwards, which unlocks the strap 102 and allows it to be released from the wrist. In other embodiments, various other fastening means may be provided. For example, the fastening mechanism may include, without limitation, a clasp, clamp, clip, dock, friction fit, hook and loop, latch, lock, pin, screw, slider, snap, button, spring, yoke, and so on.

In some embodiments, the strap 102 of the bracelet 100 may be a slim elastic band formed of any suitable elastic material, for example, rubber. Certain embodiments of the wearable system may be configured to have one size that fits all. Other embodiments may provide the ability to adjust for different wrist sizes. In one aspect, a combination of constant module strap material, a spring-loaded, floating optical system and a silicon-rubber finish may be used in order to achieve coupling while maintaining the strap's comfort for continuous use. Use of medical-grade materials to avoid skin irritations may be utilized.

As shown in FIG. 1, the wearable system (e.g., the bracelet 100) may include components configured to provide various functions such as data collection and streaming functions of the system. In some embodiments, the wearable system may include a button underneath the wearable system. In some embodiments, the button may be configured such that, when the wearable system is properly tightened to one's wrist, the button may press down and activate the system to begin storing information. In other embodiments, the button may be disposed and configured such that it may be pressed manually at the discretion of a user to begin storing information or otherwise to mark the start or end of an activity period. In some embodiments, the button may be held to initiate a time stamp and held again to end a time stamp, which may be transmitted, directly or through a mobile communication device application, to a website as a time stamp.

Time stamp information may be used, for example, as a privacy setting to indicate periods of activity during which physiological data may not be shared with other users. In one aspect, the button may be tapped, double-tapped (or triple-tapped or more), or held down in order to perform different functions or display different information (e.g., display battery information, generate time stamps, etc.). Other implementations may include more or less buttons or other forms of interfaces. More general, a privacy switch such as any of the user inputs or controls described herein may be operated to control restrictions on sharing, distribution, or use of heart rate or other continuously monitored physiological data. For example, the privacy switch may include a toggle switch to switch between a private setting where data is either not gathered at all or where data is stored locally for a user, and between a public, shared, or other non-private setting where data is communicated over a network and/or to a shared data repository. The privacy switch may also support numerous levels of privacy, e.g., using a hierarchical, role-based, and/or identity-based arrangement of permitted users and/or uses. As another example, various levels of privacy may be available for the type and amount of data that is shared versus private. In general, the privacy switch may be a physical switch on the wearable system, or a logical switch or the like maintained on a computer or other local or mobile computing device of the user, or on a website or other network-accessible resource where the user can select and otherwise control privacy settings for monitored physiological data.

In some embodiments, the wearable system may be waterproof so that users never need to remove it, thereby allowing for continuous wear.

The wearable system may include a heart rate monitor. In one example, the heart rate may be detected from the radial artery, in the exemplary positioning shown in FIG. 3. See, Certified Nursing Association, "Regular monitoring of your patient's radial pulse can help you detect changes in their condition and assist in providing potentially life-saving care." See, http://cnatraininghelp.com/cna-skills/counting-and-recording-a-radial-pulse, the entire contents of which are incorporated herein by reference. Thus, the wearable system may include a pulse sensor. In one embodiment, the wearable system may be configured such that, when a user wears it around their wrist and tightens it, the sensor portion of the wearable system is secured over the user's radial artery or other blood vessel. Secure connection and placement of the pulse sensor over the radial artery or other blood vessel may allow measurement of heart rate and pulse. It will be understood that this configuration is provided by way of example only, and that other sensors, sensor positions, and monitoring techniques may also or instead be employed without departing from the scope of this disclosure.

In some embodiments, the pulse or heart rate may be taken using an optical sensor coupled with one or more light emitting diodes (LEDs), all directly in contact with the user's wrist. The LEDs are provided in a suitable position from which light can be emitted into the user's skin. In one example, the LEDs mounted on a side or top surface of a circuit board in the system to prevent heat buildup on the LEDs and to prevent burns on the skin. The circuit board may be designed with the intent of dissipating heat, e.g., by including thick conductive layers, exposed copper, heatsink, or similar. In one aspect, the pulse repetition frequency is such that the amount of power thermally dissipated by the LED is negligible. Cleverly designed clastic wrist straps can ensure that the sensors are always in contact with the skin and that there is a minimal amount of outside light seeping into the sensors. In addition to the clastic wrist strap, the design of the strap may allow for continuous micro adjustments (no preset sizes) in order to achieve an optimal fit, and a floating sensor module. The sensor module may be free to move with the natural movements caused by flexion and extension of the wrist.

In some embodiments, the wearable system may be configured to record other physiological parameters including, but not limited to, skin temperature (using a thermometer), galvanic skin response (using a galvanic skin response sensor), motion (using one or more multi-axes accelerometers and/or gyroscope), and the like, and environmental or contextual parameters, e.g., ambient temperature, humidity, time of day, and the like. In an implementation, sensors are used to provide at least one of continuous motion detection, environmental temperature sensing, electrodermal activity (EDA) sensing, galvanic skin response (GSR) sensing, and the like. In this manner, an implementation can identify the cause of a detected physiological event. Reflectance PhotoPlethysmoGraphy (RPPG) may be used for the detection of cardiac activity, which may provide for non-intrusive data collection, usability in wet, dusty and otherwise harsh environments, and low power requirements. For example, as explained herein, using the physiological readouts of the device and the analytics described herein, an "Intensity Score" (e.g., 0-21) (e.g., that measures a user's recent exertion), a "Recovery Score" (e.g., 0-100%), and "Sleep Score" (e.g., 0-100) may together measure readiness for physical and psychological exertion.

In some embodiments, the wearable system may further be configured such that a button underneath the system may be pressed against the user's wrist, thus triggering the system to begin one or more of collecting data, calculating metrics and communicating the information to a network. In some embodiments, the sensor used for, e.g., measuring heart rate or GSR or any combination of these, may be used to indicate whether the user is wearing the wearable system or not. In some embodiments, power to the one or more LEDs may be cut off as soon as this situation is detected, and reset once the user has put the wearable system back on their wrist.

The wearable system may include one, two, or more sources of battery life, e.g., two or more batteries. In some embodiments, it may have a battery that can slip in and out of the head of the wearable system and can be recharged using an included accessory. Additionally, the wearable system may have a built-in battery that is less powerful. When the more powerful battery is being charged, the user does not need to remove the wearable system and can still record data (during sleep, for example).

In some embodiments, an application associated with data from an exemplary wearable system (e.g., a mobile communication device application) may include a user input component for enabling additional contextual data, e.g., emotional (e.g., the user's feelings), perceived intensity, and the like. When the data is uploaded from the wearable system directly or indirectly to a website, the website may record a user's "Vibes" alongside their duration of exercise and sleep.

In exemplary embodiments, the wearable system is enabled to automatically detect when the user is asleep, awake but at rest and exercising based on physiological data collected by the system.

As shown in FIG. 2, a rotatable wheel 108 may be provided at the substantial center (or elsewhere) of the wearable system to control whether the system is displaying the heart rate. For example, when the wheel is turned to the right however, the system continuously shows heart rate, and turns off the heart rate display when the wheel is turned to the right again. In one example, turning the wheel to the right and holding it there creates a time stamp to indicate the duration of exercise. Turning the wheel to the left and holding it there forces data transmission to a cell phone, external computer or the Internet. In other embodiments, the wheel 108 may be absent in the wearable system. In some embodiments, the functionality of a rotatable wheel 108 described herein may be provided in an application of a mobile communication device that is associated with physiological data collected from a wearable system.

Figures 4, 5:
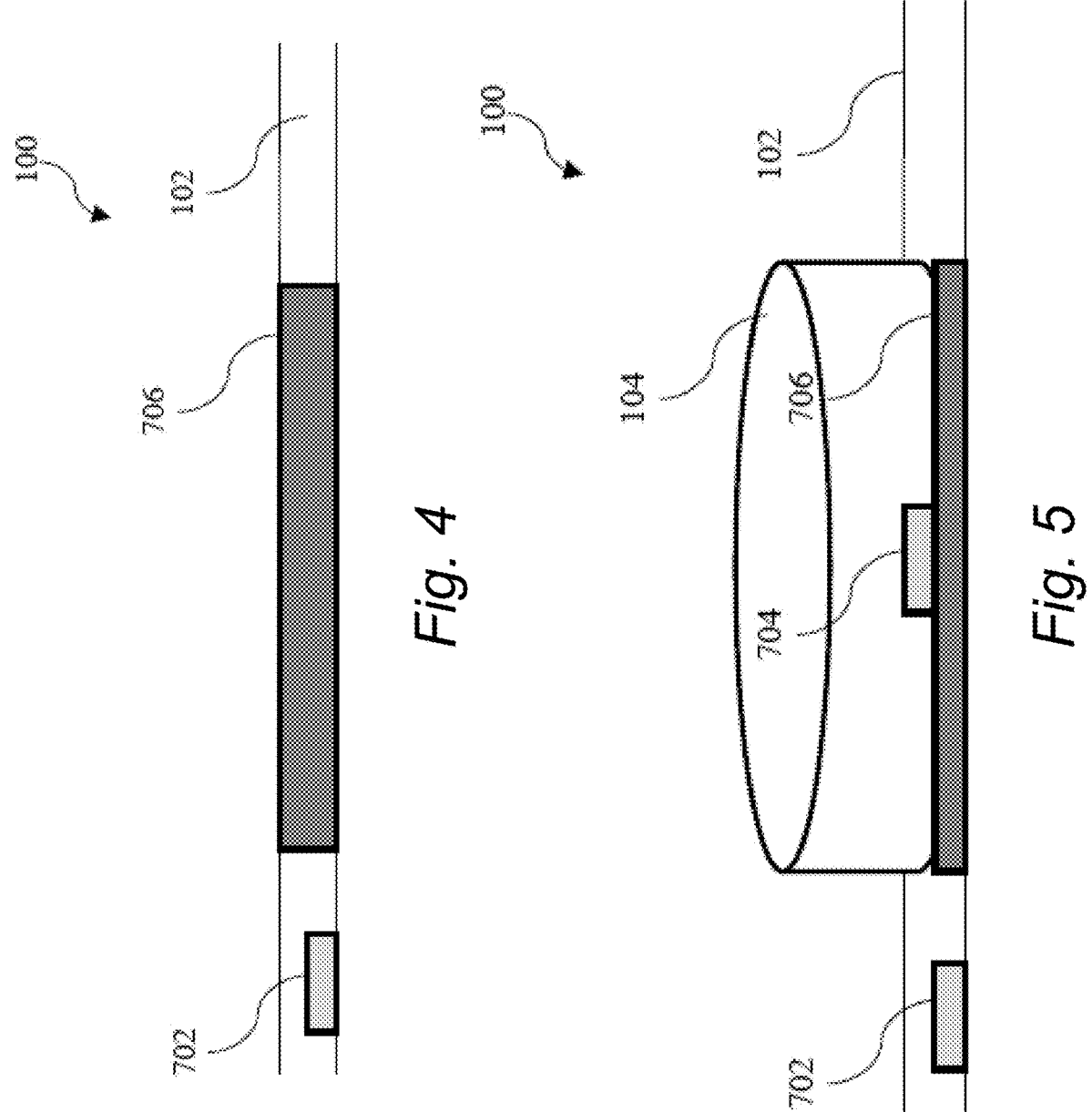
FIG. 4 illustrates a side view of a physiological measurement system including a strap that is not coupled to a modular head portion.
FIG. 5 illustrates a side view of a physiological measurement system in which a modular head portion is removably coupled to the strap.

In some embodiments, a physiological measurement system may be configured in a modular design to enable continuous operation of the system in monitoring physiological information of a user wearing the system. The module design may include a strap and a separate modular head portion or housing that is removably couplable to the strap. FIG. 4 illustrates a side view of an exemplary physiological measurement system 100 including a strap 102 that is not coupled to a modular head portion or housing 104. FIG. 5 illustrates a side view of the system 100 in which the modular head portion 104 is removably coupled to the strap 102.

In the non-limiting illustrative module design, the strap 102 of a physiological measurement system may be provided with a set of components that enables continuous monitoring of at least a heart rate of the user so that it is independent and fully self-sufficient in continuously monitoring the heart rate without requiring the modular head portion 104. In one embodiment, the strap includes a plurality of light emitters for emitting light toward the user's skin, a plurality of light detectors for receiving light reflected from the user's skin, an electronic circuit board comprising a plurality of electronic components configured for analyzing data corresponding to the reflected light to automatically and continually determine a heart rate of the user, and a first set of one or more batteries for supplying electrical power to the light emitters, the light detectors and the electronic circuit board. In some embodiments, the strap may also detect one or more other physiological characteristics of the user including, but not limited to, temperature, galvanic skin response, and the like. The strap may include one or more slots for permanently or removably coupling batteries 702 to the strap 102.

The strap 102 may include an attachment mechanism 706, e.g., a press-fit mechanism, for coupling the modular head portion 104 to the strap 102. The modular head portion 104 may be coupled to the strap 102 at any desired time by the user to impart additional functionality to the system 100. In one embodiment, the modular head portion 104 includes a second set of one or more batteries 704 chargeable by an external power source so that the second set of batteries can be used to charge or recharge the first set of batteries 702 in the strap 102. The combination of the first and second sets of batteries enables the user to continuously monitor his/her physiological information without having to remove the strap for recharging. In some embodiments, the module head portion may include one or more additional components including, but not limited to, an interface 616 including visual display device configured to render a user interface for displaying physiological information of the user, a GPS sensor, an electronic circuit board (e.g., to process GPS signals), and the like.

Certain exemplary systems may be configured to be coupled to any desired part of a user's body so that the system may be moved from one portion of the body (e.g., wrist) to another portion of the body (e.g., ankle) without affecting its function and operation. An exemplary system may include an electronic circuit board comprising a plurality of electronic components configured for analyzing data corresponding to the reflected light to automatically and continually determine a heart rate of the user. The electronic circuit board implements a processing module configured to detect an identity of a portion of the user's body, for example, an appendage like wrist, ankle, to which the strap is coupled based on one or more signals associated with the heart rate of the user, and, based on the identity of the appendage, adjust data analysis of the reflected light to determine the heart rate of the user.

In one embodiment, the identity of the portion of the user's body to which the wearable system is attached may be determined based on one or more parameters including, but not limited to, absorbance level of light as returned from the user's skin, reflectance level of light as returned from the user's skin, motion sensor data (e.g., accelerometer and/or gyroscope), altitude of the wearable system, and the like.

In some embodiments, the processing module is configured to determine that the wearable system is taken off from the user's body. In one example, the processing module may determine that the wearable system has been taken off if data from the galvanic skin response sensor indicates data atypical of a user's skin. If the wearable system is determined to be taken off from the user's body, the processing module is configured to deactivate the light emitters and the light detectors and cease monitoring of the heart rate of the user to conserve power.

In some exemplary embodiments, the electronic components of the physiological measurement system may be provided in the form of a multi-chip module in which a plurality of electrically-coupled electronic circuit boards are provided separately within the system. In one non-limiting example, the processor and random-access memory (RAM) may be provided on a first circuit board, wireless communication components may be provided on a second circuit board, and sensors may be provided on a third circuit board. The separate electronic circuit boards may be provided in a modular head of the system and/or along a strap of the system. The term "multi-chip module," as used herein, refers to an electronic package in which multiple integrated circuits (IC) are packaged with a unifying substrate, facilitating their use as a single component, i.e., as a higher processing capacity IC packaged in a much smaller volume. Each IC can comprise a circuit fabricated in a thinned semiconductor wafer. Any suitable set of one or more electronic components may be provided in the circuit boards of a multi-chip module. Exemplary embodiments also provide methods for fabricating and assembling multi-chip modules as taught herein.

Exemplary numbers of chips integrated in a multi-chip module may include, but are not limited to, two, three, four, five, six, seven, eight, and the like. In one embodiment of a physiological measurement system, a single multi-chip module is provided on a circuit board that performs operations to generate physiological information associated with a user of the system. In other embodiments, a plurality of multi-chip modules are provided on a circuit board of the physiological measurement system. The plurality of multi-chip modules may be stacked vertically on top of one another on the circuit board to further minimize the packaging size and the footprint of the circuit board.

In one multi-chip embodiment, two or more electrically-coupled circuit boards of a multi-chip module may be provided in a physiological measurement system in a vertically stacked manner to minimize the packaging size and the footprint of the circuit board. Vertically stacking the components on a circuit board minimizes the packaging size (e.g., the length and width) and the footprint occupied by the chips on the circuit board. In certain non-limiting embodiments, a circuit board including one or more physiological sensors may be placed closest to, proximal to or in contact with the user's skin, while one or more circuit boards including one or more processors, storage devices, communication components and non-physiological sensors may be provided in vertical layers that are distal to the user's skin.

Exemplary systems include a processing module configured to filter the raw photoplethysmography data received from the light detectors to minimize contributions due to motion, and subsequently process the filtered data to detect peaks in the data that correspond with heart beats of a user. The overall algorithm for detecting heart beats takes as input the analog signals from optical sensors (mV) and accelerometer, and outputs an implied beats per minute (heart rate) of the signal accurate within a few beats per minute as that determined by an electrocardiography machine even during motion.

In one aspect, using multiple LEDs with different wavelengths reacting to movement in different ways can allow for signal recovery with standard signal processing techniques. The availability of accelerometer information can also be used to compensate for coarse movement signal corruption. In order to increase the range of movements that the algorithm can successfully filter out, an aspect utilizes techniques that augment the algorithm already in place. For example, filtering violent movements of the arm during very short periods of time, such as boxing as exercising, may be utilized by the system. By selective sampling and interpolating over these impulses, an aspect can account for more extreme cases of motion. Additionally, an investigation into different LED wavelengths, intensities, and configurations can allow the systems described herein to extract a signal across a wide spectrum of skin types and wrist sizes. In other words, motion filtering algorithms and signal processing techniques may assist in mitigating the risk caused by movement.

FIG. 6 is a flow chart illustrating an exemplary signal processing algorithm for generating a sequence of heart rates for every detected heartbeat that is embodied in computer-executable instructions stored on one or more non-transitory computer-readable media. In step 902, light emitters of a wearable physiological measurement system emit light toward a user's skin. In step 904, light reflected from the user's skin is detected at the light detectors in the system. In step 906, signals or data associated with the reflected light are pre-processed using any suitable technique to facilitate detection of heart beats. In step 908, a processing module of the system executes one or more computer-executable instructions associated with a peak detection algorithm to process data corresponding to the reflected light to detect a plurality of peaks associated with a plurality of beats of the user's heart. In step 910, the processing module determines an RR interval based on the plurality of peaks detected by the peak detection algorithm. In step 912, the processing module determines a confidence level associated with the RR interval.

Based on the confidence level associated with the RR interval estimate, the processing module selects either the peak detection algorithm or a frequency analysis algorithm to process data corresponding to the reflected light to determine the sequence of instantaneous heart rates of the user. The frequency analysis algorithm may process the data corresponding to the reflected light based on the motion of the user detected using, for example, an accelerometer. The processing module may select the peak detection algorithm or the frequency analysis algorithm regardless of a motion status of the user. It is advantageous to use the confidence in the estimate in deciding whether to switch to frequency-based methods as certain frequency-based approaches are unable to obtain accurate RR intervals for heart rate variability analysis. Therefore, an implementation maintains the ability to obtain the RR intervals for as long as possible, even in the case of motion, thereby maximizing the information that can be extracted.

For example, in step 914, it is determined whether the confidence level associated with the RR interval is above (or equal to or above) a threshold. In certain embodiments, the threshold may be predefined, for example, about 50%-90% in some embodiments and about 80% in one non-limiting embodiment. In other embodiments, the threshold may be adaptive, i.e., the threshold may be dynamically and automatically determined based on previous confidence levels. For example, if one or more previous confidence levels were high (i.e., above a certain level), the system may determine that a present confidence level that is relatively low compared to the previous levels is indicative of a less reliable signal. In this case, the threshold may be dynamically adjusted to be higher so that a frequency-based analysis method may be selected to process the less reliable signal.

If the confidence level is above (or equal to or above) the threshold, in step 916, the processing module may use the plurality of peaks to determine an instantaneous heart rate of the user. On the other hand, in step 920, based on a determination that the confidence level associated with the RR interval is equal to or below the predetermined threshold, the processing module may execute one or more computer-executable instructions associated with the frequency analysis algorithm to determine an instantaneous heart rate of the user. The confidence threshold may be dynamically set based on previous confidence levels.

In some embodiments, in steps 918 or 922, the processing module determines a heart rate variability of the user based on the sequence of the instantaneous heart rates/beats.

The system may include a display device configured to render a user interface for displaying the sequence of the instantaneous heart rates of the user, the RR intervals and/or the heart rate variability determined by the processing module. The system may include a storage device configured to store the sequence of the instantaneous heart rates, the RR intervals and/or the heart rate variability determined by the processing module.

In one aspect, the system may switch between different analytical techniques for determining a heart rate such as a statistical technique for detecting a heart rate and a frequency domain technique for detecting a heart rate. These two different modes have different advantages in terms of accuracy, processing efficiency, and information content, and as such may be useful at different times and under different conditions. Rather than selecting one such mode or technique as an attempted optimization, the system may usefully switch back and forth between these differing techniques, or other analytical techniques, using a predetermined criterion. For example, where statistical techniques are used, a confidence level may be determined and used as a threshold for switching to an alternative technique such as a frequency domain technique. The threshold may also or instead depend on historical, subjective, and/or adapted data for a particular user. For example, selection of a threshold may depend on data for a particular user including without limitation subjective information about how a heart rate for a particular user responds to stress, exercise, and so forth. Similarly, the threshold may adapt to changes in fitness of a user, context provided from other sensors of the wearable system, signal noise, and so forth.

An exemplary statistical technique employs probabilistic peak detection. In this technique, a discrete probabilistic step may be set, and a likelihood function may be established as a mixture of a Gaussian random variable and a uniform. The heart of the likelihood function encodes the assumption that with a first probability (p) the peak detection algorithm has produced a reasonable initial estimate, but with a second probability (1-p) it has not. In a subsequent step, Bayes' rule is applied to determine the posterior density on the parameter space, of which the maximum is taken (that is, the argument (parameter) that maximizes the posterior distribution). This value is the estimate for the heart rate. In a subsequent step, the previous two steps are reapplied for the rest of the sample. There is some variance in the signal due to process noise, which is dependent on the length of the interval. This process noise becomes the variance in the Gaussians used for the likelihood function. Then, the estimate is obtained as the maximum a posteriori on the new posterior distribution. A confidence value is recorded for the estimate which, for some precision measurement, the posterior value is summed at points in the parameter space centered at our estimate +/- the precision.

The beats per minute (BPM) parameter space, $\theta$, may range between about 20 and about 240, corresponding to the empirical bounds on human heart rates. In an exemplary method, a probability distribution is calculated over this parameter space, at each step declaring the mode of the distribution to be the heart rate estimate. A discrete uniform prior may be set:

$$\pi_1 \sim DiscUnit(\theta)$$

The un-normalized, univariate likelihood is defined by a mixture of a Gaussian function and a uniform:

$$l_1 \sim IG + (1-I)U, \, G \sim N\left(\gamma_1\sigma^2\right), I \sim Ber(p)$$

where $$U \sim DiscUnif(\theta)$$

and where $\sigma$ and p are predetermined constants.

Bayes' rule is applied to determine the posterior density on $\theta$, for example, by component-wise multiplying the prior density vector $(\pi_1(\theta))_{\theta \in \theta}$ with the likelihood vector $(l_1(\theta))_{\theta \in \theta}$ to obtain the posterior distribution $\eta_1$. Then, the following is set:

$$\beta_1 = \mathrm{argmax}_{\theta \in \theta}\eta_1(\theta)$$

For $k \geq 2$, the variance in signal S(t) due to process noise is determined. Then, the following variable is set to imbue temporally long RR intervals with more process/interpeak noise and set the post-normalization convolution:

$$\pi_k = \eta_{k-1} * f_{N\left(o,\lambda_k^2\right)|\theta}$$

where $f$ is a density function of the following:

$$Z \sim N\left(o, \lambda_k^2\right)$$

Then, the following expressions are calculated:

$$l_k \sim pG_k + (1-p)U, \; G_k \sim N(\lambda k, \sigma^2)$$

The expression is then normalized and recorded:

$$\beta_k = \operatorname{argmax}_{\theta \in \Theta} \eta_k(\theta)$$

Finally, the confidence level of the above expression for a particular precision threshold is determined:

$$C_k = \Sigma_{\theta \in [\beta_k - e_1, \beta_k + e] \cap \theta} \eta_k.$$

An exemplary frequency analysis algorithm used in an implementation isolates the highest frequency components of the optical data, checks for harmonics common in both the accelerometer data and the optical data, and performs filtering of the optical data. The algorithm takes as input raw analog signals from the accelerometer (3-axis) and pulse sensors, and outputs heart rate values or beats per minute (BPM) for a given period of time related to the window of the spectrogram.

The isolation of the highest frequency components is performed in a plurality of stages, gradually winnowing the window-sizes of consideration, thereby narrowing the range of errors. In one implementation, a spectrogram of $2\hat{}15$ samples with overlap $2\hat{}13$ samples of the optical data is generated. The spectrogram is restricted to frequencies in which heart rate can lie. These restriction boundaries may be updated when smaller window sizes are considered. The frequency estimate is extracted from the spectrogram by identifying the most prominent frequency component of the spectrogram for the optical data. The frequency may be extracted using the following exemplary steps. The most prominent frequency of the spectrogram is identified in the signal. It is determined if the frequency estimate is a harmonic of the true frequency. The frequency estimate is replaced with the true frequency if the estimate is a harmonic of the true frequency. It is determined if the current frequency estimate is a harmonic of the motion sensor data. The frequency estimate is replaced with a previous temporal estimate if it is a harmonic of the motion sensor data. The upper and lower bounds on the frequency obtained are saved. A constant value may be added or subtracted in some cases. In subsequent steps, the constant added or subtracted may be reduced to provide narrower searches. A number of the previous steps are repeated one or more times, e.g., three times, except taking $2\hat{}\{15-i\}$ samples for the window size and $2\hat{}\{13-i\}$ for the overlap in the spectrogram where i is the current number of iteration. The final output is the average of the final symmetric endpoints of the frequency estimation.

The table below demonstrates the performance of the algorithm disclosed herein. To arrive at the results below, experiments were conducted in which a subject wore an exemplary wearable physiological measurement system and a 3-lead ECG which were both wired to the same microcontroller (e.g., Arduino) in order to provide time-synced data. Approximately 50 data sets were analyzed which included the subject standing still, walking, and running on a treadmill.

TABLE 1

| Performance of signal processing algorithm disclosed herein | | |
| --- | --- | --- |
| | Clean data error (mean, std) in BPM | Noisy data error (mean, std) in BPM |
| 4-level spectrogram (80 second blocks) | 0.2, 2.3 | 0.8, 5.1 |

The algorithm's performance comes from a combination of a probabilistic and frequency based approach. The three difficulties in creating algorithms for heart rate calculations from the PPG data are 1) false detections of beats, 2) missed detections of real beats, and 3) errors in the precise timing of the beat detection. The algorithms disclosed herein provide improvements in these three sources of error and, in some cases, the error is bound to within 2 BPM of ECG values at all times even during the most motion intense activities.

The exemplary wearable system computes heart rate variability (HRV) to obtain an understanding of the recovery status of the body. These values are captured right before a user awakes or when the user is not moving, in both cases photoplethysmography (PPG) variability yielding equivalence to the ECG HRV. HRV is traditionally measured using an ECG machine and obtaining a time series of R-R intervals. Because an exemplary wearable system utilizes photoplethysmography (PPG), it does not obtain the electric signature from the heart beats; instead, the peaks in the obtained signal correspond to arterial blood volume. At rest, these peaks are directly correlated with cardiac cycles, which enables the calculation of HRV via analyzing peak-to-peak intervals (the PPG analog of RR intervals). It has been demonstrated in the medical literature that these peak-to-peak intervals, the "PPG variability," is identical to ECG HRV while at rest. See, Charlot K, et al. "Interchangeability between heart rate and photoplethysmography variabilities during sympathetic stimulations." *Physiological Measurement.* 2009 December; 30(12): 1357-69. doi: 10.1088/0967-3334/30/12/005. URL: http://www.ncbi.nlm.nih.gov/pubmed/19864707; and Lu, S, et. al. "Can photoplethysmography variability serve as an alternative approach to obtain heart rate variability information?" *Journal of Clinical Monitoring and Computing.* 2008 February; 22(1):23-9. URL: http://www.ncbi.nlm.nih.gov/pubmed/17987395, the entire contents of which are incorporated herein by reference.

Exemplary physiological measurement systems are configured to minimize power consumption so that the systems may be worn continuously without requiring power recharging at frequent intervals. The majority of current draw in an exemplary system is allocated to power the light emitters, e.g., LEDs, the wireless transceiver, the microcontroller and peripherals. In one embodiment, the circuit board of the system may include a boost converter that runs a current of about 10 mA through each of the light emitters with an efficiency of about 80% and may draw power directly from the batteries at substantially constant power. With exemplary batteries at about 3.7 V, the current draw from the battery may be about 40 mW. In some embodiments, the wireless transceiver may draw about 10-20 mA of current when it is actively transferring data. In some embodiments, the microcontroller and peripherals may draw about 5 mA of current.

An exemplary system may include a processing module that is configured to automatically adjust one or more operational characteristics of the light emitters and/or the light detectors to minimize power consumption while ensuring that all heart beats of the user are reliably and continuously detected. The operational characteristics may include, but are not limited to, a frequency of light emitted by the light emitters, the number of light emitters activated, a duty cycle of the light emitters, a brightness of the light emitters, a sampling rate of the light detectors, and the like.

The processing module may adjust the operational characteristics based on one or more signals or indicators obtained or derived from one or more sensors in the system including, but not limited to, a motion status of the user, a sleep status of the user, historical information on the user's physiological and/or habits, an environmental or contextual condition (e.g., ambient light conditions), a physical characteristic of the user (e.g., the optical characteristics of the user's skin), and the like.

In one embodiment, the processing module may receive data on the motion of the user using, for example, an accelerometer. The processing module may process the motion data to determine a motion status of the user which indicates the level of motion of the user, for example, exercise, light motion (e.g., walking), no motion or rest, sleep, and the like. The processing module may adjust the duty cycle of one or more light emitters and the corresponding sampling rate of the one or more light detectors based on the motion status. For example, upon determining that the motion status indicates that the user is at a first higher level of motion, the processing module may activate the light emitters at a first higher duty cycle and sample the reflected light using light detectors sampling at a first higher sampling rate. Upon determining that the motion status indicates that the user is at a second lower level of motion, the processing module may activate the light emitters at a second lower duty cycle and sample the reflected light using light detectors sampling at a second lower sampling rate. That is, the duty cycle of the light emitters and the corresponding sampling rate of the light detectors may be adjusted in a graduated or continuous manner based on the motion status or level of motion of the user. This adjustment ensures that heart rate data is detected at a sufficiently high frequency during motion to reliably detect all of the heart beats of the user.

In non-limiting examples, the light emitters may be activated at a duty cycle ranging from about 1% to about 100%. In another example, the light emitters may be activated at a duty cycle ranging from about 20% to about 50% to minimize power consumption. Certain exemplary sampling rates of the light detectors may range from about 50 Hz to about 1000 Hz, but are not limited to these exemplary rates. Certain non-limiting sampling rates are, for example, about 100 Hz, 200 Hz, 500 Hz, and the like.

In one non-limiting example, the light detectors may sample continuously when the user is performing an exercise routine so that the error standard deviation is kept within 5 beats per minute (BPM). When the user is at rest, the light detectors may be activated for about a 1% duty cycle-10 milliseconds each second (i.e., 1% of the time) so that the error standard deviation is kept within 5 BPM (including an error standard deviation in the heart rate measurement of 2 BPM and an error standard deviation in the heart rate changes between measurement of 3 BPM). When the user is in light motion (e.g., walking), the light detectors may be activated for about a 10% duty cycle-100 milliseconds each second (i.e., 10% of the time) so that the error standard deviation is kept within 6 BPM (including an error standard deviation in the heart rate measurement of 2 BPM and an error standard deviation in the heart rate changes between measurement of 4 BPM).

The processing module may adjust the brightness of one or more light emitters by adjusting the current supplied to the light emitters. For example, a first level of brightness may be set by current ranging between about 1 mA to about 10 mA, but is not limited to this exemplary range. A second higher level of brightness may be set by current ranging from about 11 mA to about 30 mA, but is not limited to this exemplary range. A third higher level of brightness may be set by current ranging from about 80 mA to about 120 mA, but is not limited to this exemplary range. In one non-limiting example, first, second and third levels of brightness may be set by current of about 5 mA, about 20 mA and about 100 mA, respectively.

In some embodiments, the processing module may detect an environmental or contextual condition (e.g., level of ambient light) and adjust the brightness of the light emitters accordingly to ensure that the light detectors reliably detect light reflected from the user's skin while minimizing power consumption. For example, if it is determined that the ambient light is at a first higher level, the brightness of the light emitters may be set at a first higher level. If it is determined that the ambient light is at a second lower level, the brightness of the light emitters may be set at a second lower level. In some cases, the brightness may be adjusted in a continuous manner based on the detected environment condition.

In some embodiments, the processing module may detect a physiological condition of the user (e.g., an optical characteristic of the user's skin) and adjust the brightness of the light emitters accordingly to ensure that the light detectors reliably detect light reflected from the user's skin while minimizing power consumption. For example, if it is determined that the user's skin is highly reflective, the brightness of the light emitters may be set at a first lower level. If it is determined that the user's skin is not very reflective, the brightness of the light emitters may be set at a second higher level.

Shorter-wavelength LEDs may require more power than is required by longer-wavelength LEDs. Therefore, an exemplary wearable system may provide and use light emitted at two or more different frequencies based on the level of motion detected in order to save battery life. For example, upon determining that the motion status indicates that the user is at a first higher level of motion (e.g., exercising), one or more light emitters may be activated to emit light at a first wavelength. Upon determining that the motion status indicates that the user is at a second lower level of motion (e.g., at rest), one or more light emitters may be activated to emit light at a second wavelength that is longer than the first wavelength. Upon determining that the motion status indicates that the user is at a third lower level of motion (e.g., sleeping), one or more light emitters may be activated to emit light at a third wavelength that is longer than the first and second wavelengths. Other levels of motion may be predetermined and corresponding wavelengths of emitted light may be selected. The threshold levels of motion that trigger adjustment of the light wavelength may be based on one or more factors including, but are not limited to, skin properties, ambient light conditions, and the like. Any suitable combination of light wavelengths may be selected, for example, green (for a higher level of motion)/red (for a lower level of motion); red (for a higher level of motion)/infrared (for a lower level of motion); blue (for a higher level of motion)/green (for a lower level of motion); and the like.

Shorter-wavelength LEDs may require more power than is required by other types of heart rate sensors, such as, a piezo-sensor or an infrared sensor. Therefore, an exemplary wearable system may provide and use a unique combination of sensors-one or more light detectors for periods where motion is expected and one or more piezo and/or infrared sensors for low motion periods (e.g., sleep)—to save battery life. Certain other embodiments of a wearable system may exclude piezo-sensors and/or infrared sensors.

For example, upon determining that the motion status indicates that the user is at a first higher level of motion (e.g., exercising), one or more light emitters may be activated to emit light at a first wavelength. Upon determining that the motion status indicates that the user is at a second lower level of motion (e.g., at rest), non-light based sensors may be activated. The threshold levels of motion that trigger adjustment of the type of sensor may be based on one or more factors including, but are not limited to, skin properties, ambient light conditions, and the like.

The system may determine the type of sensor to use at a given time based on the level of motion (e.g., via an accelerometer) and whether the user is asleep (e.g., based on movement input, skin temperature and heart rate). Based on a combination of these factors the system selectively chooses which type of sensor to use in monitoring the heart rate of the user. Common symptoms of being asleep are periods of no movement or small bursts of movement (such as shifting in bed), lower skin temperature (although it is not a dramatic drop from normal), drastic GSR changes, and heart rate that is below the typical resting heart rate when the user is awake. These variables depend on the physiology of a person and thus a machine learning algorithm is trained with user-specific input to determine when he/she is awake/asleep and determine from that the exact parameters that cause the algorithm to deem someone asleep.

In an exemplary configuration, the light detectors may be positioned on the underside of the wearable system and all of the heart rate sensors may be positioned adjacent to each other. For example, the low power sensor(s) may be adjacent to the high power sensor(s) as the sensors may be chosen and placed where the strongest signal occurs. In one example configuration, a 3-axis accelerometer may be used that is located on the top part of the wearable system.

In some embodiments, the processing module may be configured to automatically adjust a rate at which data is transmitted by the wireless transmitter to minimize power consumption while ensuring that raw and processed data generated by the system is reliably transmitted to external computing devices. In one embodiment, the processing module determines an amount of data to be transmitted (e.g., based on the amount of data generated since the time of the last data transmission), and may select the next data transmission time based on the amount of data to be transmitted. For example, if it is determined that the amount of data exceeds (or is equal to or greater than) a threshold level, the processing module may transmit the data or may schedule a time for transmitting the data. On the other hand, if it is determined that the amount of data does not exceed (or is equal to or lower than) the threshold level, the processing module may postpone data transmission to minimize power consumption by the transmitter. In one non-limiting example, the threshold may be set to the amount of data that may be sent in two seconds under current conditions. Exemplary data transmission rates may range from about 50 kbytes per second to about 1 MByte per second, but are not limiting to this exemplary range.

In some embodiments, an operational characteristic of the microprocessor may be automatically adjusted to minimize power consumption. This adjustment may be based on a level of motion of the user's body.

More generally, the above description contemplates a variety of techniques for sensing conditions relating to heart rate monitoring or related physiological activity either directly (e.g., confidence levels or accuracy of calculated heart rate) or indirectly (e.g., motion detection, temperature). However measured, these sensed conditions can be used to intelligently select from among a number of different modes, including hardware modes, software modes, and combinations of the foregoing, for monitoring heart rate based on, e.g., accuracy, power usage, detected activity states, and so forth. Thus there is disclosed herein techniques for selecting from among two or more different heart rate monitoring modes according to a sensed condition.

II. Exemplary Physiological Analytics System

Exemplary embodiments provide an analytics system for providing qualitative and quantitative monitoring of a user's body, health and physical training. The analytics system is implemented in computer-executable instructions encoded on one or more non-transitory computer-readable media. The analytics system relies on and uses continuous data on one or more physiological parameters including, but not limited to, heart rate. The continuous data used by the analytics system may be obtained or derived from an exemplary physiological measurement system disclosed herein, or may be obtained or derived from a derived source or system, for example, a database of physiological data. In some embodiments, the analytics system computes, stores and displays one or more indicators or scores relating to the user's body, health and physical training including, but not limited to, an intensity score and a recovery score. The scores may be updated in real-time and continuously or at specific time periods, for example, the recovery score may be determined every morning upon waking up, the intensity score may be determined in real-time or after a workout routine or for an entire day.

In certain exemplary embodiments, a fitness score may be automatically determined based on the physiological data of two or more users of exemplary wearable systems.

An intensity score or indicator provides an accurate indication of the cardiovascular intensities experienced by the user during a portion of a day, during the entire day or during any desired period of time (e.g., during a week or month). The intensity score is customized and adapted for the unique physiological properties of the user and takes into account, for example, the user's age, gender, anaerobic threshold, resting heart rate, maximum heart rate, and the like. If determined for an exercise routine, the intensity score provides an indication of the cardiovascular intensities experienced by the user continuously throughout the routine. If determined for a period of including and beyond an exercise routine, the intensity score provides an indication of the cardiovascular intensities experienced by the user during the routine and also the activities the user performed after the routine (e.g., resting on the couch, active day of shopping) that may affect their recovery or exercise readiness.

In exemplary embodiments, the intensity score is calculated based on the user's heart rate reserve (HRR) as detected continuously throughout the desired time period, for example, throughout the entire day. In one embodiment, the intensity score is an integral sum of the weighted HRR detected continuously throughout the desired time period. FIG. 7 is a flow chart illustrating an exemplary method of determining an intensity score.

In step 1002, continuous heart rate readings are converted to HRR values. A time series of heart rate data used in step 1002 may be denoted as:

$$H \in T$$

A time series of HRR measurements, v(t), may be defined in the following expression in which MHR is the maximum heart rate and RHR is the resting heart rate of the user:

$$v(t) = \frac{H(t) - RHR}{MHR - RHR}$$

In step 1004, the HRR values are weighted according to a suitable weighting scheme. Cardiovascular intensity, indicated by an intensity score, is defined in the following expression in which w is a weighting function of the HRR measurements:

$$I(t_o, t_1) = \int_{t_0}^{t_1} w(v(t))dt$$

In step 1006, the weighted time series of HRR values is summed and normalized.

$$I_t = \int_T w(v(t))dt \le w(1)|T|$$

Thus, the weighted sum is normalized to the unit interval, i.e., [0, 1]:

$$N_T = \frac{I_T}{w(1) \cdot 24 \text{ hr}}$$

In step 1008, the summed and normalized values are scaled to generate user-friendly intensity score values. That is, the unit interval is transformed to have any desired distribution in a scale (e.g., a scale including 21 points from 0 to 21), for example, arctangent, sigmoid, sinusoidal, and the like. In certain distributions, the intensity values increase at a linear rate along the scale, and in others, at the highest ranges the intensity values increase at more than a linear rate to indicate that it is more difficult to climb in the scale toward the extreme end of the scale. In some embodiments, the raw intensity scores are scaled by fitting a curve to a selected group of "canonical" exercise routines that are predefined to have particular intensity scores.

In one embodiment, monotonic transformations of the unit interval are achieved to transform the raw HRR values to user-friendly intensity scores. An exemplary scaling scheme, expressed as ƒ: [0, 1]→[0, 1], is performed using the following function:

$$(x, N, p) = 0.5\left(\frac{\arctan(N(x - p))}{\pi/2} + 1\right)$$

To generate an intensity score, the resulting value may be multiplied by a number based on the desired scale of the intensity score. For example, if the intensity score is graduated from zero to 21, then the value may be multiplied by 21.

In step 1010, the intensity score values are stored on a non-transitory storage medium for retrieval, display and usage. In step 1012, the intensity score values are, in some embodiments, displayed on a user interface rendered on a visual display device. The intensity score values may be displayed as numbers and/or with the aid of graphical tools, e.g., a graphical display of the scale of intensity scores with current score, and the like. In some embodiments, the intensity score may be indicated by audio. In step 1012, the intensity score values are, in some embodiments, displayed along with one or more quantitative or qualitative pieces of information on the user including, but not limited to, whether the user has exceeded his/her anaerobic threshold, the heart rate zones experienced by the user during an exercise routine, how difficult an exercise routine was in the context of the user's training, the user's perceived exertion during an exercise routine, whether the exercise regimen of the user should be automatically adjusted (e.g., made easier if the intensity scores are consistently high), whether the user is likely to experience soreness the next day and the level of expected soreness, characteristics of the exercise routine (e.g., how difficult it was for the user, whether the exercise was in bursts or activity, whether the exercise was tapering, etc.), and the like. In one embodiment, the analytics system may automatically generate, store and display an exercise regimen customized based on the intensity scores of the user.

Step 1006 may use any of a number of exemplary static or dynamic weighting schemes that enable the intensity score to be customized and adapted for the unique physiological properties of the user. In one exemplary static weighting scheme, the weights applied to the HRR values are based on static models of a physiological process. The human body employs different sources of energy with varying efficiencies and advantages at different HRR levels. For example, at the anaerobic threshold (AT), the body shifts to anaerobic respiration in which the cells produce two adenosine triphosphate (ATP) molecules per glucose molecule, as opposed to 36 at lower HRR levels. At even higher HRR levels, there is a further subsequent threshold (CPT) at which creatine triphosphate (CTP) is employed for respiration with even less efficiency.

In order to account for the differing levels of cardiovascular exertion and efficiency at the different HRR levels, in one embodiment, the possible values of HRR are divided into a plurality of categories, sections or levels (e.g., three) dependent on the efficiency of cellular respiration at the respective categories. The HRR parameter range may be divided in any suitable manner, such as, piecewise, including piecewise-linear, piecewise-exponential, and the like. An exemplary piecewise-linear division of the HRR parameter range enables weighting each category with strictly increasing values. This scheme captures an accurate indication of the cardiovascular intensity experienced by the user because it is more difficult to spend time at higher HRR values, which suggests that the weighting function should increase at the increasing weight categories.

In one non-limiting example, the HRR parameter range may be considered a range from zero (0) to one (1) and divided into categories with strictly increasing weights. In one example, the HRR parameter range may be divided into a first category of a zero HRR value and may assign this category a weight of zero; a second category of HRR values falling between zero (0) and the user's anaerobic threshold (AT) and may assign this category a weight of one (1); a third category of HRR values falling between the user's anaerobic threshold (AT) and a threshold at which the user's body employs creatine triphosphate for respiration (CPT) and may assign this category a weight of 18; and a fourth category of HRR values falling between the creatine triphosphate threshold (CPT) and one (1) and may assign this category a weight of 42, although other numbers of HRR categories and different weight values are possible. That is, in this example, the weights are defined as:

$$w(v) = \begin{cases} 0 & : v = 0 \\ 1 & : v \in (0, AT] \\ 18 & : v \in (AT, CPT] \\ 42 & : v \in (CPT, 1] \end{cases}$$

In another exemplary embodiment of the weighting scheme, the HRR time series is weighted iteratively based on the intensity scores determined thus far (e.g., the intensity score accrued thus far) and the path taken by the HRR values to get to the present intensity score. The path may be detected automatically based on the historical HRR values and may indicate, for example, whether the user is performing high intensity interval training (during which the intensity scores are rapidly rising and falling), whether the user is taking long breaks between bursts of exercise (during which the intensity scores are rising after longer periods), and the like. The path may be used to dynamically determine and adjust the weights applied to the HRR values. For example, in the case of high intensity interval training, the weights applied may be higher than in the case of a more traditional exercise routine.

In another exemplary embodiment of the weighting scheme, a predictive approach is used by modeling the weights or coefficients to be the coefficient estimates of a logistic regression model. In this scheme, a training data set is obtained by continuously detecting the heart rate time series and other personal parameters of a group of individuals. The training data set is used to train a machine learning system to predict the cardiovascular intensities experienced by the individuals based on the heart rate and other personal data. The trained system models a regression in which the coefficient estimates correspond to the weights or coefficients of the weighting scheme. In the training phase, user input on perceived exertion and the intensity scores are compared. The learning algorithm also alters the weighs based on the improving or declining health of a user as well as their qualitative feedback. This yields a unique algorithm that incorporates physiology, qualitative feedback, and quantitative data. In determining a weighting scheme for a specific user, the trained machine learning system is run by executing computer-executable instructions encoded on one or more non-transitory computer-readable media, and generates the coefficient estimates which are then used to weight the user's HRR time series.

One of ordinary skill in the art will recognize that two or more aspects of any of the disclosed weighting schemes may be applied separately or in combination in an exemplary method for determining an intensity score.

In one aspect, heart rate zones quantify the intensity of workouts by weighing and comparing different levels of heart activity as percentages of maximum heart rate. Analysis of the amount of time an individual spends training at a certain percentage of his/her MHR may reveal his/her state of physical exertion during a workout. This intensity, developed from the heart rate zone analysis, motion, and activity, may then indicate his/her need for rest and recovery after the workout, e.g., to minimize delayed onset muscle soreness (DOMS) and prepare him/her for further activity. As discussed above, MHR, heart rate zones, time spent above the anaerobic threshold, and HRV in RSA (Respiratory Sinus Arrhythmia) regions—as well as personal information (gender, age, height, weight, etc.) may be utilized in data processing.

A recovery score or indicator provides an accurate indication of the level of recovery of a user's body and health after a period of physical exertion. The human autonomic nervous system controls the involuntary aspects of the body's physiology and is typically subdivided into two branches: parasympathetic (deactivating) and sympathetic (activating). Heart rate variability (HRV), i.e., the fluctuation in inter-heartbeat interval time, is a commonly studied result of the interplay between these two competing branches. Parasympathetic activation reflects inputs from internal organs, causing a decrease in heart rate. Sympathetic activation increases in response to stress, exercise and disease, causing an increase in heart rate. For example, when high intensity exercise takes place, the sympathetic response to the exercise persists long after the completion of the exercise. When high intensity exercise is followed by insufficient recovery, this imbalance lasts typically until the next morning, resulting in a low morning HRV. This result should be taken as a warning sign as it indicates that the parasympathetic system was suppressed throughout the night. While suppressed, normal repair and maintenance processes that ordinarily would occur during sleep were suppressed as well. Suppression of the normal repair and maintenance processes results in an unprepared state for the next day, making subsequent exercise attempts more challenging.

The recovery score is customized and adapted for the unique physiological properties of the user and takes into account, for example, the user's heart rate variability (HRV), resting heart rate, sleep quality and recent physiological strain (indicated, in one example, by the intensity score of the user). In one exemplary embodiment, the recovery score is a weighted combination of the user's heart rate variability (HRV), resting heart rate, sleep quality indicated by a sleep score, and recent strain (indicated, in one example, by the intensity score of the user). In an exemplar, the sleep score combined with performance readiness measures (such as, morning heart rate and morning heart rate variability) provides a complete overview of recovery to the user. By considering sleep and HRV alone or in combination, the user can understand how exercise-ready he/she is each day and to understand how he/she arrived at the exercise-readiness score each day, for example, whether a low exercise-readiness score is a predictor of poor recovery habits or an inappropriate training schedule. This insight aids the user in adjusting his/her daily activities, exercise regimen and sleeping schedule therefore obtain the most out of his/her training.

In some cases, the recovery score may take into account perceived psychological strain experienced by the user. In some cases, perceived psychological strain may be detected from user input via, for example, a questionnaire on a mobile device or web application. In other cases, psychological strain may be determined automatically by detecting changes in sympathetic activation based on one or more parameters including, but not limited to, heart rate variability, heart rate, galvanic skin response, and the like.

With regard to the user's HRV used in determining the recovery score, suitable techniques for analyzing HRV include, but are not limited to, time-domain methods, frequency-domain methods, geometric methods and non-linear methods. In one embodiment, the HRV metric of the rootmean-square of successive differences (RMSSD) of RR intervals is used. The analytics system may consider the magnitude of the differences between 7-day moving averages and 3-day moving averages of these readings for a given day. Other embodiments may use Poincaré Plot analysis or other suitable metrics of HRV.

The recovery score algorithm may take into account RHR along with history of past intensity and recovery scores.

With regard to the user's resting heart rate, moving averages of the resting heart rate are analyzed to determine significant deviations. Consideration of the moving averages is important since day-to-day physiological variation is quite large even in healthy individuals. Therefore, the analytics system may perform a smoothing operation to distinguish changes from normal fluctuations.

Although an inactive condition, sleep is a highly active recovery state during which a major portion of the physiological recovery process takes place. Nonetheless, a small, yet significant, amount of recovery can occur throughout the day by rehydration, macronutrient replacement, lactic acid removal, glycogen re-synthesis, growth hormone production and a limited amount of musculoskeletal repair. In assessing the user's sleep quality, the analytics system generates a sleep score using continuous data collected by an exemplary physiological measurement system regarding the user's heart rate, skin conductivity, ambient temperature and accelerometer/gyroscope data throughout the user's sleep. Collection and use of these four streams of data enable an understanding of sleep previously only accessible through invasive and disruptive over-night laboratory testing. For example, an increase in skin conductivity when ambient temperature is not increasing, the wearer's heart rate is low, and the accelerometer/gyroscope shows little motion, may indicate that the wearer has fallen asleep. The sleep score indicates and is a measure of sleep efficiency (how good the user's sleep was) and sleep duration (if the user had sufficient sleep). Each of these measures is determined by a combination of physiological parameters, personal habits and daily stress/strain (intensity) inputs. The actual data measuring the time spent in various stages of sleep may be combined with the wearer's recent daily history and a longer-term data set describing the wearer's personal habits to assess the level of sleep sufficiency achieved by the user. The sleep score is designed to model sleep quality in the context of sleep duration and history. It thus takes advantage of the continuous monitoring nature of the exemplary physiological measurement systems disclosed herein by considering each sleep period in the context of biologically-determined sleep needs, pattern-determined sleep needs and historically-determined sleep debt.

The recovery and sleep score values are stored on a non-transitory storage medium for retrieval, display and usage. The recovery and/or sleep score values are, in some embodiments, displayed on a user interface rendered on a visual display device. The recovery and/or sleep score values may be displayed as numbers and/or with the aid of graphical tools, e.g., a graphical display of the scale of recovery scores with current score, and the like. In some embodiments, the recovery and/or sleep score may be indicated by audio. The recovery score values are, in some embodiments, displayed along with one or more quantitative or qualitative pieces of information on the user including, but not limited to, whether the user has recovered sufficiently, what level of activity the user is prepared to perform, whether the user is prepared to perform an exercise routine a particular desired intensity, whether the user should rest and the duration of recommended rest, whether the exercise regimen of the user should be automatically adjusted (e.g., made easier if the recovery score is low), and the like. In one embodiment, the analytics system may automatically generate, store and display an exercise regimen customized based on the recovery scores of the user alone or in combination with the intensity scores.

As discussed above, the sleep performance metric may be based on parameters like the number of hours of sleep, sleep onset latency, and the number of sleep disturbances. In this manner, the score may compare a tactical athlete's duration and quality of sleep in relation to the tactical athlete's evolving sleep need (e.g., a number of hours based on recent strain, habitual sleep need, signs of sickness, and sleep debt). By way of example, a soldier may have a dynamically changing need for sleep, and it may be important to consider the total hours of sleep in relation to the amount of sleep that may have been required. By providing an accurate sensor for sleep and sleep performance, an aspect may evaluate sleep in the context of the overall day and lifestyle of a specific user.

Figure 9:
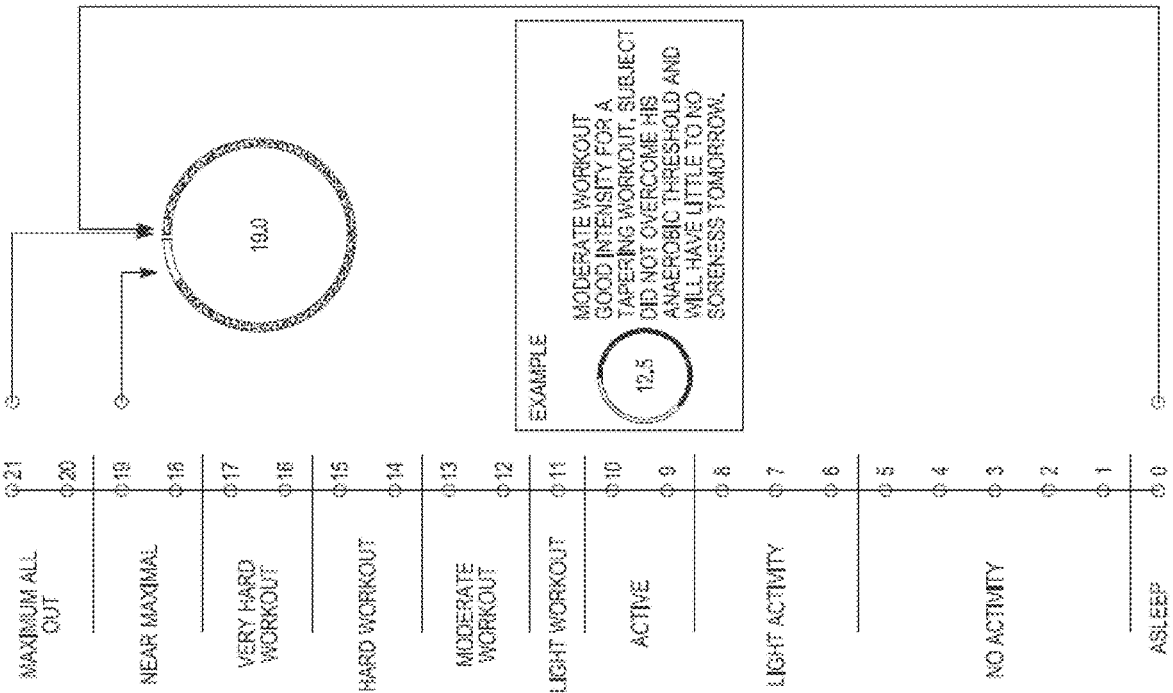
FIG. 9 illustrates a display of an intensity score index indicated in a circular graphic component with an exemplary current score of 19.0 indicated.

FIG. 8 is a flow chart illustrating an exemplary method by which a user may use intensity and recovery scores. In step 1102, the wearable physiological measurement system begins determining heart rate variability (HRV) measurements based on continuous heart rate data collected by an exemplary physiological measurement system. In some cases, it may take the collection of several days of heart rate data to obtain an accurate baseline for the HRV. In step 1104, the analytics system may generate and display intensity score for an entire day or an exercise routine. In some cases, the analytics system may display quantitative and/or qualitative information corresponding to the intensity score. FIG. 9 illustrates an exemplary display of an intensity score index indicated in a circular graphic component with an exemplary current score of 19.0 indicated. The graphic component may indicate a degree of difficulty of the exercise corresponding to the current score selected from, for example, maximum all out, near maximal, very hard, hard, moderate, light, active, light active, no activity, asleep, and the like. The display may indicate, for example, that the intensity score corresponds to a good and tapering exercise routine, that the user did not overcome his anaerobic threshold and that the user will have little to no soreness the next day.

In step 1106, in an exemplary embodiment, the analytics system may automatically generate or adjust an exercise routine or regimen based on the user's actual intensity scores or desired intensity scores. For example, based on inputs of the user's actual intensity scores, a desired intensity score (that is higher than the actual intensity scores) and a first exercise routine currently performed by the user (e.g., walking), the analytics system may recommend a second different exercise routine that is typically associated with higher intensity scores than the first exercise routine (e.g., running).

In step 1108, at any given time during the day (e.g., every morning), the analytics system may generate and display a recovery score. In some cases, the analytics system may display quantitative and/or qualitative information corresponding to the intensity score. For example, in step 1110, in an exemplary embodiment, the analytics system may determine if the recovery is greater than (or equal to or greater than) a first predetermined threshold (e.g., about 60% to about 80% in some examples) that indicates that the user is recovered and is ready for exercise. If this is the case, in step 1112, the analytics system may indicate that the user is ready to perform an exercise routine at a desired intensity or that the user is ready to perform an exercise routine more challenging than the past day's routine. Otherwise, in step 1114, the analytics system may determine if the recovery is lower than (or equal to or lower than) a second predetermined threshold (e.g., about 10% to about 40% in some examples) that indicates that the user has not recovered. If this is the case, in step 1116, the analytics system may indicate that the user should not exercise and should rest for an extended period. The analytics system may, in some cases, the duration of recommended rest. Otherwise, in step 1118, the analytics system may indicate that the user may exercise according to his/her exercise regimen while being careful not to overexert him/herself. The thresholds may, in some cases, be adjusted based on a desired intensity at which the user desires to exercise. For example, the thresholds may be increased for higher planned intensity scores.

Figure 10:
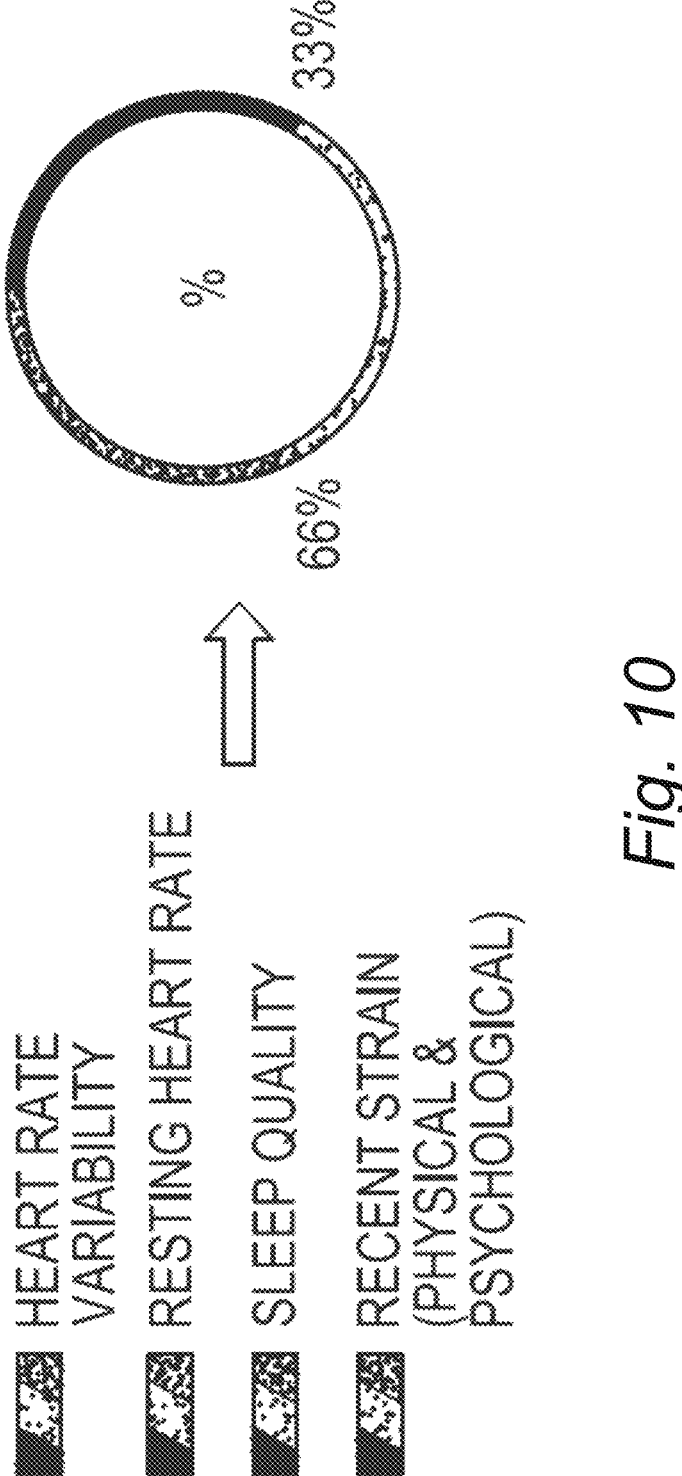
FIG. 10 illustrates a display of a recovery score index indicated in a circular graphic component with a first threshold of 66% and a second threshold of 33% indicated.
Figures 11A, 11B, 11C:
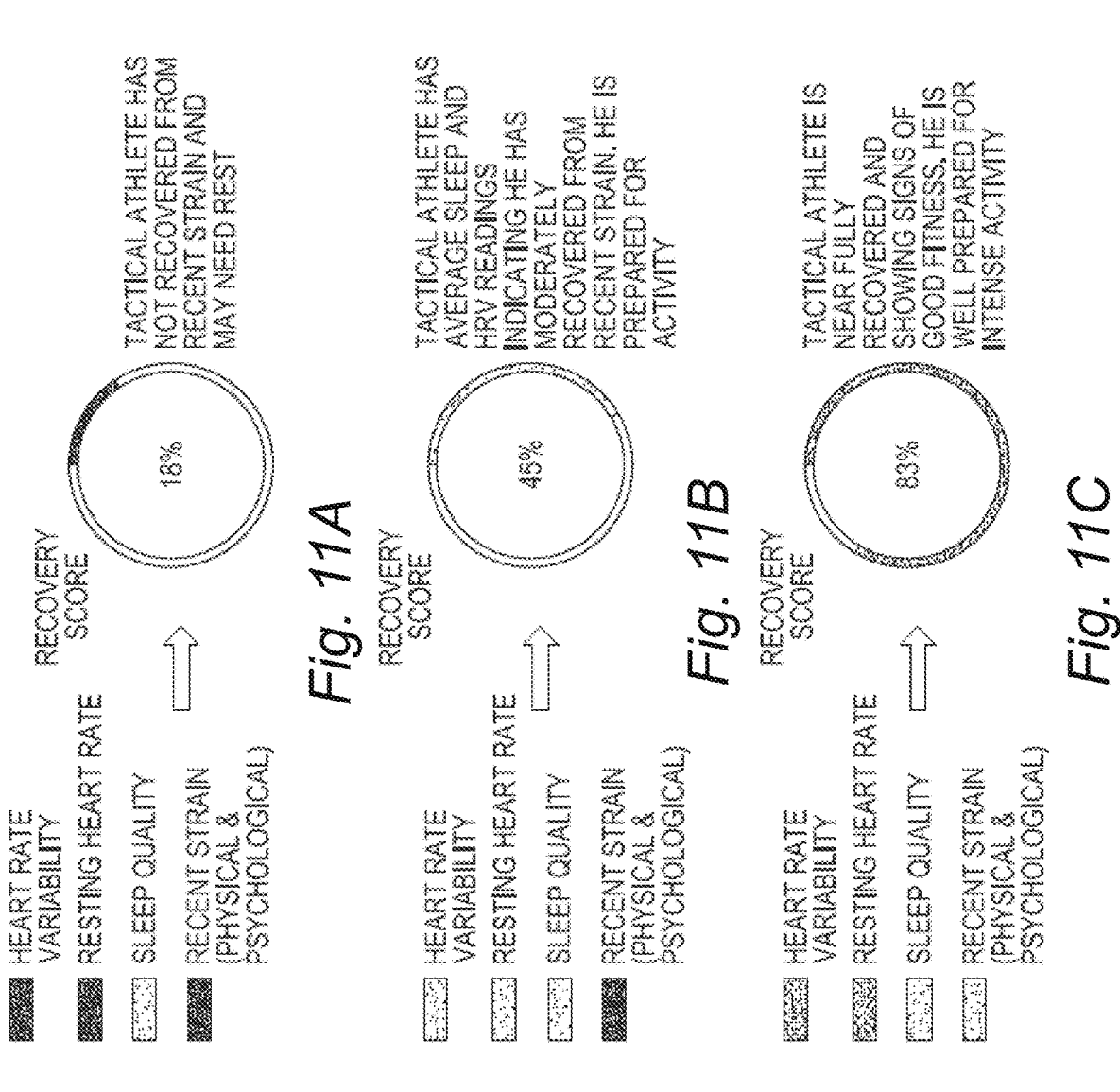
FIG. 11A illustrates a recovery score graphic component with a recovery score and qualitative information corresponding to the recovery score.
FIG. 11B illustrates a recovery score graphic component with a recovery score and qualitative information corresponding to the recovery score.
FIG. 11C illustrates a recovery score graphic component with a recovery score and qualitative information corresponding to the recovery score.
Figure 12A:
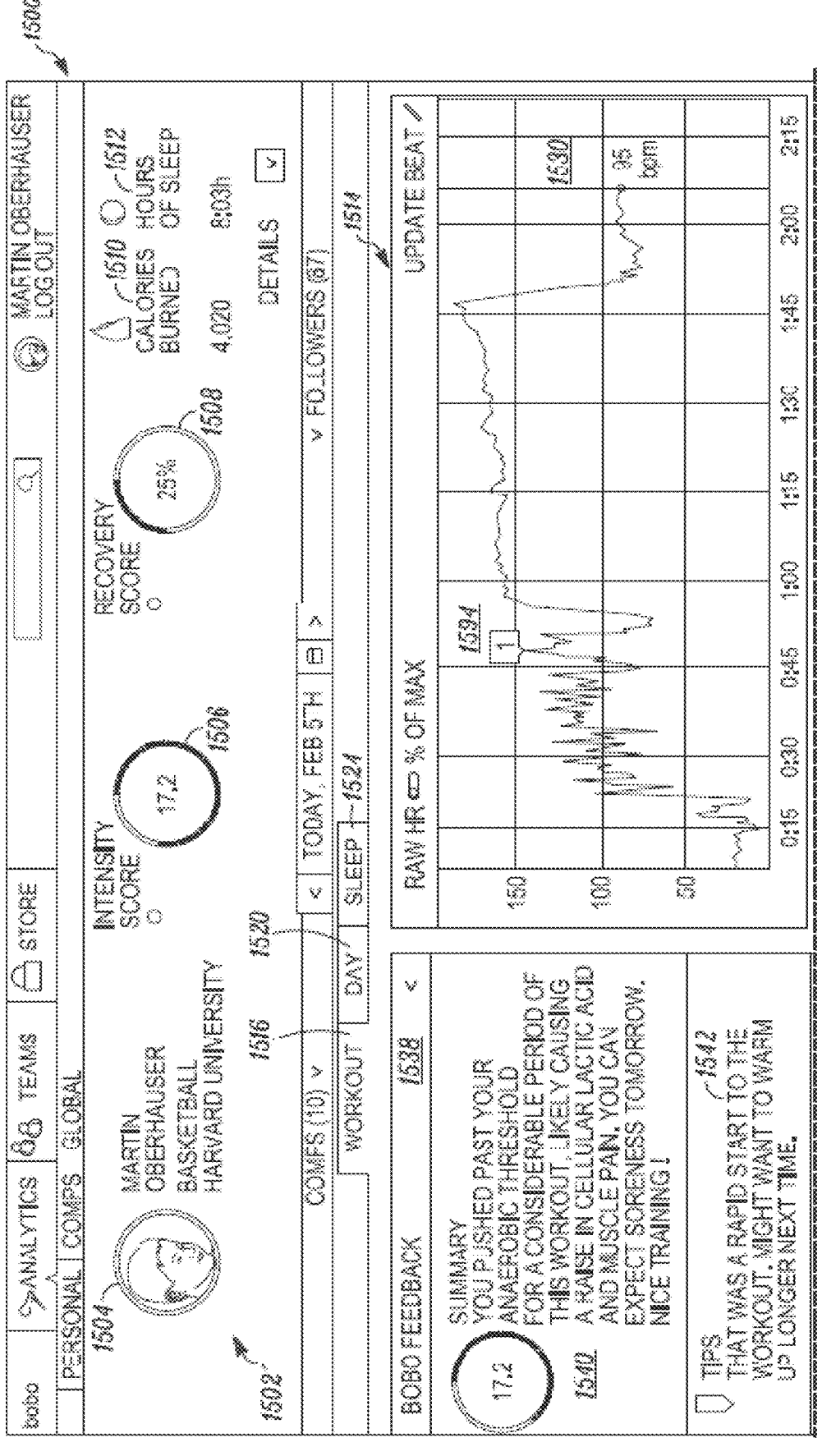
FIG. 12A illustrates part of a user interface for displaying physiological data specific to a user as rendered on visual display device.
Figure 13A:
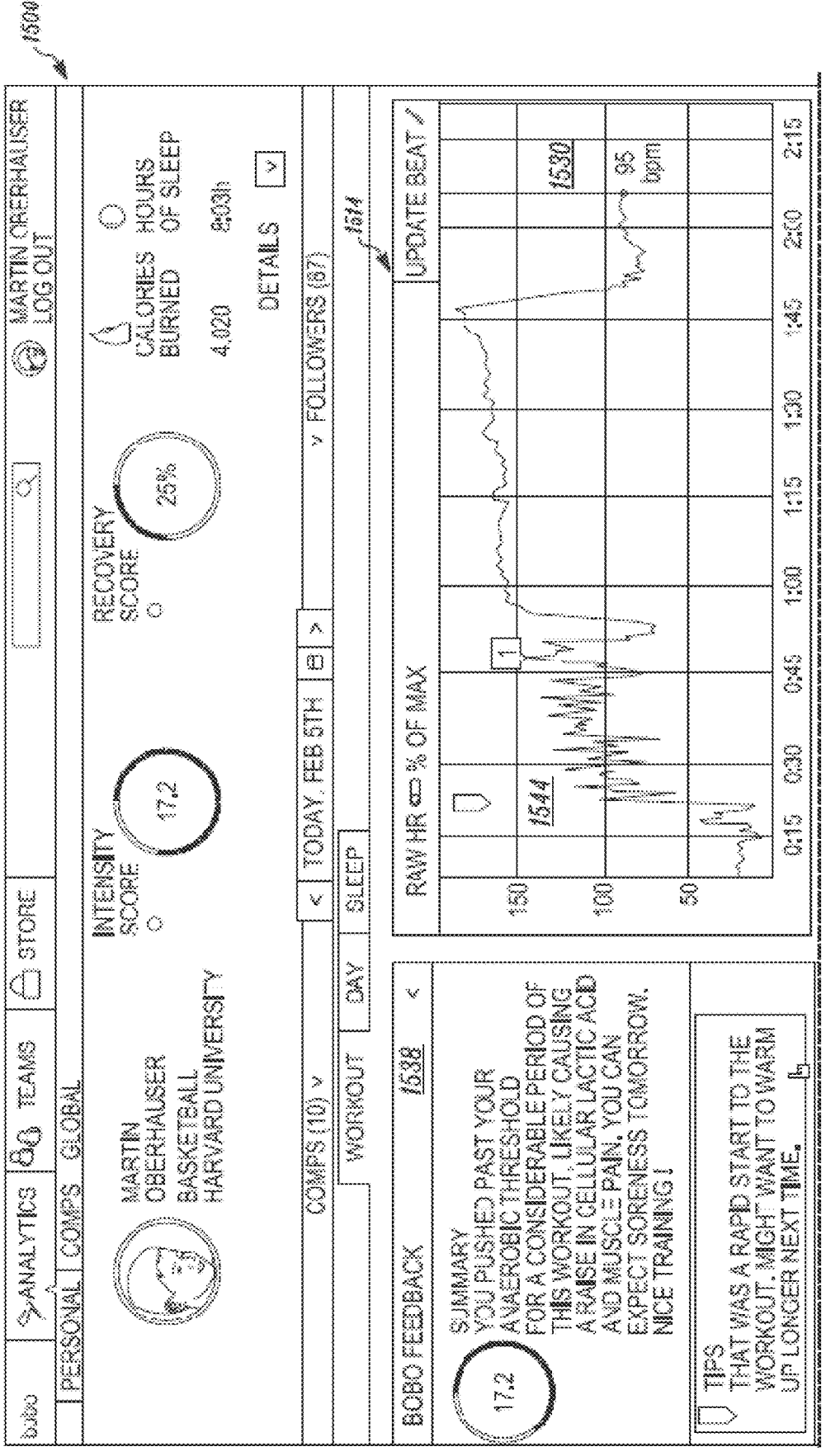
FIG. 13A illustrates part of a user interface for displaying physiological data specific to a user as rendered on visual display device.
Figure 14A:
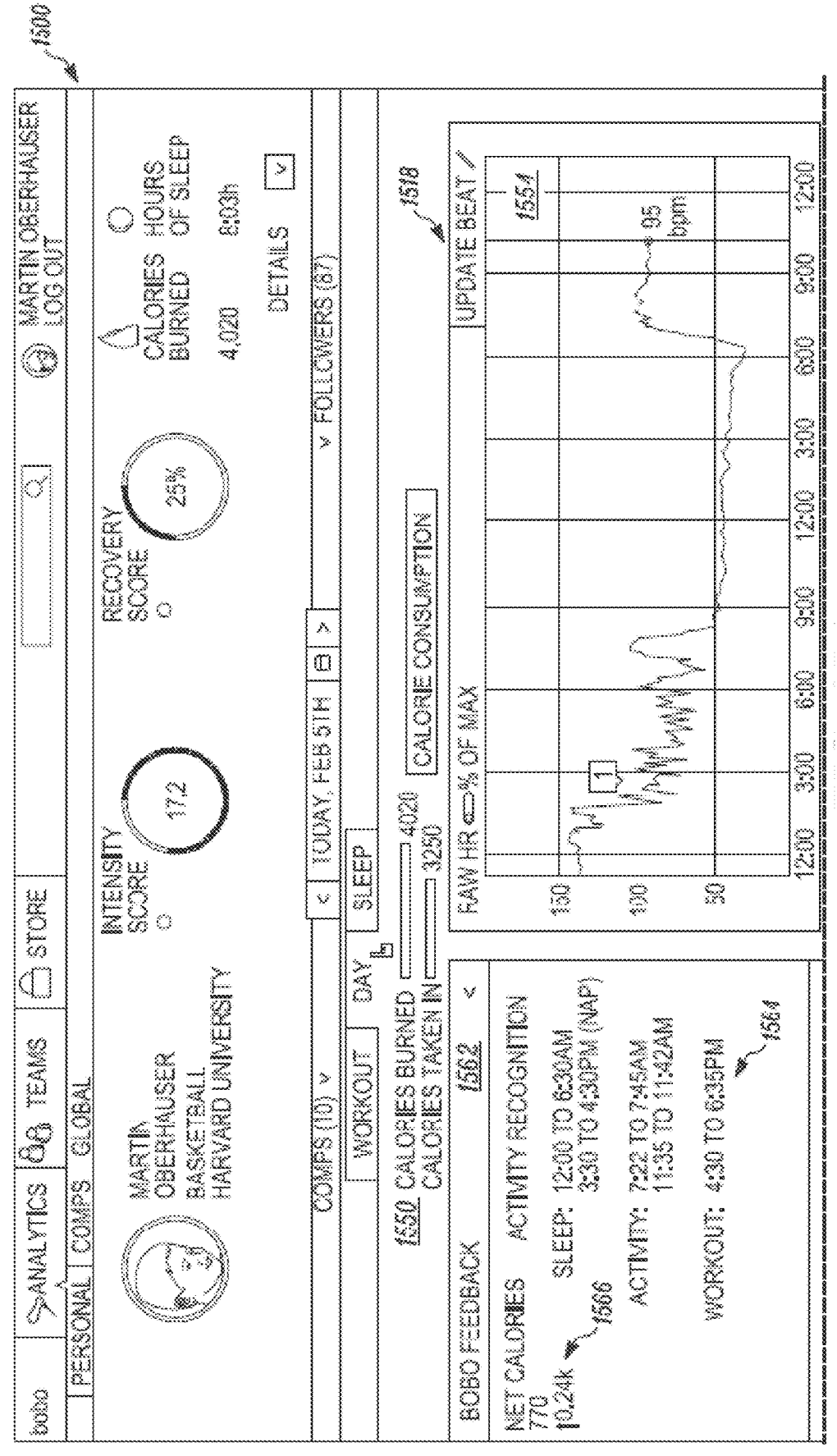
FIG. 14A illustrates part of a user interface for displaying physiological data specific to a user as rendered on visual display device.
Figure 15A:
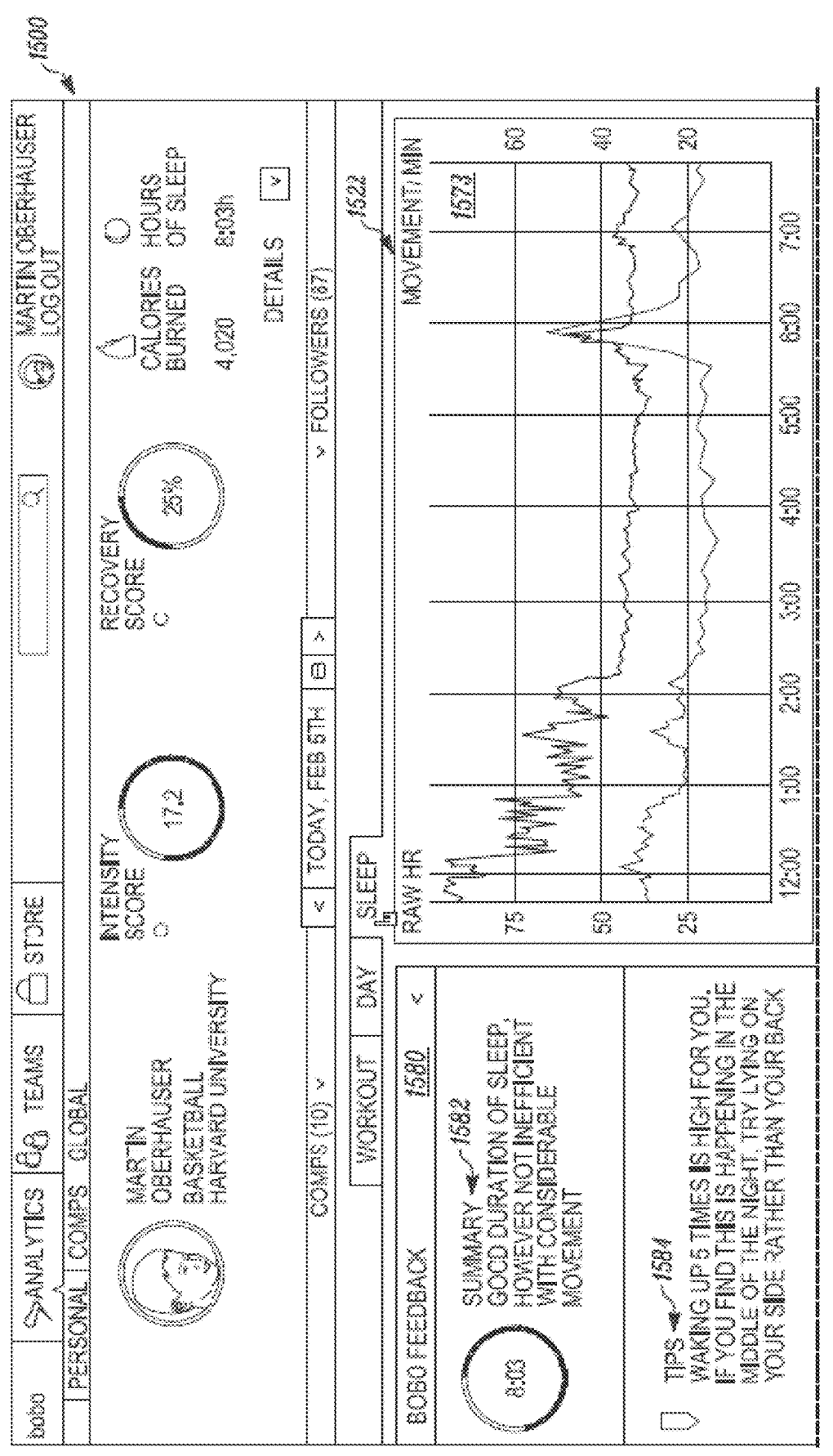
FIG. 15A illustrates part of a user interface for displaying physiological data specific to a user as rendered on visual display device.

FIG. 10 illustrates an exemplary display of a recovery score index indicated in a circular graphic component with a first threshold of 66% and a second threshold of 33% indicated. FIGS. 11A-11C illustrate the recovery score graphic component with exemplary recovery scores and qualitative information corresponding to the recovery scores.

Optionally, in an exemplary embodiment, the analytics system may automatically generate or adjust an exercise routine or regimen based on the user's actual recovery scores (e.g., to recommend lighter exercise for days during which the user has not recovered sufficiently). This process may also use a combination of the intensity and recovery scores.

The analytics system may, in some embodiments, determine and display the intensity and/or recovery scores of a plurality of users in a comparative manner. This enables users to match exercise routines with others based on comparisons among their intensity scores.

III. Exemplary Displays and User Interfaces

Exemplary embodiments also provide a vibrant and interactive online community for displaying and sharing physiological data among users. Exemplary systems have the ability to stream the physiological information wirelessly, directly or through a mobile device application, to an online website. The website allows users to monitor their own fitness results, share information with their teammates and coaches, compete with other users, and win status. Both the wearable system and the website allow a user to provide feedback regarding his day, which enables recovery and performance ratings. One aspect is directed to providing an online website for health and fitness monitoring. In some embodiments, the website may be a social networking site. The website may allow users, such as young athletes, to monitor their own fitness results, share information with their teammates and coaches, compete with other users, and win prizes. A user may include an individual whose health or fitness is being monitored, such as an individual wearing a bracelet disclosed herein, an athlete, a sports team member, a personal trainer or a coach. In some embodiments, a user may pick their own trainer from a list to comment on their performance.

In some embodiments, the website may be configured to provide an interactive user interface. The website may be configured to display results based on analysis on physiological data received from one or more devices. The website may be configured to provide competitive ways to compare one user to another, and ultimately a more interactive experience for the user. For example, in some embodiments, instead of merely comparing a user's physiological data and performance relative to that user's past performances, the user may be allowed to compete with other users and the user's performance may be compared to that of other users.

In some embodiments, the website may be a mobile website or a mobile application. In some embodiments, the website may be configured to communicate data to other websites or applications.

The exemplary website may include a brief and free sign-up process during which a user may create an account with his/her name, account name, email, home address, height, weight, age, and a unique code provided in his/her wearable physiological measurement system. The unique code may be provided, for example, on the wearable system itself or in the packaged kit. Once subscribed, continuous physiological data received from the user's system may be retrieved in a real-time continuous basis and presented automatically on a webpage associated with the user. Additionally, the user can add information to his profile, such as, a picture, favorite activities, sports team(s), and the user may search for teammates/friends on the website for sharing information.

FIGS. 12A-15B illustrate an exemplary user interface 1500 for displaying physiological data specific to a user as rendered on visual display device. The user interface 1500 may take the form of a webpage in some embodiments. One of ordinary skill in the art will recognize that the information in FIGS. 12A-15B represent non-limiting illustrative examples. The user interface 1500 may include a summary panel 1502 including an identification 1504 of the user (e.g., a real or account name) with, optionally, a picture or photo corresponding to the user. The summary panel 1502 may also display the current intensity score 1506 and the current recovery score 1508 of the user. In some embodiments, the summary panel 1502 may display the number of calories burned by the user 1510 that day and the number of hours of sleep 1512 obtained by the user the previous night.

The user interface 1500 may also include panels for presenting information on the user's workouts—a workout panel 1514 accessible using tab 1516, day—a day panel 1518 accessible using tab 1520, and sleep—a sleep panel 1522 accessible using tab 1524. The same or different feedback panels may be associated with the workout, day and sleep panels. The panels may enable the user to select and customize one or more informative panels that appear in his/her user interface display.

The workout panel 1514 may present quantitative information on the user's health and exercise routines, for example, a graph 1530 of the user's continuous heart rate during the exercise, statistics 1532 on the maximum heart rate, average heart rate, duration of exercise, number of steps taken and calories expended, zones 1534 in which the maximum heart rate fell during the exercise, and a graph 1536 of the intensity scores over a period of time (e.g., seven days).

A feedback panel 1538 associated with the workout panel 1514 may present information on the intensity score and the exercise routines performed by the user during a selected period of time including, but not limited to, quantitative information, qualitative information, feedback, recommendations on future exercise routines, and the like. The feedback panel 1538 may present the intensity score along with a qualitative summary 1540 of the score indicating, for example, whether the user pushed past his anaerobic threshold for a considerable period of the exercise, whether the exercise is likely to cause muscle pain and soreness, and the like. Based on analysis of the quantitative health parameters monitored during the exercise routine, the feedback panel

1538 may present one or more tips 1542 on adjusting the exercise routine, for example, that the exercise routine started too rapidly and that the user should warm up for longer. In some cases, upon selection of the tips sub-panel 1542, a corresponding indicator 1544 may be provided in the heart rate graph 1530.

Based on analysis of the quantitative health parameters monitored during the exercise routine, the feedback panel 1538 may also present qualitative information 1545 on the user's exercise routine, for example, comparison of the present day's exercise routine to the user's historical exercise data. Such information may indicate, for example, that the user's maximum heart rate for the day's exercise was the highest ever recorded, that the steps taken by the user that day was the fewest ever recorded, that the user burned a lot of calories and that more calories may be burned by lowering the intensity of the exercise, and the like. The feedback panel 1538 may also present cautionary indicators 1546 to warn the user of future anticipated health events, for example, the likelihood of soreness (e.g., if the intensity score is higher than a predefined threshold), and the like.

An exemplary analytics system may analyze the information presented in the workout panel 1514 and determine whether the user performed a specific exercise routine or activity. As one example, given a small number of steps taken and a high calorie burn and heart rate, the system may determine that it is possible the user rode a bicycle that day. In some cases, the feedback panel 1538 may prompt the user to confirm whether he/she indeed performed that activity in a user field 1548. This user input may be displayed and/or used to improve an understanding of the user's health and exercise routines.

The day panel 1518 may include information on health parameters of the user during the current day including, but not limited to, the number of calories burned and the number of calories taken in 1500 (which may be based on user input on the foods eaten), a graph 1554 of the day's continuous heart rate, statistics 1556 on the resting heart rate and steps taken by the user that day, a graph 1558 of the calories burned that and other days, and the like.

In some cases, an analytics system may analyze the physiological data (e.g., heart rate data) and estimate the durations of sleep, activity and workout during the day. A feedback panel 1562 associated with the day panel 1518 may present these durations 1564. In some cases, the feedback panel 1562 may display a net number of calories consumed by the user that day 1566. Based on analysis of the quantitative health parameters monitored during the exercise routine, the feedback panel 1562 may also present qualitative information 1568 on the user's exercise routine. Such information may indicate, for example, that the user was stressed at a certain point in the day (e.g., if there was a high level of sweat with little activity), that the user's maximum heart rate for the day's exercise was the highest ever recorded, that the steps taken by the user that day was the fewest ever recorded, that the user burned a lot of calories and that more calories may be burned by lowering the intensity of the exercise, and the like. The feedback panel 1562 may also present cautionary indicators 1570 to warn the user of future anticipated health events, for example, tachycardia, susceptibility to illness or overtraining (e.g., if the resting heart rate is elevated for a few days), and the like.

An exemplary analytics system may analyze the information presented in the day panel 1518 and determine whether the user performed a specific exercise routine or activity. As one example, given an elevated heart rate with little activity, the system may determine that it is possible the user drank coffee at that point. In some cases, the feedback panel 1562 may prompt the user to confirm whether he/she indeed performed that activity in a user field 1572. This user input may be displayed and/or used to improve an understanding of the user's health and exercise routines.

The sleep panel 1522 may include information on health parameters of the user during sleep including, but not limited to, an overlaid graph 1573 of heart rate and movement during sleep, statistics 1574 on the maximum heart rate, minimum heart rate, number of times the user awoke during sleep, average movement during sleep, a sleep cycle indicator 1576 showing durations spent awake, in light sleep, in deep sleep and in REM sleep, and a sleep duration graph 1578 showing the number of hours slept over a period of time.

A feedback panel 1580 associated with the sleep panel 1522 may present information on the user's sleep including, but not limited to, quantitative information, qualitative information, feedback, recommendations on future exercise routines, and the like. The feedback panel 1580 may present a sleep score and/or a number of hours of sleep along with a qualitative summary of the score 1582 indicating, for example, whether the user slept enough, whether the sleep was efficient or inefficient, whether the user moved around and how much during sleep, and the like. Based on analysis of the quantitative health parameters monitored during sleep, the feedback panel 1580 may present one or more tips 1584 on adjusting sleep, for example, that the woke up a number of times during sleep and that user can try to sleep on his side rather than on his back.

Based on analysis of the quantitative health parameters monitored during the exercise routine, the feedback panel 1580 may also present qualitative information 1586 on the user's sleep. Such information may indicate, for example, that the user's maximum heart rate for the day's exercise was the highest ever recorded during sleep. The feedback panel 1580 may also present cautionary indicators 1588 to warn the user of future anticipated health events, for example, a sign of overtraining and a recommendation to get more sleep (e.g., if the user awoke many times during sleep and/or if the user moved around during sleep.

The user interface 1500 may provide a user input field 1590 for enabling the user to indicate his/her feelings, e.g., activities performed perceived exertion, energy level, performance. The user interface 1500 may also provide a user input field 1592 for enabling the user to indicate other facts about his exercise routine, e.g., comments on what the user was doing at a specific point in the exercise routine with a link 1594 to a corresponding point in the heart rate graph 1530. In some embodiments, the user may specify a route and/or location on a map at which the exercise routine was performed.

Exemplary embodiments also enable a user to compare his/her quantitative and/or qualitative physiological data with those of one or more additional users. A user may be presented with user selection components representing other users who data is available for display. When a pointer is hovered over a user selection component (e.g., an icon representing a user), a snapshot of the user's information is presented in a popup component, and clicking on the user selection component opens up the full user interface displaying the user's information. In some cases, the user selection components include certain user-specific data surrounding an image representing the user, for example, a graphic element indicating the user's intensity score. The user selection components may be provided in a grid as shown or in a linear listing for easier sorting. The users appearing in the user selection components may be sorted and/or ranked based on any desired criteria, e.g., intensity scores, who is experiencing soreness, and the like. A user may leave comments on other users' pages.

Similarly, a user may select privacy settings to indicate which aspects of his/her own data may be viewed by other users. Because the wearable systems described herein support truly continuous monitoring, a user may wish to carefully control whether and when data is transmitted wirelessly, stored in a remote data repository, and shared with others. A privacy switch as described herein may be usefully employed to toggle between various privacy settings or to explicitly select private or restricted times when no monitoring should occur.

Figure 16A:
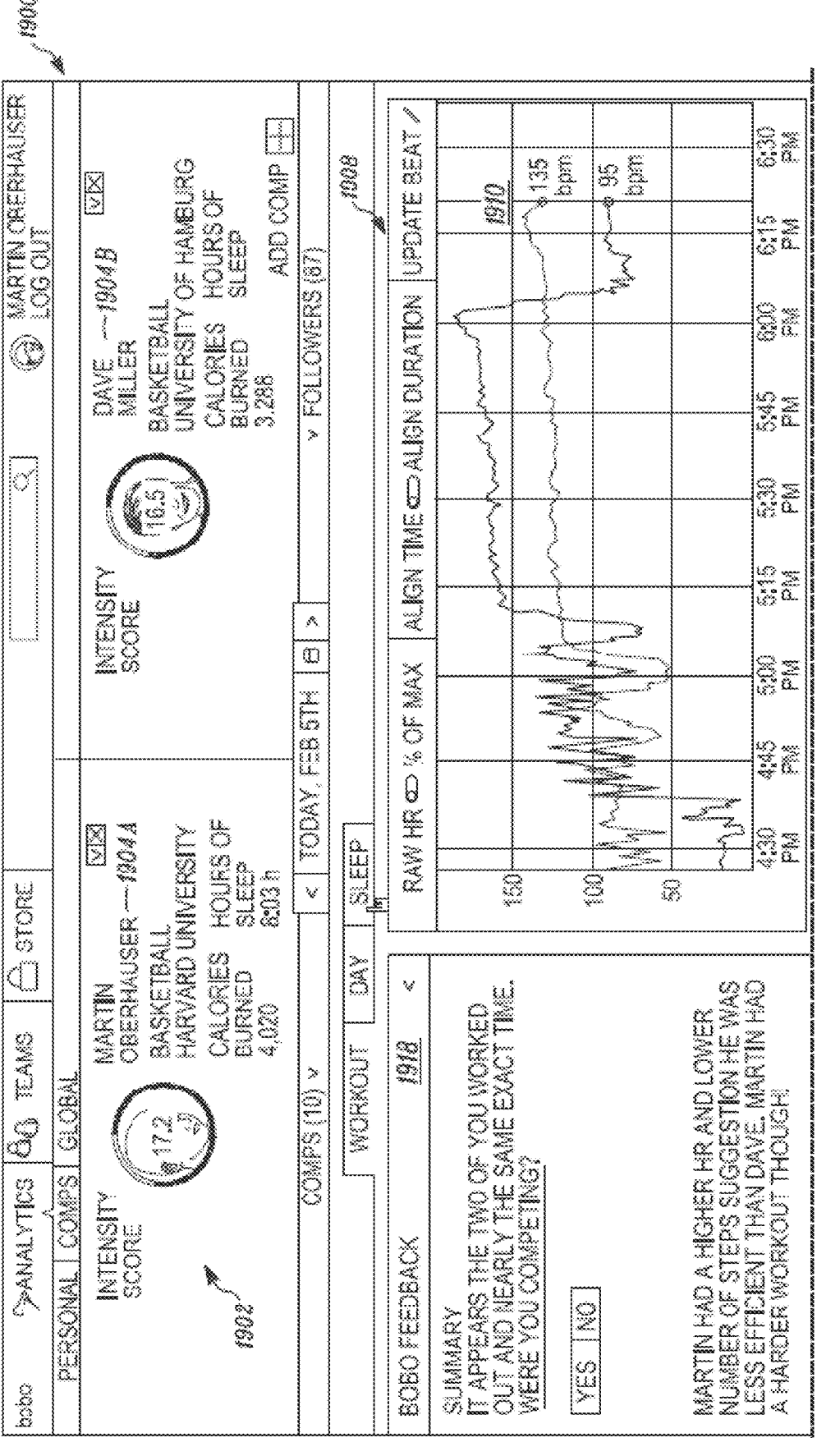
FIG. 16A illustrates part of a user interface rendered on a visual display device for displaying physiological data on a plurality of users.

FIGS. 16A and 16B illustrate an exemplary user interface 1900 rendered on a visual display device for displaying physiological data on a plurality of users. In some cases, a user may freely compare the data of any users whose data is available and accessible, i.e., set to an appropriate privacy level. In some cases, comparative data may correspond to a plurality of users who may be grouped together based on any suitable criteria, e.g., members of a gym, military team, and the like. In some cases, the user may be able to discover other users or comparable data by searching or performing queries on any desired parameters, for example, workouts, activities, age groups, locations, intensities, recoveries and the like. For example, a user may perform a query for "Workouts above a 17 Intensity in Boston for runners my age." The exemplary user interface may also identify or suggest users with whom to exchange data based on similar parameters. Data on any number of users may be presented and compared including, but not limited to, 2, 3, 4, 5, 6, 7, 8, 9, 10, and the like.

Figure 17:
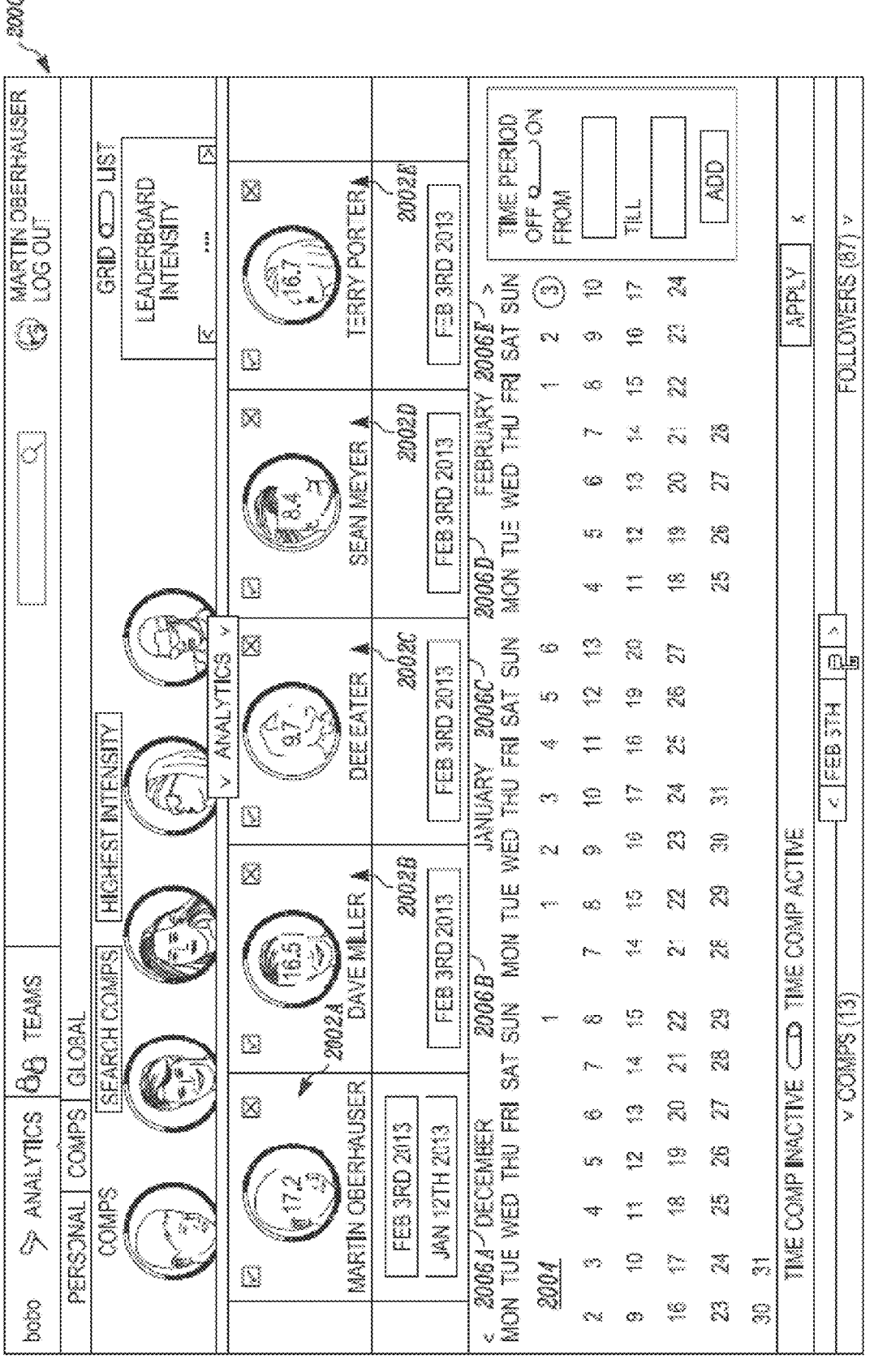
FIG. 17 illustrates a user interface that may be used to independently select time periods of data for multiple users so that the data from the selected periods may be displayed together.

In a default option, data from the same time period(s) may be presented for all of the users. In some embodiments, time periods for each user may be selected independently and data from the selected time periods may be displayed in a comparative manner on the same user interface, e.g., in one or more overlaid graphs. FIG. 17 illustrates a user interface 2000 that may be used to independently select time periods of data for each of five users so that the data from the selected periods may be displayed together. The user interface 2000 includes a representation of each user 2002a-2002e, optionally an indication of each user's intensity score, a calendar component 2004 for selecting the time periods, and a component 2006a-2006e indicating the time periods selected for each user. In some cases, data from different time periods (but, for example, for the same time duration) for the same user may be presented on the same user interface for comparative purpose, for example, to determine training progress.

In FIGS. 16A and 16B, the user interface 1900 may include a summary panel 1902 including an identification 1904a-1904b of the users (e.g., a real or account name) with, optionally, a picture or photo corresponding to the user. In some cases, the summary panel 1902 may also display certain information associated with the users, for example, their intensity scores.

A workout panel 1908 may present quantitative information on the users' health and exercise routines, for example, an overlaid graph 1910 of the users' continuous heart rate during the exercise, statistics 1912 on the users' maximum heart rate, average heart rate, duration of exercise, number of steps taken and calories expended, zones 1914 in which the users' maximum heart rate fell during the exercise, and an overlaid graph 1916 of the intensity scores over a period of time (e.g., seven days). A feedback panel 1918 associated with the workout panel 1908 may present comparative qualitative information on the users' exercise routines including, but not limited to, whether the users were working out at the same time, which user had a more difficult workout, the comparative efficiencies of the users, and the like. Similarly, a day panel and a sleep panel may present comparative information for the selected users.

The analytics system may analyze comparative data among a plurality of users and provide rankings of individuals, teams and groups of individuals (e.g., employees of a company, members of a gym) based on, for example, average intensity scores. For each user, the analytics system may calculate and display percentile rankings of the user with respect to all of the users in a community in terms of, for example, intensity scores, quality of sleep, and the like.

Exemplary embodiments also provide user interfaces to enable intuitive and efficient monitoring of a plurality of users by an individual with administrative powers to view the users' health data. Such an administrative user may be a physical instructor, trainer or coach who may use the interface to manage his/her clients' workout regimen.

Figure 18A:
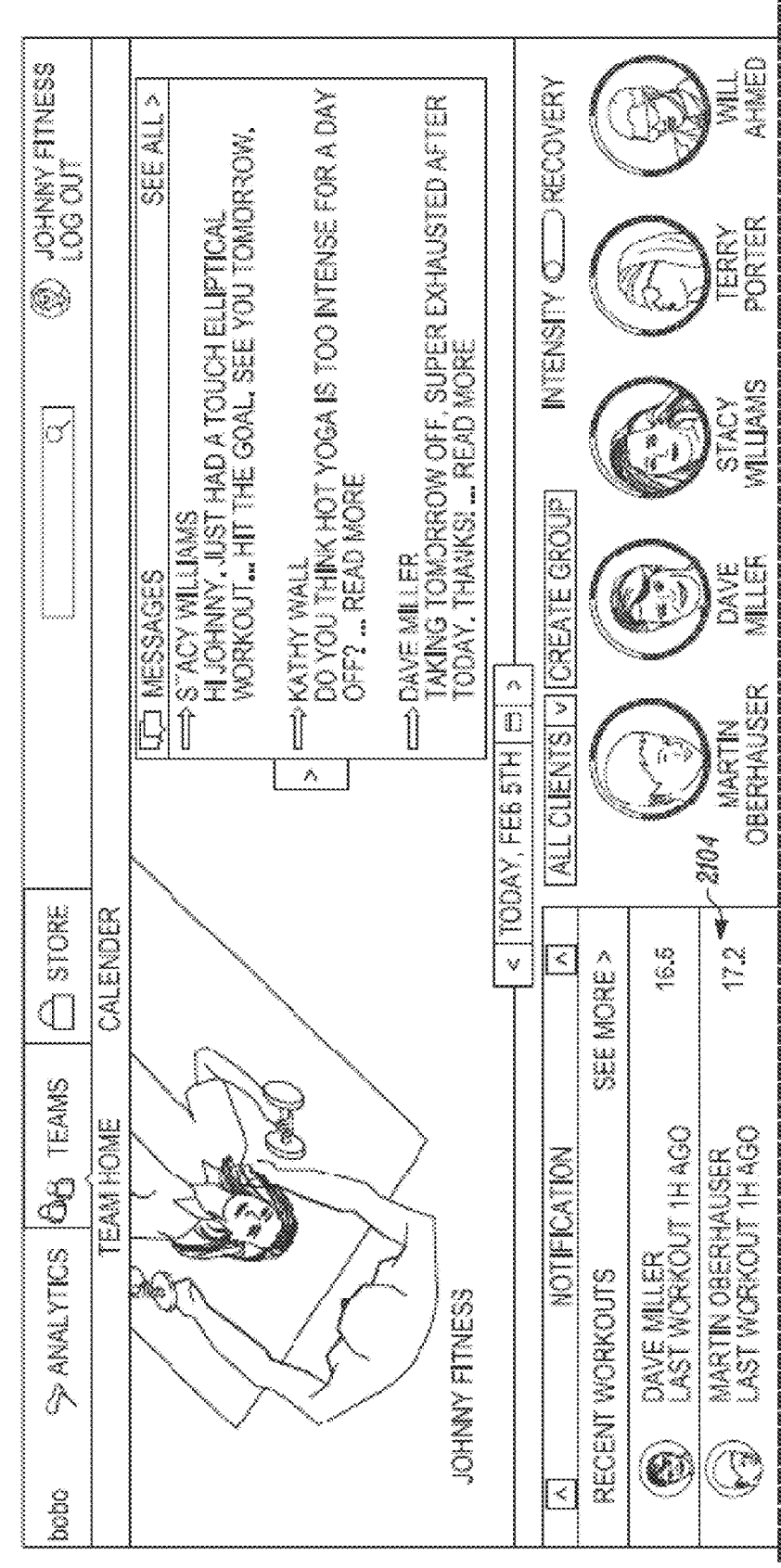
FIG. 18A illustrates part of a user interface viewable by an administrative user, including a selectable and editable listing of users (e.g., a trainer's clients) whose health information is available for display.
Figure 18B:
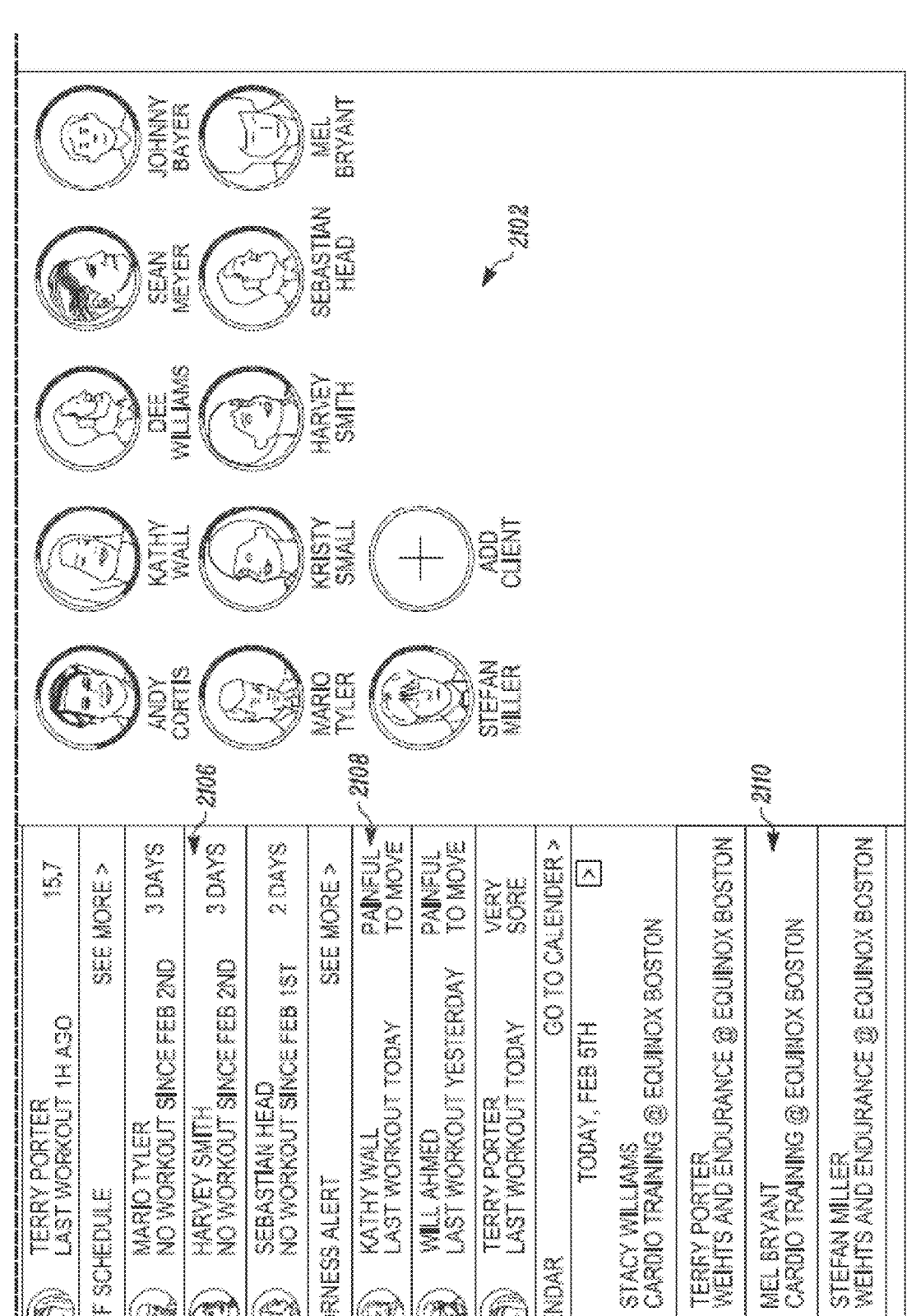
FIG. 18B illustrates part of a user interface viewable by an administrative user, including a selectable and editable listing of users (e.g., a trainer's clients) whose health information is available for display.

FIGS. 18A and 18B illustrate an exemplary user interface 2100 viewable by an administrative user, including a selectable and editable representation or listing 2102 of the users (e.g., a trainer's clients) whose health information is available for display. When a mouse is hovered over a user selection component (e.g., an icon representing a user), a snapshot of the user's information is presented in a popup component, and clicking on the user selection component opens up the full user interface displaying the user's information. In some cases, the user selection components include certain user-specific data surrounding an image representing the user, for example, a graphic element indicating the user's intensity score. The user selection components in the listing 2102 may be provided in a grid as shown or in a linear listing for easier sorting. The users appearing in the listing 2102 may be sorted and/or ranked based on any desired criteria, e.g., intensity scores, who is experiencing soreness, and the like. Selection of any one user causes the user interface specific to that user to be opened, for example, as shown in FIGS. 12A-15B. The administrative user may leave messages on the user interfaces of the different users. Selection of more than one user causes a user interface comparing the selected users to be opened, for example, as shown in FIGS. 16A and 16B.

The administrative user interface 2100 may include a listing of users 2104 who recently performed exercise routines including the time of their last workout and their intensity scores, a listing of users 2106 who are off-schedule in their exercise regimen and how many days they have not been exercising, a listing of users 2108 who are experiencing soreness (that may be determined automatically based on intensity scores), a listing of users who are sleep-deprived (that may be determined automatically based on sleep data), and the like. The user interface 2100 may also display a calendar or portion of a calendar 2110 indicating training times for different users. The calendar feature enables the administrative user to review exercise schedules over time and understand how well individuals or teams are meeting goals. For example, the administrative user may determine that an individual is undertraining if his intensity for the day was 18 whereas the team average was 14.

In any of the exemplary user interfaces disclosed herein, color coding may be used to indicate categories of any parameter. For example, in a day panel of a user interface, color coding may be used to indicate whether a user's day was difficult (e.g., with the color red), tapering (e.g., with the color yellow), or a day off from training (e.g., with the color blue).

Exemplary embodiments enable selected qualitative and/or quantitative data from any of the user interfaces disclosed herein to be selected, packaged and exported to an external application, computational device or webpage (e.g., a blog) for display, storage and analysis. The data may be selected based on any desired characteristic including, but not limited to, gender, age, location, activity, intensity level, and any combinations thereof. An online blog may be presented to display the data and allow users to comment on the data.

IV. Exemplary Computing Devices

Various aspects and functions described herein may be implemented as hardware, software or a combination of hardware and software on one or more computer systems. Exemplary computer systems that may be used include, but are not limited to, personal computers, embedded computing systems, network appliances, workstations, mainframes, networked clients, servers, media servers, application servers, database servers, web servers, virtual servers, and the like. Other examples of computer systems that may be used include, but are not limited to, mobile computing devices, such as wearable devices, cellular phones and personal digital assistants, and network equipment, such as load balancers, routers and switches.

Figure 19:
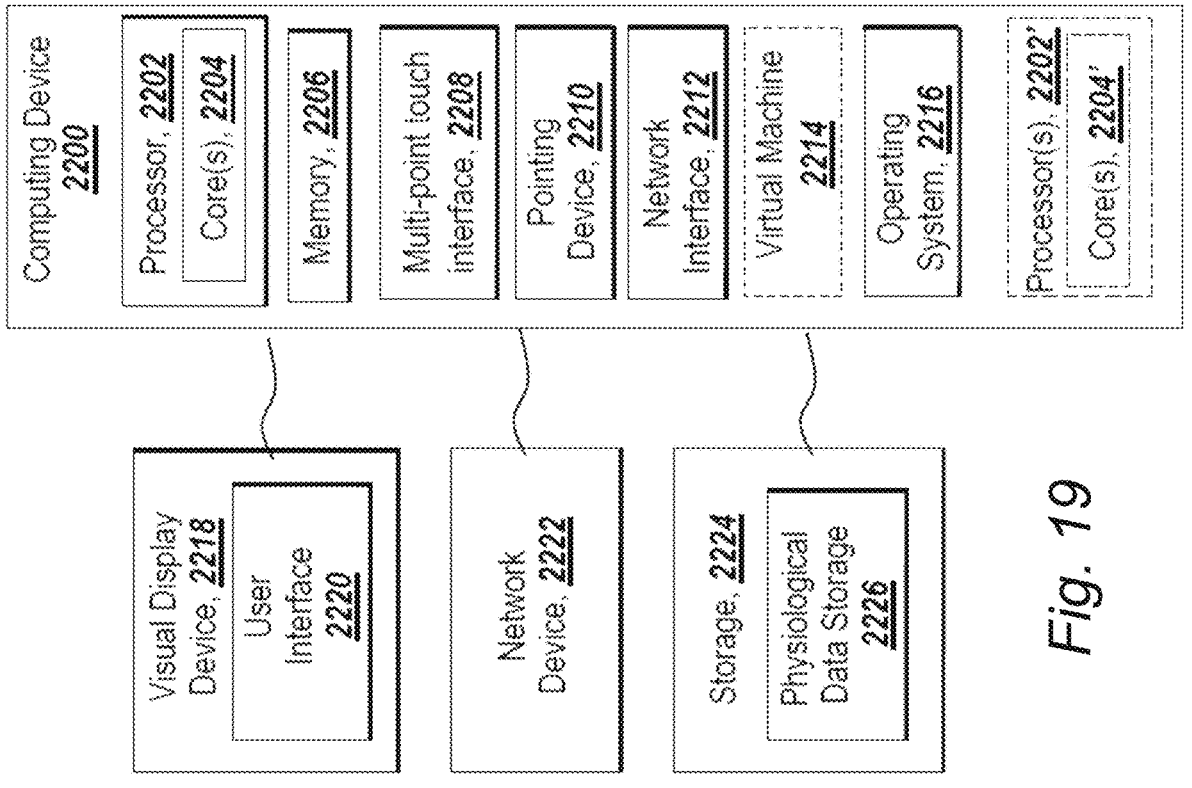
FIG. 19 is a block diagram of a computing device that may be used herein.
Figure 20:
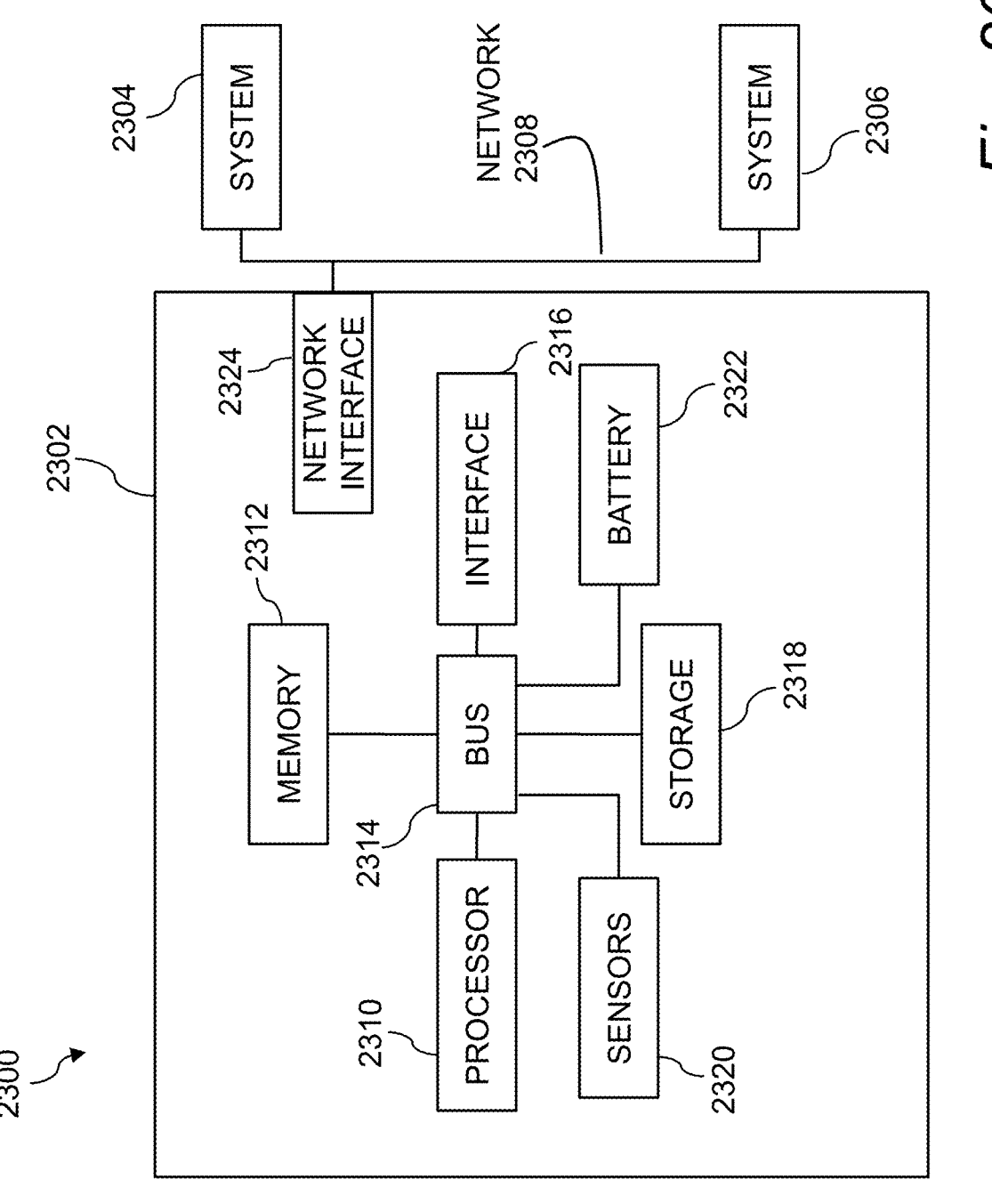
FIG. 20 is a block diagram of a distributed computer system in which various aspects and functions in accord with the present disclosure may be practiced.

FIG. 19 is a block diagram of an exemplary computing device 2200 that may be used in to perform any of the methods provided by exemplary embodiments. The computing device may be configured as an embedded system in the integrated circuit board(s) of a wearable physiological measurements system and/or as an external computing device that may receive data from a wearable physiological measurement system.

The computing device 2200 includes one or more non-transitory computer-readable media for storing one or more computer-executable instructions or software for implementing exemplary embodiments. The non-transitory computer-readable media may include, but are not limited to, one or more types of hardware memory, non-transitory tangible media (for example, one or more magnetic storage disks, one or more optical disks, one or more USB flash drives), and the like. For example, memory 2206 included in the computing device 2200 may store computer-readable and computer-executable instructions or software for implementing exemplary embodiments. The computing device 2200 also includes processor 2202 and associated core 2204, and optionally, one or more additional processor(s) 2202' and associated core(s) 2204' (for example, in the case of computer systems having multiple processors/cores), for executing computer-readable and computer-executable instructions or software stored in the memory 2206 and other programs for controlling system hardware. Processor 2202 and processor(s) 2202' may each be a single core processor or multiple core (2204 and 2204') processor.

Virtualization may be employed in the computing device 2200 so that infrastructure and resources in the computing device may be shared dynamically. A virtual machine 2214 may be provided to handle a process running on multiple processors so that the process appears to be using only one computing resource rather than multiple computing resources. Multiple virtual machines may also be used with one processor.

Memory 2206 may include a computer system memory or random access memory, such as DRAM, SRAM, EDO RAM, and the like. Memory 2206 may include other types of memory as well, or combinations thereof.

A user may interact with the computing device 2200 through a visual display device 2218, such as a computer monitor, which may display one or more user interfaces 2220 that may be provided in accordance with exemplary embodiments. The visual display device 2218 may also display other aspects, elements and/or information or data associated with exemplary embodiments, for example, views of databases, photos, and the like. The computing device 2200 may include other I/O devices for receiving input from a user, for example, a keyboard or any suitable multi-point touch interface 2208, a pointing device 2210 (e.g., a mouse). The keyboard 2208 and the pointing device 2210 may be coupled to the visual display device 2218. The computing device 2200 may include other suitable conventional I/O peripherals.

The computing device 2200 may also include one or more storage devices 2224, such as a hard-drive, CD-ROM, or other computer readable media, for storing data and computer-readable instructions and/or software that implement exemplary methods as taught herein. Exemplary storage device 2224 may also store one or more databases 2026 for storing any suitable information required to implement exemplary embodiments. The databases may be updated by a user or automatically at any suitable time to add, delete or update one or more items in the databases.

The computing device 2200 may include a network interface 2212 configured to interface via one or more network devices 2222 with one or more networks, for example, Local Area Network (LAN), Wide Area Network (WAN) or the Internet through a variety of connections including, but not limited to, standard telephone lines, LAN or WAN links (for example, 802.11, T1, T3, 56 kb, X.25), broadband connections (for example, ISDN, Frame Relay, ATM), wireless connections, controller area network (CAN), or some combination of any or all of the above. The network interface 2212 may include a built-in network adapter, network interface card, PCMCIA network card, card bus network adapter, wireless network adapter, USB network adapter, modem or any other device suitable for interfacing the computing device 2200 to any type of network capable of communication and performing the operations described herein. Moreover, the computing device 2200 may be any computer system, such as a workstation, desktop computer, server, laptop, handheld computer, tablet computer (e.g., the iPad® tablet computer), mobile computing or communication device (e.g., the iPhone® communication device), or other form of computing or telecommunications device that is capable of communication and that has sufficient processor power and memory capacity to perform the operations described herein.

The wearable physiological measurement system may record and transmit at least the following types of data to an external computing system, mobile communication system or the Internet: raw continuously-detected data (e.g., heart rate data, movement data, galvanic skin response data) and processed data based on the raw data (e.g., RR intervals determined from the heart rate data). Transmission modes may be wired (e.g., using USB stick inserted into a USB port on the system) or wireless (e.g., using a wireless transmitter). The raw and processed data may be transmitted together or separately using different transmission modes. Since a raw data file is typically substantially larger than a processed data file, the raw data file may be transmitted using WiFi or a USB stick, while the processed data file may be transmitted using Bluetooth.

An exemplary wearable system may include a 2G, 3G or 4G chip that wirelessly uploads all data to the website disclosed herein without requiring any other external device. A 3G or 4G chip may be used preferably as a 2G connection on a Nokia 5800 was found to transfer data at a rate of 520 kbps using 1.69 W, while a 3G connection transferred at 960 kbps using 1.73 W. Therefore, the 3G chip would use negligibly more power for almost twice the transfer speed, thereby halving half the transfer time and using much less energy from the battery.

In some cases, the wearable system may opportunistically transfer data when in close proximity to a streaming outlet. For example, the system may avoid data transmission when it is not within close proximity of a streaming outlet, and, when nearby a streaming outlet (e.g., a linked phone), may send the data to the external device via Bluetooth and to the Internet via the external device. This is both convenient and "free" in the sense that it utilizes existing cellular data plans.

Limiting the frequency with which data is streamed increases the wearable system's battery life. In one non-limiting example, the system may be set to stream automatically in the morning and following a time stamp. Regardless of the data transmission scheme, the system stores all the data it collects. Data may also be streamed on demand by a user, for example, by turning a physical component on the system and holding it or by initiating a process on the mobile application or receiving device. In some embodiments, the data transmission frequency may be automatically adjusted based on one or more physiological parameters, e.g., heart rate. For example, higher heart rates may prompt more frequent and real-time streaming transmission of data.

The computing device 2200 may run any operating system 2216, such as any of the versions of the Microsoft® Windows® operating systems, the different releases of the Unix and Linux operating systems, any version of the MacOS® for Macintosh computers, any embedded operating system, any real-time operating system, any open source operating system, any proprietary operating system, any operating systems for mobile computing devices, or any other operating system capable of running on the computing device and performing the operations described herein. In exemplary embodiments, the operating system 2216 may be run in native mode or emulated mode. In an exemplary embodiment, the operating system 2216 may be run on one or more cloud machine instances.

V. Exemplary Network Environments

Various aspects and functions of the implementations may be distributed among one or more computer systems configured to provide a service to one or more client computers, or to perform an overall task as part of a distributed system. Additionally, aspects may be performed on a client-server or multi-tier system that includes components distributed among one or more server systems that perform various functions. Thus, the implementations are not limited to executing on any particular system or group of systems. Further, aspects may be implemented in software, hardware or firmware, or any combination thereof. Thus, aspects may be implemented within methods, acts, systems, system placements and components using a variety of hardware and software configurations, and they are not limited to any particular distributed architecture, network or communication protocol. Furthermore, aspects may be implemented as specially-programmed hardware and/or software.

Figure 23:
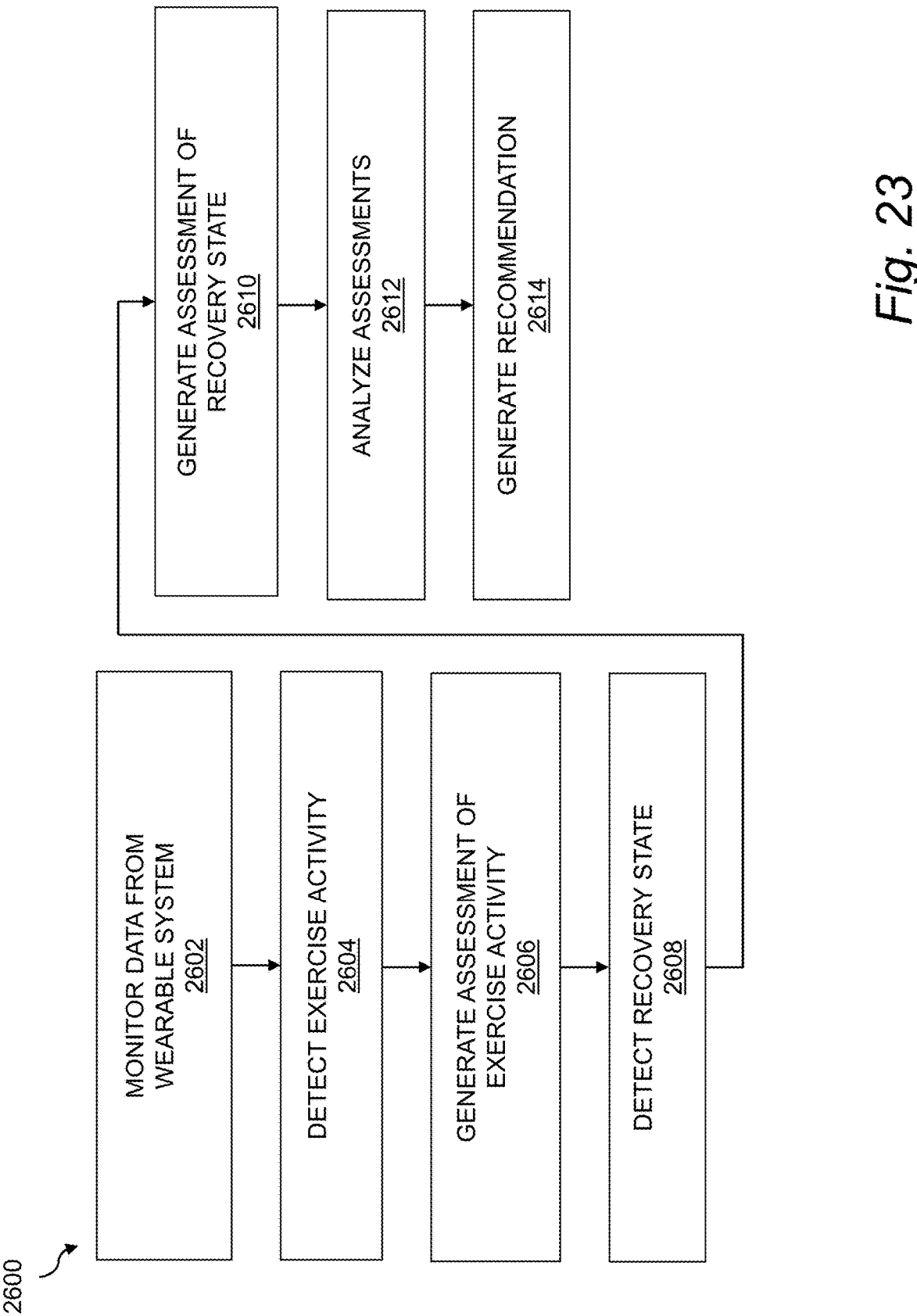
FIG. 23 is a flow chart of a method for assessing recovery and making exercise recommendations.

FIG. 23 is a block diagram of an exemplary system 2300, e.g., a distributed computer system in which various aspects and functions may be practiced. The distributed computer system 2300 may include one or more computer systems.

For example, as illustrated, the distributed computer system 2300 includes three computer systems 2302, 2304 and 2306. As shown, the computer systems 2302, 2304, 2306 are interconnected by, and may exchange data through, a communication network 2308. The network 2308 may include any communication network through which computer systems may exchange data. To exchange data via the network 2308, the computer systems and the network may use various methods, protocols and standards including, but not limited to, token ring, Ethernet, wireless Ethernet, Bluetooth, TCP/IP, UDP, HTTP, FTP, SNMP, SMS, MMS, SS7, JSON, XML, REST, SOAP, CORBA, IIOP, RMI, DCOM and Web Services. To ensure data transfer is secure, the computer systems may transmit data via the network using a variety of security measures including, but not limited to, TSL, SSL and VPN. While the distributed computer system 2300 illustrates three networked computer systems, the distributed computer system may include any number of computer systems, networked using any medium and communication protocol.

Various aspects and functions may be implemented as specialized hardware or software executing in one or more computer systems. As depicted, the computer system 2300 includes a processor 2310, a memory 2312, a bus 2314, an interface 2316 and a storage system 2318. The processor 2310, which may include one or more microprocessors or other types of controllers, can perform a series of instructions that manipulate data. The processor 2310 may be a well-known commercially-available processor such as an Intel Pentium, Intel Atom, ARM Processor, Motorola PowerPC, SGI MIPS, Sun UltraSPARC or Hewlett-Packard PA-RISC processor, or may be any other type of processor or controller as many other processors and controllers are available. The processor 2310 may be a mobile device or smart phone processor, such as an ARM Cortex processor, a Qualcomm Snapdragon processor or an Apple processor. As shown, the processor 2310 is connected to other system placements, including a memory 2312, by the bus 2314.

The memory 2312 may be used for storing programs and data during operation of the computer system 2300. Thus, the memory 2312 may be a relatively high performance, volatile, random access memory such as a dynamic random access memory (DRAM) or static memory (SRAM). However, the memory 2312 may include any device for storing data, such a disk drive or other non-volatile storage device, such as flash memory or phase-change memory (PCM). Various embodiments can organize the memory 2312 into particularized and, in some cases, unique structures to perform the aspects and functions disclosed herein.

Components of the computer system 2300 may be coupled by an interconnection element such as the bus 2314. The bus 2314 may include one or more physical busses (for example, buses between components that are integrated within the same machine) and may include any communication coupling between system placements including specialized or standard computing bus technologies such as IDE, SCSI, PCI and InfiniBand. Thus, the bus 2314 enables communications (for example, data and instructions) to be exchanged between system components of the computer system 2300.

Computer system 2300 also includes one or more interface devices 2316, such as input devices, output devices and combination input/output devices. The interface devices 2316 may receive input, provide output, or both. For example, output devices may render information for external presentation. Input devices may accept information from external sources. Examples of interface devices include, but are not limited to, keyboards, mouse devices, trackballs, microphones, touch screens, printing devices, display screens, speakers, network interface cards, and the like. The interface devices 2316 allow the computer system 2300 to exchange information and communicate with external entities, such as users and other systems.

Storage system 2318 may include one or more computer-readable and computer-writeable non-volatile and non-transitory storage media on which computer-executable instructions are encoded that define a program to be executed by the processor. The storage system 2318 also may include information that is recorded on or in the media, and this information may be processed by the program. More specifically, the information may be stored in one or more data structures specifically configured to conserve storage space or increase data exchange performance. The instructions may be persistently stored as encoded signals, and the instructions may cause a processor to perform any of the functions described herein. A medium that can be used with various embodiments may include, for example, optical disk, magnetic disk or flash memory, among others. In operation, the processor 2310 or some other controller may cause data to be read from the non-transitory recording media into another memory, such as the memory 2312, that allows for faster access to the information by the processor than does the storage medium included in the storage system 2318. The memory may be located in the storage system 2318 and/or in the memory 2312. The processor 2310 may manipulate the data within the memory 2312, and then copy the data to the medium associated with the storage system 2318 after processing is completed. A variety of components may manage data movement between the media and the memory 2312, and the present disclosure is not limited thereto.

Further, the implementations are not limited to a particular memory system or storage system. Although the computer system 2300 is shown by way of example as one type of computer system upon which various aspects and functions may be practiced, aspects are not limited to being implemented on the computer system. Various aspects and functions may be practiced on one or more computers having different architectures or components than that shown in the illustrative figures. For instance, the computer system 2300 may include specially-programmed, special-purpose hardware, such as for example, an application-specific integrated circuit (ASIC) tailored to perform a particular operation disclosed herein. Another embodiment may perform the same function using several general-purpose computing devices running MAC OS® System X with Motorola PowerPC® processors and several specialized computing devices running proprietary hardware and operating systems.

The computer system 2300 may include an operating system that manages at least a portion of the hardware placements included in computer system 2300. A processor or controller, such as processor 2310, may execute an operating system which may be, among others, a Windows-based operating system (for example, Windows NT, Windows 2000/ME, Windows XP, Windows 7, or Windows Vista) available from the Microsoft Corporation, a MAC OS® System X operating system available from Apple Computer, one of many Linux-based operating system distributions (for example, the Enterprise Linux operating system available from Red Hat Inc.), a Solaris operating system available from Sun Microsystems, or a UNIX operating systems available from various sources. The operating system may be a mobile device or smart phone operating system, such as Windows Mobile, Android or iOS. Many other operating systems may be used, and embodiments are not limited to any particular operating system.

The processor and operating system together define a computing platform for which application programs in high-level programming languages may be written. These component applications may be executable, intermediate (for example, C# or JAVA bytecode) or interpreted code which communicate over a communication network (for example, the Internet) using a communication protocol (for example, TCP/IP). Similarly, functions may be implemented using an object-oriented programming language, such as SmallTalk, JAVA, C++, Ada, or C# (C-Sharp). Other object-oriented programming languages may also be used. Alternatively, procedural, scripting, or logical programming languages may be used.

Additionally, various functions may be implemented in a non-programmed environment (for example, documents created in HTML, XML or other format that, when viewed in a window of a browser program, render aspects of a graphical-user interface or perform other functions). Further, various embodiments may be implemented as programmed or non-programmed placements, or any combination thereof. For example, a web page may be implemented using HTML while a data object called from within the web page may be written in C++. Thus, the implementations are not limited to a specific programming language and any suitable programming language could also be used.

A computer system included within an embodiment may perform functions outside the scope of the embodiment. For instance, aspects of the system may be implemented using an existing product. Aspects of the system may be implemented on database management systems such as SQL Server available from Microsoft of Seattle, Washington; Oracle Database from Oracle of Redwood Shores, California; and MySQL from Sun Microsystems of Santa Clara, California; or integration software such as WebSphere middleware from IBM of Armonk, New York. However, a computer system running, for example, SQL Server may be able to support both aspects in accord with the implementations and databases for sundry applications not within the scope of the disclosure.

It is also understood that a system 2302 of the distributed computer system 2300 may include a wearable physiological measurement system, e.g., configured to provide collection and monitoring of physiological data. In this manner, the system 2302 may include one or more sensors 2320. As discussed herein, the sensors 2320 may include a heart rate monitor. In some embodiments, the system 2302 may further include one or more of sensors 2320 for detecting calorie burn, distance, and activity. Calorie burn may be based on a user's heart rate, and a calorie burn measurement may be improved if a user chooses to provide his or her weight and/or other physical parameters. In some embodiments, manual entering of data is not required in order to derive calorie burn; however, data entry may be used to improve the accuracy of the results. In some embodiments, if a user has forgotten to enter a new weight, he/she can enter it for past weeks and the calorie burn may be updated accordingly.

The sensors 2320 may include one or more sensors for activity measurement. In some embodiments, the system 2302 may include one or more multi-axes accelerometers and/or gyroscope to provide a measurement of activity. In some embodiments, the accelerometer may further be used to filter a signal from the optical sensor for measuring heart rate and to provide a more accurate measurement of the heart rate. In some embodiments, the system 2302 may include a multi-axis accelerometer to measure motion and calculate distance, whether it be in real terms as steps or miles or as a converted number. Activity sensors may be used, for example, to classify or categorize activity, such as walking, running, performing another sport, standing, sitting or lying down. In some embodiments, one or more of collected physiological data may be aggregated to generate an aggregate activity level. For example, heart rate, caloric burn, and distance may be used to derive an aggregate activity level. The aggregate level may be compared with or evaluated relative to previous recordings of the user's aggregate activity level, as well as the aggregate activity levels of other users.

The sensors 2320 may include a thermometer for monitoring the user's body or skin temperature. In one embodiment, the sensors 2320 may be used to recognize sleep based on a temperature drop, GSR data, lack of activity according to data collected by the accelerometer, and reduced heart rate as measured by the heart rate monitor. The body temperature, in conjunction with heart rate monitoring and motion, may be used to interpret whether a user is sleeping or just resting, as body temperature drops significantly when an individual is about to fall asleep), and how well an individual is sleeping as motion indicates a lower quality of sleep. The body temperature may also be used to determine whether the user is exercising and to categorize and/or analyze activities.

The system 2302 may further include one or more batteries 2322. According to one embodiment, the one or more batteries 2322 may be configured to allow continuous wear and usage of the system 2302. In one embodiment, the system 2302 may include two or more batteries 2322. The system 2302 may include a removable battery that may be recharged using a charger. In one example, the removable battery may be configured to slip in and out of a head portion of the system, attach onto the bracelet, or the like. In one example, the removable battery may be able to power the system for around a week. Additionally, the system 2302 may include a built-in battery. The built-in battery may be recharged by the removable battery. The built-in battery may be configured to power the bracelet for around a day on its own. When the more removable battery is being charged, the user does not need to remove the system 2302 and may continue collecting data using the built-in battery. In other embodiments, the two batteries 2322 may both be removable and rechargeable.

In some embodiments, the system 2302 may include a battery 2322 that is a wireless rechargeable battery. For example, the battery 2322 may be recharged by placing the system or the battery on a rechargeable mat. In other example, the battery 2322 may be a long range wireless rechargeable battery. In other embodiments, the battery 2322 may be a rechargeable via motion. In yet other embodiments, the battery 2322 may be rechargeable using a solar energy source.

The wearable system 2302 may include one or more non-transitory computer-readable media (the storage 2318) for storing raw data detected by the sensors 2320 of the system 2302 and processed data calculated by the processor 2310 of the system. Thus, this system 2302 may include a processor 2310, a memory (the storage 2318), a bus 2314, a network interface 2324, and an interface 2316. The network interface 2324 may be configured to wirelessly communicate data to an external network. Some embodiments of the wearable system 2302 may be configured to stream information wirelessly to a social network. In some embodiments, data streamed from a user's wearable system to an external network may be accessed by the user via a website.

The network interface 2324 may be configured such that data collected by the system 2302 may be streamed wirelessly. In some embodiments, data may be transmitted automatically, without the need to manually press any buttons. In some embodiments, the system may include a cellular chip built into the system 2302. In one example, the network interface 2324 may be configured to stream data using Bluetooth technology. In another example, the network interface 2324 may be configured to stream data using a cellular data service, such as via a 3G, 4G, or 5G cellular network.

Figure 21:
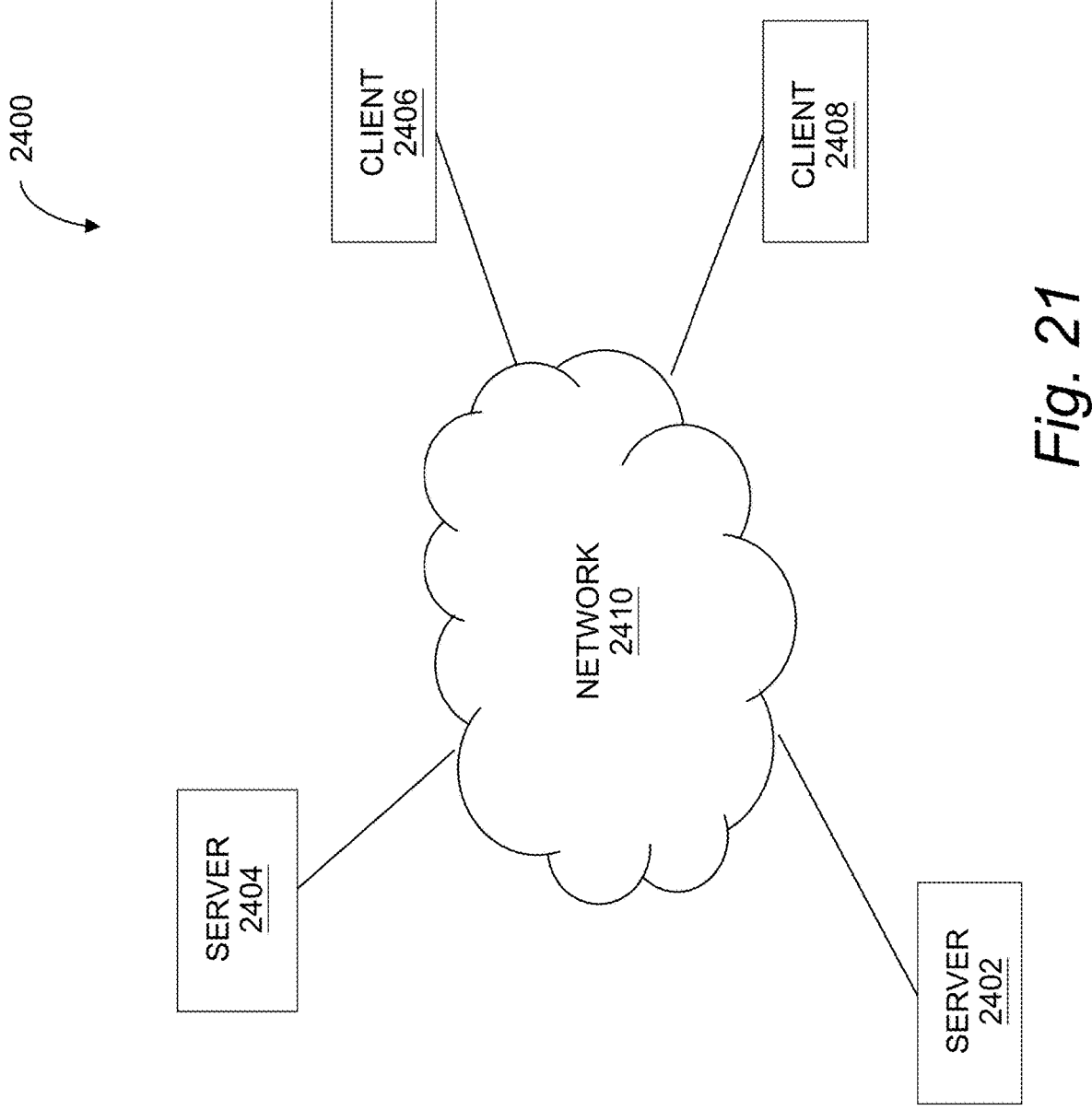
FIG. 21 is a diagram of a network environment suitable for a distributed implementation of embodiments described herein.

FIG. 21 is a diagram of an exemplary network environment 2400 suitable for a distributed implementation of exemplary embodiments. The network environment 2400 may include one or more servers 2402 and 2404 coupled to one or more clients 2406 and 2408 via a communication network 2410. The network interface 2212 and the network device 2222 of the computing device 2200 enable the servers 2402 and 2404 to communicate with the clients 2406 and 2408 via the communication network 2410. The communication network 2410 may include, but is not limited to, the Internet, an intranet, a LAN (Local Area Network), a WAN (Wide Area Network), a MAN (Metropolitan Area Network), a wireless network, an optical network, and the like. The communication facilities provided by the communication network 2410 are capable of supporting distributed implementations of exemplary embodiments.

In an exemplary embodiment, the servers 2402 and 2404 may provide the clients 2406 and 2408 with computer-readable and/or computer-executable components or products under a particular condition, such as a license agreement. For example, the computer-readable and/or computer-executable components or products may include those for providing and rendering any of the user interfaces disclosed herein. The clients 2406 and 2408 may provide and render an exemplary graphical user interface using the computer-readable and/or computer-executable components and products provided by the servers 2402 and 2404.

Alternatively, in another exemplary embodiment, the clients 2406 and 2408 may provide the servers 2402 and 2404 with computer-readable and computer-executable components or products under a particular condition, such as a license agreement. For example, in an exemplary embodiment, the servers 2402 and 2404 may provide and render an exemplary graphical user interface using the computer-readable and/or computer-executable components and products provided by the clients 2406 and 2408.

Figure 22:
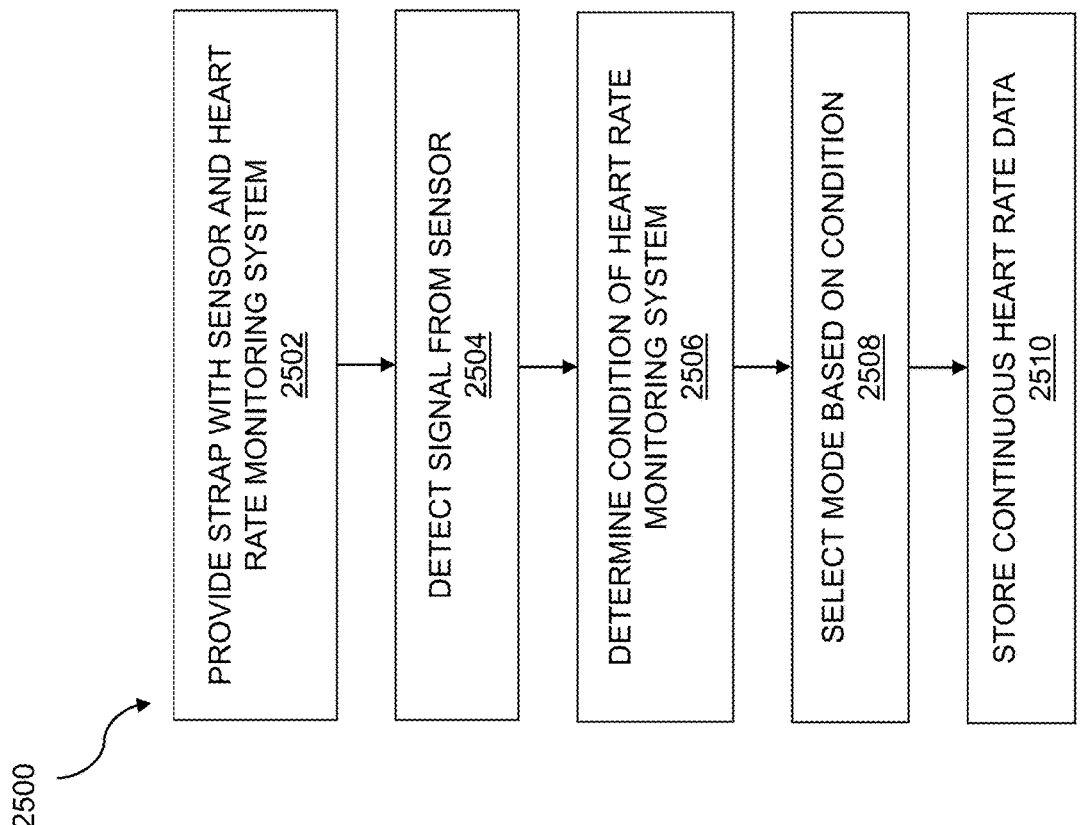
FIG. 22 is a flow chart illustrating a method for selecting modes of acquiring heart rate data.

FIG. 22 is a flow chart illustrating a method for selecting modes of acquiring heart rate data.

As shown in step 2502, the method 2500 may include providing a strap with a sensor and a heart rate monitoring system. The strap may be shaped and sized to fit about an appendage. For example, the strap may be any of the straps described herein, including, without limitation, a bracelet. The heart rate monitoring system may be configured to provide two or more different modes for detecting a heart rate of a wearer of the strap. The modes may include the use of optical detectors (e.g., light detectors), light emitters, motion sensors, a processing module, algorithms, other sensors, a peak detection technique, a frequency domain technique, variable optical characteristics, non-optical techniques, and so on.

As shown in step 2504, the method 2500 may include detecting a signal from the sensor. The signal may be detected by one or more sensors, which may include any of the sensors described herein. The signal may include, without limitation, one or more signals associated with the heart rate of the user, other physiological signals, an optical signal, signals based on movement, signals based on environmental factors, status signals (e.g., battery life), historical information, and so on.

As shown in step 2506, the method 2500 may include determining a condition of the heart rate monitoring system, which may be based upon the signal. The condition may include, without limitation, an accuracy of heart rate detection determined using a statistical analysis to provide a confidence level in the accuracy, a power consumption, a battery charge level, a user activity, a location of the sensor or motion of the sensor, an environmental or contextual condition (e.g., ambient light conditions), a physiological condition, an active condition, an inactive condition, and so on. This may include detecting a change in the condition, responsively selecting a different one of the two or more different modes, and storing additional continuous heart rate data obtained using at least one of the two or more different modes.

As shown in step 2508, the method 2500 may include selecting one of the two or more different modes for detecting the heart rate based on the condition. For example, based on the motion status of the user, the method may automatically and selectively activate one or more light emitters to determine a heart rate of the user. The system may also or instead determine the type of sensor to use at a given time based on the level of motion, skin temperature, heart rate, and the like. Based on a combination of these factors the system may selectively choose which type of sensor to use in monitoring the heart rate of the user. A processor or the like may be configured to select one of the modes. For example, if the condition is the accuracy of heart rate detection determined using a statistical analysis to provide a confidence level in the accuracy, the processor may be configured to select a different one of the modes when the confidence level is below a predetermined threshold.

As shown in step 2510, the method 2500 may include storing continuous heart rate data using one of the two or more different modes. This may include communicating the continuous heart rate data from the strap to a remote data repository. This may also or instead include storing the data locally, e.g., on a memory included on the strap. The memory may be removable, e.g., via a data card or the like, or the memory may be permanently attached/integral with the strap or a component thereof. The stored data (e.g., heart rate data) may be for the user's private use, for example, when in a private setting, or the data may be shared when in a shared setting (e.g., on a social networking site or the like). The method 2500 may further include the use of a privacy switch operable by the user to controllably restrict communication of a portion of the data, e.g., to the remote data repository.

FIG. 23 is a flow chart of a method for assessing recovery and making exercise recommendations.

As shown in step 2602, the method 2600 may include monitoring data from a wearable system. The wearable system may be a continuous-monitoring, physiological measurement system worn by a user. The data may include heart rate data, other physiological data, summary data, motion data, fitness data, activity data, or any other data described herein or otherwise contemplated by a skilled artisan.

As shown in step 2604, the method 2600 may include detecting exercise activity. This may include automatically detecting exercise activity of the user. The exercise activity may be detected through the use of one or more sensors as described herein. The exercise activity may be sent to a server that, e.g., performs step 2606 described below.

As shown in step 2606, the method 2600 may include generating an assessment of the exercise activity. This may include generating a quantitative assessment of the exercise activity. Generating a quantitative assessment of the exercise activity may include analyzing the exercise activity on a remote server. Generating a quantitative assessment may include the use of the algorithms discussed herein. The method 2600 may also include generating periodic updates to the user concerning the exercise activity. The method 2600 may also include determining a qualitative assessment of the exercise activity and communicating the qualitative assessment to the user.

As shown in step 2608, the method 2600 may include detecting a recovery state. This may include automatically detecting a physical recovery state of the user. The recovery state may be detected through the use of one or more sensors as described herein. The recovery state may be sent to a server that, e.g., performs step 2610 described below.

As shown in step 2610, the method 2600 may include generating an assessment of the recovery state. This may include generating a quantitative assessment of the physical recovery state. Generating a quantitative assessment may include the use of the algorithms discussed herein. Generating a quantitative assessment of the physical recovery state may include analyzing the physical recovery state on a remote server. The method 2600 may also include generating periodic updates to the user concerning the physical recover state. The method 2600 may also include determining a qualitative assessment of the recovery state and communicating the qualitative assessment to the user.

As shown in step 2612, the method 2600 may include analyzing the assessments, i.e., analyzing the quantitative assessment of the exercise activity and the quantitative assessment of the physical recovery. The analysis may include the use of one or more of the algorithms described herein, a statistical analysis, and so on. The analysis may include the use of a remote server.

As shown in step 2614, the method 2600 may include generating a recommendation. This may include automatically generating a recommendation on a change to an exercise routine of the user based on the analysis performed in step 2612. This may also or instead include determining a qualitative assessment of the exercise activity and/or recovery state, and communicating the qualitative assessment(s) to the user. The recommendation may be generated on a remote server. The recommendation may be communicated to the user in an electronic mail, it may be presented to the user in a web page, other communications interface, or the like. Generating the recommendation may be based upon a number of cycles of exercise and rest.

The method 2600 described above, or any of the methods discussed herein, may also or instead be implemented on a computer program product including non-transitory computer executable code embodied in a non-transitory computer-readable medium that executes on one or more computing devices to perform the method steps. For example, code may be provided that performs the various steps of the methods described herein.

Figure 24:
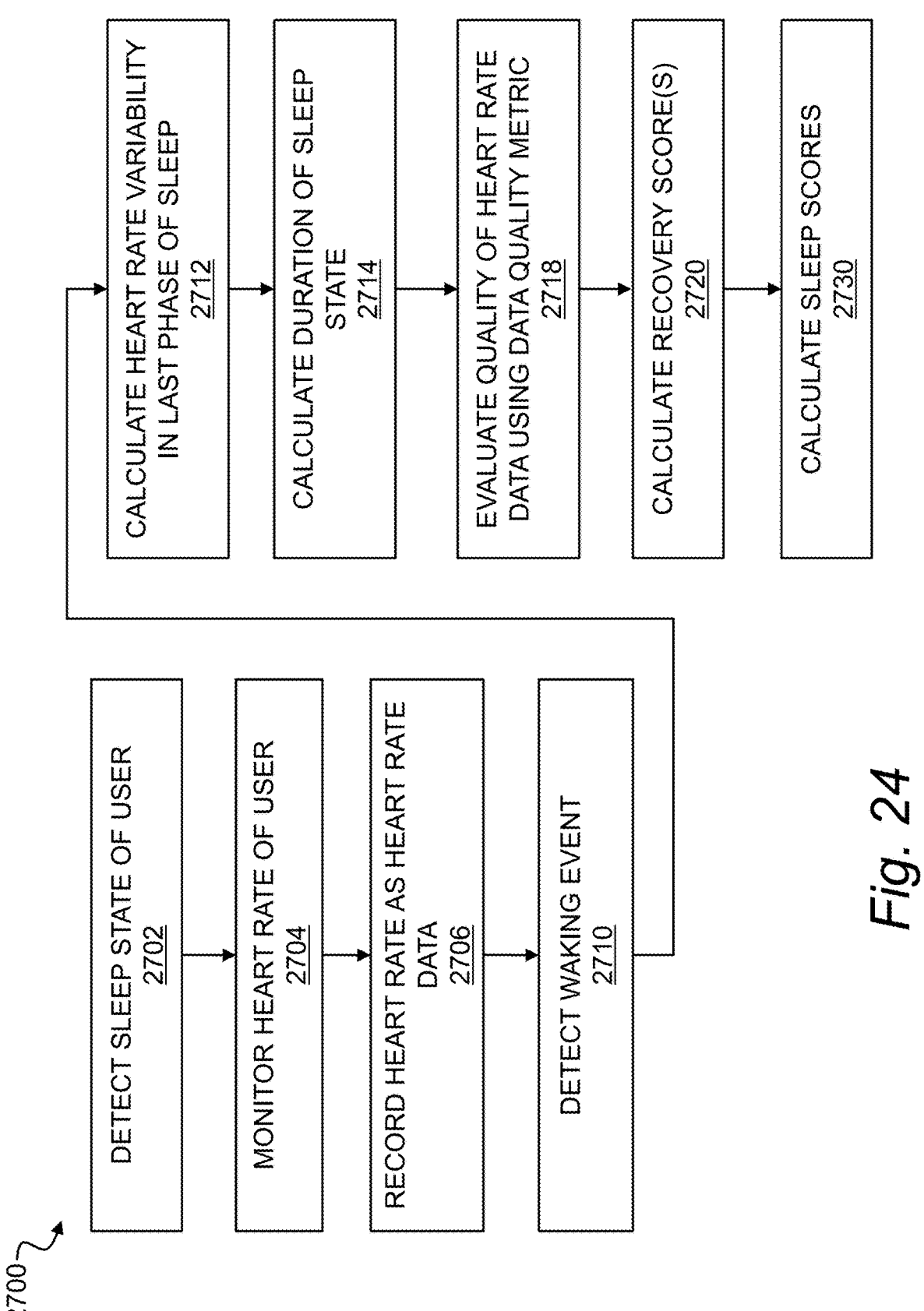
FIG. 24 is a flow chart illustrating a method for detecting heart rate variability in sleep states.

FIG. 24 is a flow chart illustrating a method for detecting heart rate variability in sleep states. The method 2700 may be used in cooperation with any of the devices, systems, and methods described herein, such as by operating a wearable, continuous physiological monitoring device to perform the following steps. The wearable, continuous physiological monitoring system may for example include a processor, one or more light emitting diodes, one or more light detectors configured to obtain heart rate data from a user, and one or more other sensors to assist in detecting stages of sleep. In general, the method 2700 aims to measure heart rate variability in the last phase of sleep before waking in order to provide a consistent and accurate basis for calculating a physical recovery score.

As shown in step 2702, the method 2700 may include detecting a sleep state of a user. This may, for example, include any form of continuous or periodic monitoring of sleep states using any of a variety of sensors or algorithms as generally described herein.

Sleep states (also be referred to as "sleep phases," "sleep cycles," "sleep stages," or the like) may include rapid eye movement (REM) sleep, non-REM sleep, or any states/stages included therein. The sleep states may include different phases of non-REM sleep, including Stages 1-3. Stage 1 of non-REM sleep generally includes a state where a person's eyes are closed, but the person can be easily awakened; Stage 2 of non-REM sleep generally includes a state where a person is in light sleep, i.e., where the person's heart rate slows and their body temperature drops in preparation for deeper sleep; and Stage 3 of non-REM sleep generally includes a state of deep sleep, where a person is not easily awakened. Stage 3 is often referred to as delta sleep, deep sleep, or slow wave sleep (i.e., from the high amplitude but small frequency brain waves typically found in this stage). Slow wave sleep is thought to be the most restful form of sleep, which relieves subjective feelings of sleepiness and restores the body.

REM sleep on the other hand typically occurs 1-2 hours after falling asleep. REM sleep may include different periods, stages, or phases, all of which may be included within the sleep states that are detected as described herein. During REM sleep, breathing may become more rapid, irregular and shallow, eyes may jerk rapidly (thus the term "Rapid Eye Movement" or "REM"), and limb muscles may be temporarily paralyzed. Brain waves during this stage typically increase to levels experienced when a person is awake. Also, heart rate, cardiac pressure, cardiac output, and arterial pressure may become irregular when the body moves into REM sleep. This is the sleep state in which most dreams occur, and, if awoken during REM sleep, a person can typically remember the dreams. Most people experience three to five intervals of REM sleep each night.

Homeostasis is the balance between sleeping and waking, and having proper homeostasis may be beneficial to a person's health. Lack of sleep is commonly referred to as sleep deprivation, which tends to cause slower brain waves, a shorter attention span, heightened anxiety, impaired memory, mood disorders, and general mental, emotional, and physical fatigue. Sleep debt (the effect of not getting enough sleep) may result in the diminished abilities to perform high-level cognitive functions. A person's circadian rhythms (i.e., biological processes that display an endogenous, entrainable oscillation of about 24 hours) may be a factor in a person's optimal amount of sleep. Thus, sleep may in general be usefully monitored as a proxy for physical recovery. However, a person's heart rate variability at a particular moment during sleep—during the last phase of sleep preceding a waking event—can further provide an accurate and consistent basis for objectively calculating a recovery score following a period of sleep.

According to the foregoing, sleep of a user may be monitored to detect various sleep states, transitions, and other sleep-related information. For example, the device may monitor/detect the duration of sleep states, the transitions between sleep states, the number of sleep cycles or particular states, the number of transitions, the number of waking events, the transitions to an awake state, and so forth. Sleep states may be monitored and detected using a variety of strategies and sensor configurations according to the underlying physiological phenomena. For example, body temperature may be usefully correlated to various sleep states and transitions. Similarly, galvanic skin response may be correlated to sweating activity and various sleep states, any of which may also be monitored, e.g., with a galvanic skin response sensor, to determine sleep states. Physical motion can also be easily monitored using accelerometers or the like, which can be used to detect waking or other activity involving physical motion. In another aspect, heart rate activity itself may be used to infer various sleep states and transitions, either alone or in combination with other sensor data. Other sensors may also or instead be used to monitor sleep activity, such as brain wave monitors, pupil monitors, and so forth, although the ability to incorporate these types of detection into a continuously wearable physiological monitoring device may be somewhat limited depending on the contemplated configuration.

As shown in step 2704, the method 2700 may include monitoring a heart rate of the user substantially continuously with the continuous physiological monitoring system. Continuous heart rate monitoring is described above in significant detail, and the description is not repeated here except to note generally that this may include raw sensor data, heart rate data or peak data, and heart rate variability data over some historical period that can be subsequently correlated to various sleep states and activities.

As shown in step 2706, the method 2700 may include recording the heart rate as heart rate data. This may include storing the heart rate data in any raw or processed form on the device, or transmitting the data to a local or remote location for storage. In one aspect, the data may be stored as peak-to-peak data or in some other semi-processed form without calculating heart rate variability. This may be useful as a technique for conserving processing resources in a variety of contexts, for example where only the heart rate variability at a particular time is of interest. Data may be logged in some unprocessed or semi-processed form, and then the heart rate variability at a particular point in time can be calculated once the relevant point in time has been identified.

As shown in step 2710, the method 2700 may include detecting a waking event at a transition from the sleep state of the user to an awake state. It should be appreciated that the waking event may be a result of a natural termination of sleep, e.g., after a full night's rest, or in response to an external stimulus that causes awakening prior to completion of a natural sleep cycle. Regardless of the precipitating event(s), the waking event may be detected via the various physiological changes described above, or using any other suitable techniques. While the emphasis herein is on a wearable, continuous monitoring device, it will be understood that the device may also receive inputs from an external device such as a camera (for motion detection) or an infrared camera (for body temperature detection) that can be used to aid in accurately assessing various sleep states and transitions.

Thus the wearable, continuous physiological monitoring system may generally detect a waking event using one or more sensors including, for example, one or more of an accelerometer, a galvanic skin response sensor, a light sensor, and so forth. For example, in one aspect, the waking event may be detected using a combination of motion data and heart rate data.

As shown in step 2712, the method 2700 may include calculating a heart rate variability of the user at a moment in a last phase of sleep preceding the waking event based upon the heart rate data. While a waking event and a history of sleep states are helpful information for assessing recovery, the method 2700 described herein specifically contemplates use of the heart rate variability in a last phase of sleep as a consistent foundation for calculating recovery scores for a device user. Thus step 2712 may also include detecting a slow wave sleep period immediately prior to the waking event, or otherwise determining the end of a slow wave or deep sleep episode immediately preceding the waking event.

It will be appreciated that the last phase of sleep preceding a natural waking event may be slow wave sleep. However, where a sleeper is awakened prematurely, this may instead include a last recorded episode of REM sleep or some other phase of sleep immediately preceding the waking event. This moment—the end of the last phase of sleep before waking—is the point at which heart rate variability data provides the most accurate and consistent indicator of physical recovery. Thus, with the appropriate point of time identified, the historical heart rate data (in whatever form) may be used with the techniques described above to calculate the corresponding heart rate variability. It will be further noted that the time period for this calculation may be selected with varying degrees of granularity depending on the ability to accurate detect the last phase of sleep and an end of the last phase of sleep. Thus for example, the time may be a predetermined amount of time before waking, or at the end of slow wave sleep, or some predetermined amount of time before the end of slow wave sleep is either detected or inferred. In another aspect, an average heart rate variability or similar metric may be determined for any number of discrete measurements within a window around the time of interest.

As shown in step 2714, the method 2700 may include calculating a duration of the sleep state. The quantity and quality of sleep may be highly relevant to physical recovery, and as such the duration of the sleep state may be used to calculate a recovery score.

As shown in step 2718, the method 2700 may include evaluating a quality of heart rate data using a data quality metric for a slow wave sleep period, e.g., the slow wave sleep period occurring most recently before the waking event. As noted above, the quality of heart rate measurements may vary over time for a variety of reasons. Thus the quality of heart rate data may be evaluated prior to selecting a particular moment or window of heart rate data for calculating heart rate variability, and the method 2700 may include using this quality data to select suitable values for calculating a recovery score. For example, the method 2700 may include calculating the heart rate variability for a window of predetermined duration within the slow wave sleep period having the highest quality of heart rate data according to the data quality metric.

As shown in step 2720, the method 2700 may include calculating a recovery score for the user based upon the heart rate variability from the last phase of sleep. The calculation may be based on other sources of data. For example, the calculation of recovery score may be based on the duration of sleep, the stages of sleep detected or information concerning the stages (e.g., amount of time in certain stages), information regarding the most recent slow wave sleep period or another sleep period/state, information from the GSR sensor or other sensor(s), and so on. The method 2700 may further include calculating additional recovery scores after one or more other waking events of the user for comparison to the previously calculated recovery score. The actual calculation of a discovery score is described in substantial detail above, and this description is not repeated here except to note that the use of a heart rate variability measurement from the last phase of sleep provides an accurate and consistent basis for evaluating the physical recovery state of a user following a period of sleep.

As shown in step 2730, the method 2700 may include calculating a sleep score and communicating this score to a user.

In one aspect, the sleep score may be a measure of prior sleep performance. For example, a sleep performance score may quantify, on a scale of 0-100, the ratio of the hours of sleep during a particular resting period compared to the sleep needed. On this scale, if a user sleeps six hours and needed eight hours of sleep, then the sleep performance may be calculated as 75%. The sleep performance score may begin with one or more assumptions about needed sleep, based on, e.g., age, gender, health, fitness level, habits, genetics, and so forth and may be adapted to actual sleep patterns measured for an individual over time.

The sleep score may also or instead include a sleep need score or other objective metric that estimates an amount of sleep needed by the user of the device in a next sleep period. In general, the score may be any suitable quantitative representation including, e.g., a numerical value over some predetermined scale (e.g., 0-10, 1-100, or any other suitable scale) or a representation of a number of hours of sleep that should be targeted by the user. In another aspect, the sleep score may be calculated as the number of additional hours of sleep needed beyond a normal amount of sleep for the user.

The score may be calculated using any suitable inputs that capture, e.g., a current sleep deficit, a measure of strain or exercise intensity over some predetermined prior interval, an accounting for any naps or other resting, and so forth. A variety of factors may affect the actual sleep need, including physiological attributes such as age, gender, health, genetics and so forth, as well as daytime activities, stress, napping, sleep deficit or deprivation, and so forth. The sleep deficit may itself be based on prior sleep need and actual sleep performance (quality, duration, waking intervals, etc.) over some historical window. In one aspect, an objective scoring function for sleep need may have a model of the form:

$$SleepNeed = \text{Baseline} + f_1(\text{strain}) + f_2(\text{debt}) - \text{Naps}$$

In general, this calculation aims to estimate the ideal amount of sleep for best rest and recovery during a next sleep period. When accounting for time falling asleep, periods of brief wakefulness, and so forth, the actual time that should be dedicated to sleep may be somewhat higher, and this may be explicitly incorporated into the sleep need calculation, or left for a user to appropriately manage sleep habits.

In general, the baseline sleep may represent a standard amount of sleep needed by the user on a typical rest day (e.g., with no strenuous exercise or workout). As noted above, this may depend on a variety of factors, and may be estimated or measured for a particular individual in any suitable manner. The strain component, $f_1(\text{strain})$, may be assessed based on a previous day's physical intensity, and will typically increase the sleep need. Where intensity or strain is measured on an objective scale from 0 to 21, the strain calculation may take the following form, which yields an additional sleep time needed in minutes for a strain, i:

$$f(i) = \frac{1.7}{1 + e^{\frac{17-i}{3.5}}}$$

The sleep debt, $f_2$(debt), may generally measure a carry-over of needed sleep that was not attained in a previous day. This may be scaled, and may be capped at a maximum, according to individual sleep characteristics or general information about long term sleep deficit and recovery. Naps may also be accounted for directly by correcting the sleep need for any naps that have been taken, or by calculating a nap factor that is scaled or otherwise manipulated or calculated to more accurately track the actual effect of naps on prospective sleep need.

However calculated, the sleep need may be communicated to a user, such as by displaying a sleep need on a wrist-worn physiological monitoring device, or by sending an email, text message or other alert to the user for display on any suitable device.

Described herein are physiological monitoring devices, systems, and methods for detecting and analyzing periods in which a user is asleep or resting. However, the actual sleep achieved during sleep opportunities (that is, the time dedicated to sleep) is typically only about 90%-95% of the total available timewise opportunity. The remaining 5%-10% of a sleep opportunity may be lost to brief sleep disruptions lasting anywhere from a few seconds to a few minutes. This presents conflicting challenges for sleep evaluation. On one hand, subjects that review their sleep metrics may prefer to have quantitative analysis performed as quickly as possible so that data is available shortly after waking. On the other hand, initiating computationally expensive, server-side sleep analysis may be wasteful in those instances where the sleep disruption is transient in nature and the subject intends to return to sleep. In order to help minimize computational loads associated with discarded data, while still providing timely sleep analysis for subjects that intend to awake, the techniques described herein may be advantageously employed to predict a subject's sleep intention in order to arrive more quickly at an accurate assessment of whether a waking event reflects a transient sleep disruption or a subject's intention to awaken.

As described herein, a system may be configured to detect sleep intention for a subject in order to determine the likelihood that a given waking event is associated with an intention to remain awake. This analysis may apply empirical rules, and/or rules derived from historical data for a user or population such as the user's prior sleep patterns, other users' sleep patterns, or a combination thereof. In one aspect, sleep intention may be detected using a probabilistic analysis of historical data for a user, including information such as the time of day, the day of the week, seasonal factors, and so on. The detection of sleep intention may also be aided by a probabilistic analysis of data from a broader population, e.g., through look-alike models and whole-population analysis.

Figure 25:
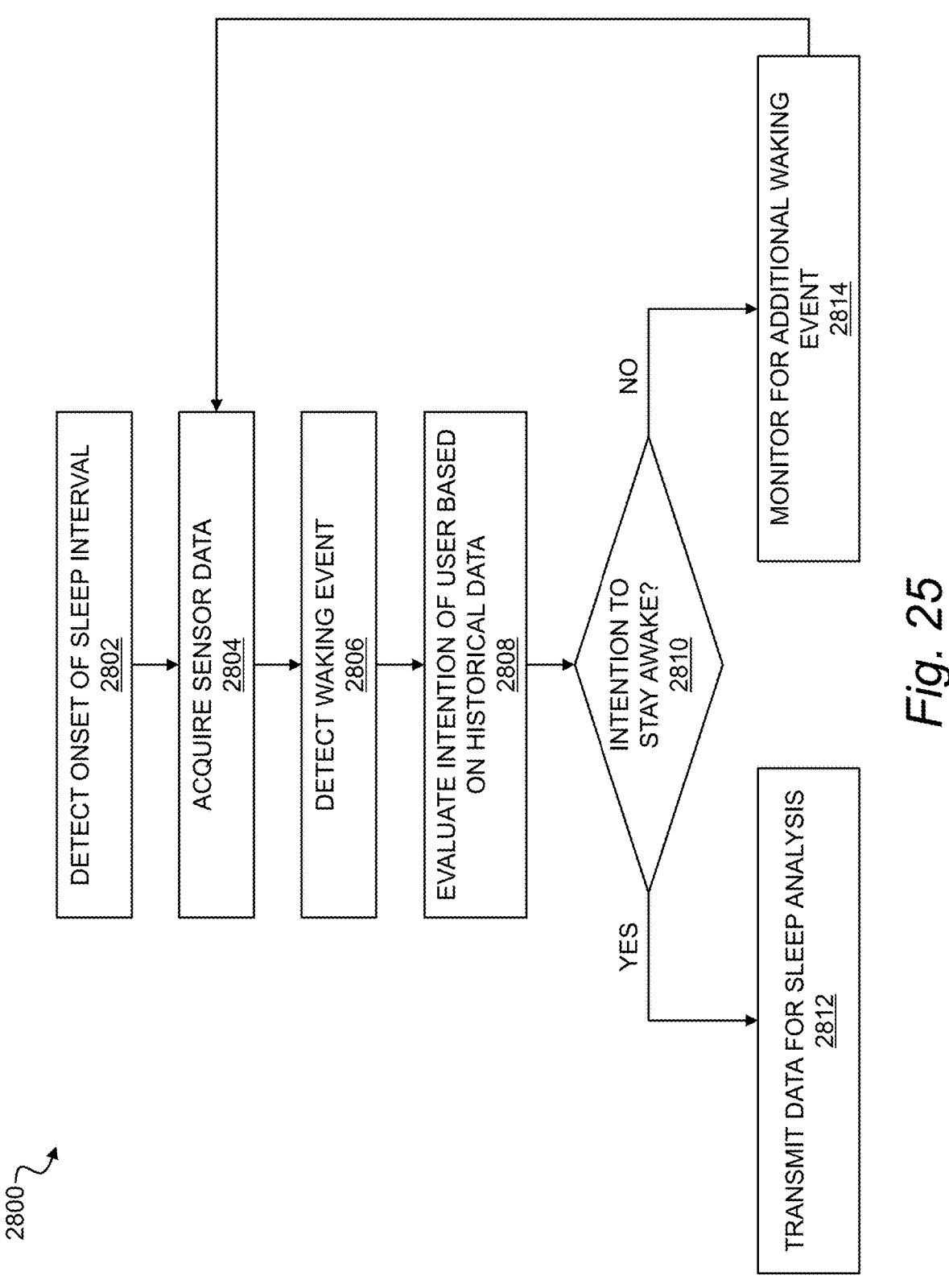
FIG. 25 is a flow chart illustrating a method for detecting sleep intention.

FIG. 25 is a flow chart illustrating a method for detecting sleep intention. The method 2800 may be used in any of the methods or systems described herein to improve sleep scoring. In general, the techniques described below seek to quickly and accurately differentiate between users that intend to arise and users that will return to sleep, more specifically in order to conserve processing resources that are used to evaluate sleep quality for those instances where a user is likely to remain awake and review sleep metrics. This may have particular advantage in systems where, e.g., sleep processing is computationally expensive, and/or where sleep processing is performed by remote processing resources.

As shown in step 2802, the method 2800 may include detecting an onset of a sleep interval. In general, a device such as any of the devices described herein may continuously, substantially continuously, or intermittently acquire data such as heart rate data, and analyze this data to detect the onset of a sleep interval. In this context, the sleep interval may include an interval over which a user desires an analysis (such as sleep quality or duration), or an interval otherwise suitable for evaluation and amenable to automatic detection. For example, the sleep interval may include an entire night's sleep, e.g., measured from when a user gets into bed and falls asleep until when the user rises from bed to begin the following day. The interval may also or instead include any substantial interval of inactivity or sleep detected for a user. In another aspect, the sleep interval may include other sleep sessions such as naps and the like. The sleep interval may include a sleep opportunity (the time dedicated to sleep) for a user, e.g., where the onset of the sleep interval begins when a user positions oneself for sleep (e.g., lays down in bed) before the user begins to fall asleep for the first time.

It will be understood that a sleep interval may include subsequent, intermittent events such as when the user briefly awakes and falls back asleep after waking. Thus, a sleep interval may include one or more sub-intervals, e.g., where a user falls back asleep after awakening, where a user is in different modes of sleep, and so on. To this end, the method 2800 may also or instead include detecting an onset and conclusion of such sub-intervals, particularly where such information is relevant to evaluating the quality or quantity of sleep, and/or where such information assists in accurately identifying the onset of a sleep interval to be analyzed, and/or for use in an analysis of historical data.

It will be understood that numerous sleep detection techniques are known in the art based on the physiology of sleep. Thus, for example, changes in body temperature, perspiration, movement, heart rate, respiratory rate, eye movement, blood pressure, blood oxygen levels, brain waves, and the like may all be used, either individually or in combination, to detect an onset of sleep, as well as transitions among various stages of sleep (e.g., light sleep, deep sleep, REM sleep, etc.), each of which has objectively measurable physical characteristics. Some or all of these physical characteristics may be detected by a wearable physiological monitoring device such as any of the devices described herein and used to detect an onset of sleep at the beginning of a sleep interval, as well as multiple subintervals within a sleep cycle and transitions among different stages of sleep.

As shown in step 2804, the method 2800 may include acquiring sensor data, e.g., with a physiological monitor worn by a user during a sleep interval. The physiological monitor may be a wearable physiological monitor such as any of the devices described herein, including without limitation a bracelet or other wearable strap that includes one or more sensors for acquiring physiological data. By way of example, the sensors may include light emitting diodes and light sensors (e.g., for acquiring photoplethysmography data), accelerometers (for acquiring motion data), thermocouples (for acquiring temperature data), microphones (for acquiring acoustic data), capacitive sensors or the like (for acquiring galvanic skin response data), and so forth. However, it should be understood that the techniques described herein are more generally applicable to any physiological monitoring system in which computing resources might advantageously be conserved by accurately identifying sleep intention, or more specifically, identifying when a user awakes and intends to stay awake after an interval of sleep.

As shown in step 2806, the method 2800 may include detecting a waking event with the physiological monitor. The waking event may be any event that objectively and measurably signals the user waking from the sleep interval. The waking event may include a single event such as a change in heart rate or a detection of motion, or the waking event may include a compound event based on numerous measurable events that collectively indicate arousal from a sleeping state.

Numerous techniques may be used, either alone or in combination, to detect a waking event. For example, detecting the waking event may include detecting physical movement inconsistent with sleep—e.g., sitting up or getting out of bed, raising an extremity above a predetermined height, movements of body parts above or below predetermined speed or acceleration thresholds, and so on. Detecting the waking event may also or instead include detecting heart rate activity inconsistent with sleep—e.g., a change in heart rate variability or a heart rate above or below a predetermined threshold that indicates a waking event, or any other change(s) in heart activity generally inconsistent with sleep. Detecting the waking event may also or instead include detecting a body temperature inconsistent with sleep—e.g., a body temperature above or below a predetermined threshold. Other techniques or criteria for detecting the waking event are also or instead possible as will be understood by a skilled artisan. For example, a machine learning system may be trained to recognize a waking event based on any available data from the device or the device context, including external data such as a time of sunrise or a day of the week, as well as locally sensed data such as increased light or sudden sounds in an area around the user.

However detected, the waking event may be associated with a user intention to return to sleep or a user intention to remain awake. For example, in one aspect a user may intend to awake, as evidenced by subsequent activity and a sustained, wakeful state. The waking event may instead include an event where the intention of the user is to return to sleep, as evidenced by a return to a motionless, prone position and subsequent sleep activity. These types of waking events may include, for example, general restlessness, a user response to an audio disturbance, and so on. Thus, it may be advantageous to determine the user's sleep intention prior to performing sleep analysis or other computationally expensive processing of acquired physiological data.

As shown in step 2808, the method 2800 may include, in response to the waking event, evaluating sleep intention, e.g., whether an intention of the user is to stay awake or return to sleep.

The evaluation of sleep intention may be based on historical sleep data. For example, historical sleep data may be obtained from a sleep history for the user, or otherwise customized for or adapted to a specific user. The historical sleep data may also or instead include data derived from other users, such as users of a platform or system for analyzing sleep, users having similar hardware or software for physiological monitoring, and so on. It will be understood that the historical sleep data may further be filtered, categorized, weighted, or selected to increase accuracy for the evaluation regarding the intention of the user to stay awake or return to sleep. For example, the historical sleep data for a population may be filtered to provide data for similarly situated users—this can be based on physiological, biological, or demographic data such as age, height, weight, physical condition, diet, medical history, and so forth.

The intention of the user may be evaluated using a probabilistic analysis of historical sleep data to calculate or otherwise estimate a probability of the intention of the user to stay awake or return to sleep according to one or more variables including categorical variables and quantitative variables. For example, useful categorical variables may include the day of the week, a season, and/or a geographical location. Useful quantitative variables may include a duration of the waking event, a duration of the preceding sleep interval, an amount of time away from a typical waking time, a duration of physical after waking movement, and/or an amount of physical movement. Certain variables such as the time of day may be used as a quantitative variable (e.g., when calculating temporal distance from a normal waking time) and/or a categorical variable (e.g., whether waking time is within an ordinary waking interval).

In one aspect, thresholds may be applied to quantitative variables in order to derive rules for evaluating sleep intention. For example, if the duration or amount of physical movement of the user after waking exceeds a predetermined threshold for movement (which threshold can be based on the user's historical data, other historical data, or a default threshold set by an administrator or the like), then a determination may be made that the user intends to stay awake. In another aspect, the fact of exceeding the threshold, or the amount in excess of the threshold, may be used as a basis for increasing a probability that the intention of the user is to stay awake.

The variables used in a probabilistic analysis of the historical sleep data to determine a probability of the intention of the user to stay awake or return to sleep may be weighted, where such weights may be default weights for certain variables or customized weights for a particular user or set of users. By way of example, for certain users with sporadic sleep patterns, one or more quantitative variables may be weighted more than one or more categorical variables. Specific variables, such as the duration of a preceding sleep interval and the amount or duration of movement after waking may provide good initial indicators of sleep intention, and may be used either exclusively or in a heavily weighted manner to evaluate sleep intention.

In one aspect, evaluating user sleep intention may include training a machine learning algorithm to estimate a likelihood of sleep intention outcomes based on one or more characteristics of the preceding sleep interval and/or the waking event, such as any of the variables or sensed conditions described herein. This machine learning algorithm may be applied to current data for a waking user to determine a probability distribution for sleep intention outcomes, or more generally to determine whether it is more likely that a user intends to arise or return to sleep. Other probabilistic models such as a stochastic model or the like may also or instead be used to evaluate the likelihood that a user intends to remain awake.

As shown in step 2810, the method 2800 may include determining a sleep intention for a user, or as illustrated, by determining whether the user sleep intention is to stay awake. This may include applying any of the analyses described above, or any other suitable probabilistic analyses, machine learning algorithms, rule-based evaluation, or other analyses, as well as combinations of the foregoing, to determine whether it is more likely that the user intends to stay awake or return to sleep. Evaluating sleep intention may advantageously be performed locally, e.g., on a wearable physiological monitor or the like, in order to conserve network communication resources (including bandwidth and power consumption) for those circumstances where the user is likely to request sleep metrics in the near future. A compact machine learning model or other algorithms may usefully be deployed on the wearable physiological monitoring device for this purpose.

As shown in step 2812, when it is determined that the intention of the user is to stay awake, the method 2800 may include transmitting data from a physiological monitor to a remote server for sleep analysis. It will be understood, however, that the sleep analysis, or a portion thereof, may also or instead be conducted locally, e.g., using a processor and memory of a local computing device or the physiological monitoring device that acquired the data. This may include any form of preprocessing, signal conditioning, compression, encryption, or other data processing that might usefully be performed in a local computing context before transmitting to a remote resource. The sleep analysis may include any of the sleep analysis described herein, or any other sleep analysis known in the art, and may usefully be presented to the user on a local device as one or more sleep metrics that evaluate the quality and/or duration of the entire sleep interval, and/or individual sleep stages or sleep cycles within the entire sleep interval.

As shown in step 2814, when it is determined that the intention of the user is to return to sleep, the method 2800 may include monitoring for an additional waking event upon which to evaluate the intention of the user, such as by returning to step 2804 and acquiring additional sensor data.

It will be understood that the method 2800 described above may performed in whole or in part by a computer program product. For example, a computer program product comprising computer executable code embodied on a nontransitory computer readable medium that, when executing on a wearable physiological monitor, may perform the steps of: acquiring sensor data with the wearable physiological monitor worn by a user during a sleep interval, the sensor data including photoplethysmography data and accelerometer data; detecting a waking event with the wearable physiological monitor by analyzing the accelerometer data to locate physical movement inconsistent with sleep; in response to the waking event, evaluating whether an intention of the user is to stay awake or return to sleep using a probabilistic analysis based on historical sleep data to evaluate a probability that the intention of the user is to stay awake based on at least one of a duration of the sleep interval and a duration of the physical movement inconsistent with sleep; when it is more likely that the intention of the user is to stay awake, transmitting data from the wearable physiological monitor to a remote server for sleep analysis; and, when it is more likely that the intention of the user is to return to sleep, monitoring for an additional waking event upon which to evaluate the intention of the user.

Figure 26:
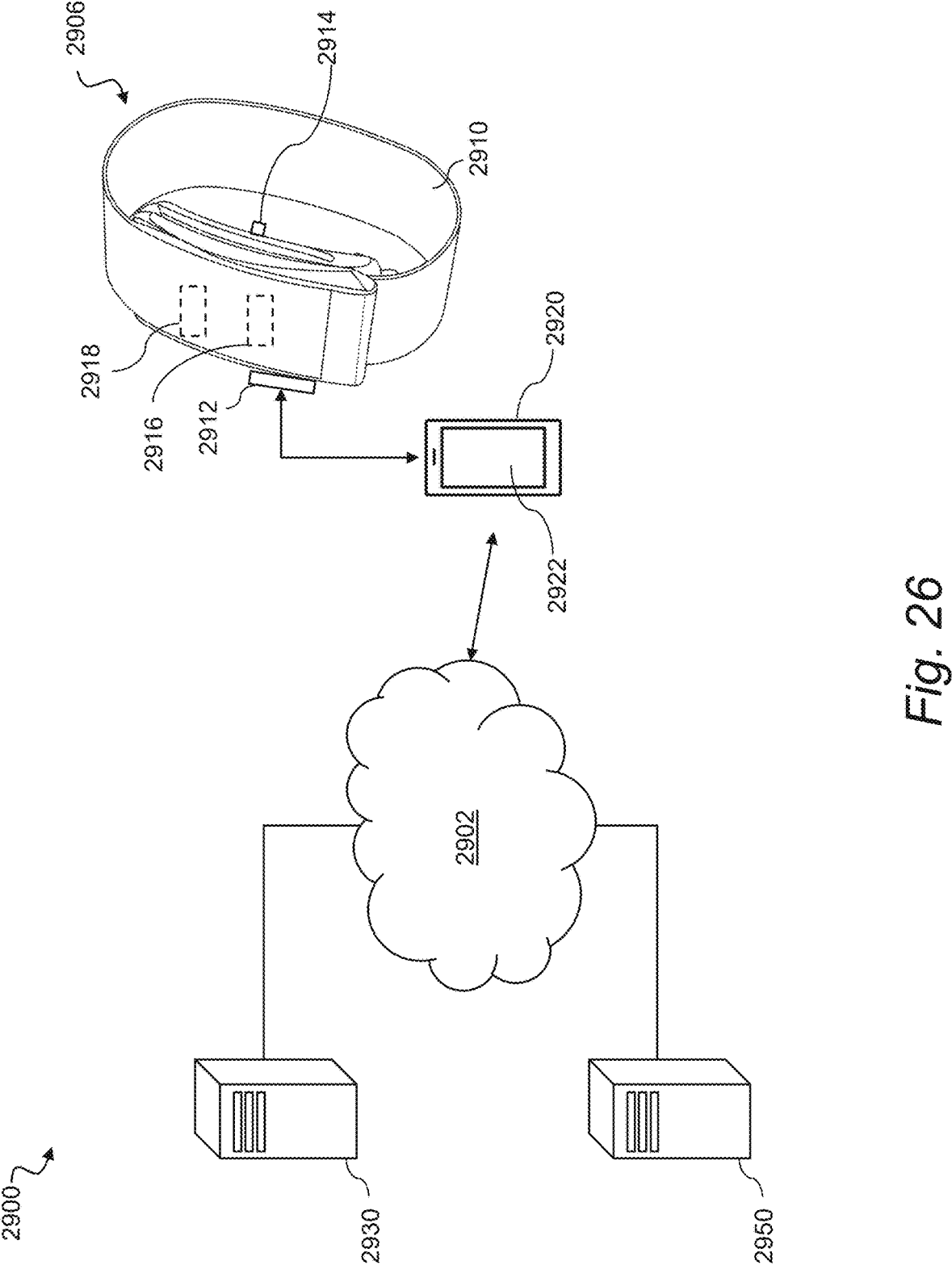
FIG. 26 illustrates a physiological monitoring system.

FIG. 26 illustrates a physiological monitoring system, which may be used with the method 2800 described above, or any of the other methods or devices, described herein. In general, the system 2900 may include a physiological monitor 2906, a user device 2920, a remote server 2930 with a remote data processing resource (such as any of the processors or processing resources described herein), and one or more other resources 2950, all of which may be interconnected through a data network 2902.

The data network 2902 may be any of the data networks described herein. For example, the data network 2902 may be any network(s) or internetwork(s) suitable for communicating data and information among participants in the system 2900. This may include public networks such as the Internet, private networks, telecommunications networks such as the Public Switched Telephone Network or cellular networks using third generation (e.g., 3G or IMT-2000), fourth generation (e.g., LTE (E-UTRA) or WiMAX-Advanced (IEEE 802.16m)), fifth generation (e.g., 5G), and/or other technologies, as well as any of a variety of corporate area or local area networks and other switches, routers, hubs, gateways, and the like that might be used to carry data among participants in the system 2900. This may also include local or short range communications networks suitable, e.g., for coupling the physiological monitor 2906 to the user device 2920, or otherwise communicating with local resources.

The physiological monitor 2906 may, in general, be any physiological monitoring device, such as any of the wearable physiological monitoring devices described herein, and may include a network interface 2912, one or more sensors 2914, a processor 2916, a memory 2918, and a wearable strap 2910 for retaining the device in a desired location on a user. The network interface 2912 may be configured to coupled one or more participants of the system 2900 in a communicating relationship, e.g., with the remote server 2930. The one or more sensors 2914 may include any of the sensors described herein, or any other sensors suitable for physiological monitoring. By way of example and not limitation, the one or more sensors 2914 may include one or more of a light source, and optical sensor, an accelerometer, a gyroscope, a temperature sensor, a galvanic skin response sensor, an environmental sensor (e.g., for measuring ambient temperature, humidity, lighting, and the like), a geolocation sensor, a temporal sensor, an electrodermal activity sensor, and the like.

The processor 2916 and memory 2918 may be any of the processors and memories described herein and suitable for deployment in a physiological monitoring device. In one aspect, the memory 2918 may store physiological data obtained by monitoring a user with the one or more sensors 2914. The processor 2916 may be configured to obtain heart rate data from the user based on the data from the sensors 2914. The processor 2916 may be further configured to assist in a determination of sleep intention of the user as generally described herein. To this end, the processor 2916 may be configured to detect an onset of a sleep interval, and to detect a waking event objectively indicative of the user waking from the sleep interval based on data from the sensors 2914. Further, in response to the waking event, the processor 2916 may be configured to evaluate whether an intention of the user is to stay awake or return to sleep based on historical sleep data. In this manner, when the intention of the user is to stay awake, the processor 2916 may be configured to transmit at least some of the data from the memory 2918 to the remote server 2930 for sleep analysis. And, when the intention of the user is to return to sleep, the processor 2916 may be configured to monitor for an additional waking event upon which to evaluate the intention of the user.

The system 2900 may further include a remote data processing resource executing on a remote server 2930. The remote data processing resource may be any of the processors described herein, and may be configured to receive data transmitted from the memory 2918 of the physiological monitor 2906, and to evaluate the sleep of the user during the sleep interval.

The system 2900 may also include one or more user devices 2920, which may work together with the physiological monitor, e.g., to provide a display for user data and analysis, and/or to provide a communications bridge from the network interface 2912 of the physiological monitor 2906 to the data network 2902 and the remote server 2930. For example, physiological monitor 2906 may communicate locally with a user device 2920, such as a smartphone of a user, via short-range communications, e.g., Bluetooth, or the like, e.g., for the exchange of data between the physiological monitor 2906 and the user device 2920, and the user device 2920 may communicate with the remote server 2930 via the data network 2902. Computationally intensive processing, such as sleep quality analysis, may be performed at the remote server 2930, which may have greater memory capabilities and processing power than the physiological monitor 2906 that acquires the data.

The user device 2920 may include any computing device as described herein, including without limitation a smartphone, a desktop computer, a laptop computer, a network computer, a tablet, a mobile device, a portable digital assistant, a cellular phone, a portable media or entertainment device, and so on. The user device 2920 may provide a user interface 2922 for access to data and analysis by a user, and/or to control operation of the physiological monitor 2906. The user interface 2922 may be maintained by a locally-executing application on the user device 2920, or the user interface 2922 may be remotely served and presented on the user device 2920, e.g., from the remote server 2930 or the one or more other resources 2950.

In general, the remote server may include data storage, a network interface, and/or other processing circuitry. The remote server 2930 may process data from the physiological monitor and perform sleep analysis or any of the other analysis described herein, and may host a user interface for remote access to this data, e.g., from the user device 2920. The remote server 2930 may include a web server or similar front end that facilitates web-based access by the user devices 2920 or the physiological monitor 2906 to the capabilities of the remote server 2930 or other components of the system 2900.

The other resources 2950 may include any resources that can be usefully employed in the devices, systems, and methods as described herein. For example, these other resources 2950 may include without limitation other data networks, human actors (e.g., programmers, researchers, annotators, editors, analysts, and so forth), sensors (e.g., audio or visual sensors), data mining tools, computational tools, data monitoring tools, algorithms, and so forth. The other resources 2950 may also or instead include any other software or hardware resources that may be usefully employed in the networked applications as contemplated herein. For example, the other resources 2950 may include payment processing servers or platforms used to authorize payment for access, content, or option/feature purchases, or otherwise. In another aspect, the other resources 2950 may include certificate servers or other security resources for third-party verification of identity, encryption or decryption of data, and so forth. In another aspect, the other resources 2950 may include a desktop computer or the like co-located (e.g., on the same local area network with, or directly coupled to through a serial or USB cable) with a user device 2920, wearable strap 2910, or remote server 2930. In this case, the other resources 2950 may provide supplemental functions for components of the system 2900.

The other resources 2950 may also or instead include one or more web servers that provide web-based access to and from any of the other participants in the system 2900. While depicted as a separate network entity, it will be readily appreciated that the other resources 2950 (e.g., a web server) may also or instead be logically and/or physically associated with one of the other devices described herein, and may, for example, include or provide a user interface 2922 for web access to a remote server 2930 or a database in a manner that permits user interaction through the data network 2902, e.g., from the physiological monitor 2906 or the user device 2920.

According to the foregoing, there is disclosed herein a system including a wearable strap; a network connection for coupling in a communicating relationship with a remote server; one or more sensors for monitoring a user of the wearable strap; a memory storing data from the one or more sensors; and a processor configured to obtain heart rate data from the user based on the data from the one or more sensors, the processor further configured to detect an onset of a sleep interval, to detect a waking event objectively indicative of the user waking from the sleep interval based on data from the one or more sensors, and, in response to the waking event, to evaluate whether an intention of the user is to stay awake or return to sleep based on historical sleep data, wherein, when the intention of the user is to stay awake, the processor is configured to transmit at least some of the data from the memory to the remote server for sleep analysis, and, when the intention of the user is to return to sleep, the processor is configured to monitor for an additional waking event upon which to evaluate the intention of the user. The system may also include a remote data processing resource executing on the remote server, the remote data processing resource configured to receive data transmitted from the memory, and to evaluate the sleep of the user during the sleep interval.

The above systems, devices, methods, processes, and the like may be realized in hardware, software, or any combination of these suitable for the control, data acquisition, and data processing described herein. This includes realization in one or more microprocessors, microcontrollers, embedded microcontrollers, programmable digital signal processors or other programmable devices or processing circuitry, along with internal and/or external memory. This may also, or instead, include one or more application specific integrated circuits, programmable gate arrays, programmable array logic components, or any other device or devices that may be configured to process electronic signals. It will further be appreciated that a realization of the processes or devices described above may include computer-executable code created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software.

Thus, in one aspect, each method described above and combinations thereof may be embodied in computer executable code that, when executing on one or more computing devices, performs the steps thereof. In another aspect, the methods may be embodied in systems that perform the steps thereof, and may be distributed across devices in a number of ways, or all of the functionality may be integrated into a dedicated, standalone device or other hardware. The code may be stored in a non-transitory fashion in a computer memory, which may be a memory from which the program executes (such as random access memory associated with a processor), or a storage device such as a disk drive, flash memory or any other optical, electromagnetic, magnetic, infrared or other device or combination of devices. In another aspect, any of the systems and methods described above may be embodied in any suitable transmission or propagation medium carrying computer-executable code and/or any inputs or outputs from same. In another aspect, means for performing the steps associated with the processes described above may include any of the hardware and/or software described above. All such permutations and combinations are intended to fall within the scope of the present disclosure.

The method steps of the implementations described herein are intended to include any suitable method of causing such method steps to be performed, consistent with the patentability of the following claims, unless a different meaning is expressly provided or otherwise clear from the context. So, for example, performing the step of X includes any suitable method for causing another party such as a remote user, a remote processing resource (e.g., a server or cloud computer) or a machine to perform the step of X. Similarly, performing steps X, Y, and Z may include any method of directing or controlling any combination of such other individuals or resources to perform steps X, Y, and Z to obtain the benefit of such steps. Thus, method steps of the implementations described herein are intended to include any suitable method of causing one or more other parties or entities to perform the steps, consistent with the patentability of the following claims, unless a different meaning is expressly provided or otherwise clear from the context. Such parties or entities need not be under the direction or control of any other party or entity, and need not be located within a particular jurisdiction.

It will be appreciated that the methods and systems described above are set forth by way of example and not of limitation. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context. Thus, while particular embodiments have been shown and described, it will be apparent to those skilled in the art that various changes and modifications in form and details may be made therein without departing from the spirit and scope of this disclosure and are intended to form a part of the invention as defined by the following claims, which are to be interpreted in the broadest sense allowable by law.

What is claimed is:

1. A method comprising:
acquiring sensor data from a physiological monitor worn by a user during a sleep interval;
transmitting the sensor data from the physiological monitor to a remote server, the remote server configured to perform a sleep analysis based on the sensor data from the physiological monitor;
detecting, with a processor, a waking event based on the sensor data, the waking event objectively indicative of the user waking from the sleep interval;
in response to the waking event, evaluating the sensor data with the processor to determine whether an intention of the user is to stay awake or return to sleep;
determining that the intention of the user is to return to sleep;
in response to determining the intention to return to sleep, deferring the sleep analysis with the remote server and continuing to monitor sensor data from the physiological monitor for a subsequent waking event;
detecting the subsequent waking event;
determining that the intention of the user is to stay awake;
in response to determining the intention of the user is to stay awake, initiating the sleep analysis with the remote server, the sleep analysis including a calculation of one or more sleep metrics that evaluate the sleep interval based on the sensor data from the physiological monitor; and
providing a result of the sleep analysis to the user.

2. The method of claim 1, wherein detecting the waking event includes detecting physical movement inconsistent with sleep.

3. The method of claim 1, wherein detecting the waking event includes detecting heart rate activity inconsistent with sleep.

4. The method of claim 1, wherein detecting the waking event includes detecting a body temperature inconsistent with sleep.

5. The method of claim 1, wherein evaluating the sensor data with the processor includes evaluating the sensor data using a probabilistic analysis of historical sleep data to determine a probability of the intention of the user to stay awake or return to sleep according to one or more variables.

6. The method of claim 5, wherein the historical sleep data includes data for the user.

7. The method of claim 5, wherein the historical sleep data includes data for other users.

8. The method of claim 5, wherein the one or more variables include a categorical variable.

9. The method of claim 8, wherein the categorical variable includes at least one of a time of day, a day, and a time of year.

10. The method of claim 5, wherein the one or more variables include at least one of a duration of the waking event, a duration of the sleep interval, an amount of time away from a typical waking time, a duration of physical movement, and an amount of physical movement.

11. The method of claim 1, wherein the sensor data includes at least one of photoplethysmography data, accelerometer data, and temperature data.

12. The method of claim 1, further comprising detecting an onset of the sleep interval based on the sensor data.

13. The method of claim 1, wherein evaluating whether the intention of the user is to stay awake or return to sleep includes training a machine-learning algorithm to estimate a likelihood of the intention based on one or more characteristics of the sleep interval.

14. The method of claim 1, wherein evaluating whether the intention of the user is to stay awake includes processing the sensor data with at least one of the physiological monitor, a mobile device coupled in a communicating relationship with the physiological monitor, and a remote server coupled in a communicating relationship with the physiological monitor.

15. The method of claim 1, wherein initiating the sleep analysis includes requesting an update to the sensor data with the remote server, and performing the sleep analysis with the remote server based on the sensor data and the update to the sensor data.

16. The method of claim 1, wherein providing the result of the sleep analysis includes transmitting the result from the remote server to a mobile device associated with the user.

17. The method of claim 16, further comprising displaying the result of the sleep analysis to the user on the mobile device.

18. The method of claim 1, wherein initiating the sleep analysis with the remote server when the intention of the user is to stay awake includes initiating the sleep analysis in a manner to provide a timely analysis shortly after waking.

19. The method of claim 18, further comprising calculating an intensity score for the user at least in part based on a heart rate variability calculated for the user during the sleep interval.

20. The method of claim 18, further comprising calculating a recovery score for the user at least in part based on a heart rate variability calculated for the user during the sleep interval.

* * * * *